US009139582B2

(12) United States Patent
Parham et al.

(10) Patent No.: US 9,139,582 B2
(45) Date of Patent: Sep. 22, 2015

(54) ORGANIC ELECTROLUMINESCENT DEVICES

(75) Inventors: Amir Hossain Parham, Frankfurt am Main (DE); Christof Pflumm, Darmstadt (DE); Philipp Stoessel, Frankfurt am Main (DE); Arne Buesing, Frankfurt am Main (DE); Dominik Joosten, Frankfurt am Main (DE)

(73) Assignee: Merck Patent GmbH, Darmstadt (DE)

(*) Notice: Subject to any disclaimer, the term of this patent is extended or adjusted under 35 U.S.C. 154(b) by 0 days.

(21) Appl. No.: 13/695,933

(22) PCT Filed: Mar. 29, 2011

(86) PCT No.: PCT/EP2011/001573

§ 371 (c)(1), (2), (4) Date: Nov. 2, 2012

(87) PCT Pub. No.: WO2011/137951

PCT Pub. Date: Nov. 10, 2011

(65) Prior Publication Data

US 2013/0053555 A1 Feb. 28, 2013

(30) Foreign Application Priority Data

May 4, 2010 (DE) ........................ 10 2010 019 306

(51) Int. Cl.

| | |
|---|---|
| *C07D 471/04* | (2006.01) |
| *C07D 471/14* | (2006.01) |
| *C07D 471/16* | (2006.01) |
| *C07D 471/22* | (2006.01) |
| *C07D 487/04* | (2006.01) |
| *C07D 495/14* | (2006.01) |
| *C07D 513/04* | (2006.01) |
| *C07D 513/14* | (2006.01) |
| *C07D 513/16* | (2006.01) |
| *C07F 5/02* | (2006.01) |
| *C07F 7/10* | (2006.01) |
| *C07F 7/12* | (2006.01) |
| *C09B 17/00* | (2006.01) |
| *C09B 21/00* | (2006.01) |
| *C09B 57/00* | (2006.01) |
| *C09K 11/06* | (2006.01) |
| *H01L 51/00* | (2006.01) |
| *H01L 51/50* | (2006.01) |

(52) U.S. Cl.

CPC ........... *C07D 471/04* (2013.01); *C07D 471/14* (2013.01); *C07D 471/16* (2013.01); *C07D 471/22* (2013.01); *C07D 487/04* (2013.01); *C07D 495/14* (2013.01); *C07D 513/04* (2013.01); *C07D 513/14* (2013.01); *C07D 513/16* (2013.01); *C07F 5/025* (2013.01); *C07F 7/10* (2013.01); *C07F 7/12* (2013.01); *C09B 17/00* (2013.01); *C09B 21/00* (2013.01); *C09B 57/00* (2013.01); *C09K 11/06* (2013.01); *H01L 51/0071* (2013.01); *H01L 51/0094* (2013.01); *H01L 51/5096* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/5012* (2013.01); *Y02E 10/549* (2013.01)

USPC ........................................................... 546/47

(58) Field of Classification Search

CPC ....... C07D 471/06; C07D 7/10; C07D 491/16

USPC ............................................... 546/42, 44, 47

See application file for complete search history.

(56) References Cited

U.S. PATENT DOCUMENTS

2005/0121068 A1 6/2005 Sager et al.

FOREIGN PATENT DOCUMENTS

| | | | |
|---|---|---|---|
| JP | 2008270395 | A | 11/2008 |
| JP | 2009033067 | A | 2/2009 |
| WO | WO-96/26186 | A1 | 8/1996 |
| WO | WO-2006033563 | A1 | 3/2006 |
| WO | WO-2008097272 | A3 | 1/2009 |
| WO | WO-2010104047 | A1 | 9/2010 |

OTHER PUBLICATIONS

Xie, Rui-Hua, et al., "Tuning Spectral Properties of Fullerenes by Substitutional Doping", Physical Review, vol. B 69, (2004), pp. 201403-1-201403-4.

Tachikawa Tatsuya, et al., "The Calculation of Electronic Spectra of Protonated Benzodixanthene Analogs", Journal of Photopolymer Science and Technology, vol. 15, No. 1, (2002), pp. 111-114.

Nourry, Arnaud, et al., "Synthesis of New Lavendamycin Analogues", Tetrahedron, vol. 64, (2008), pp. 2241-2250.

Franz, Adam W., et al., "Synthesis and Electronic Properties of Sterically Demanding N-Arylphenothiazines and Unexpected Buchwald-Hartwig Aminations", J. Org. Chem., vol. 73, (2008), pp. 1795-1802.

Gomez-Lor, Berta, et al., "Synthesis of a Triaza Analogue of Crushed-Fullerene by Intramolecular Palladium-Catalyzed Arylation", Organic Letters, vol. 6, No. 17, (2004), pp. 2993-2996.

Zhang, Haiming, et al., "Synthesis of Annulated γ-Carbonlines and Heteropolycycles by the Palladium-Catalyzed Intramolecular Annulation of Alkynes", J. Org. Chem., vol. 68, (2003), pp. 5132-5138.

(Continued)

*Primary Examiner* — Paul V Ward

(74) *Attorney, Agent, or Firm* — Drinker Biddle & Reath LLP

(57) ABSTRACT

The present invention relates to electronic devices, in particular organic electroluminescent devices, comprising compounds of the formula (1), and the corresponding compounds.

17 Claims, No Drawings

(56) References Cited

OTHER PUBLICATIONS

Kelly, T. Ross, et al., "Maxonine: Structure Correction and Synthesis", Tetrahedron Letters, vol. 34, No. 39, (1993), pp. 6173-6176.

De Diesbach, Henri, et al., Helvetica Chemica Acta, XP002636364, vol. 31, No. 724, (1948), pp. 1214-1227.

RN: 904503-77-1, Registry (STN), Aug. 25, 2006.

Translation of Japanese Patent Application No. 2013-508381 First Office Action dated Jan. 20, 2015.

Zhang Halming, et al., Synthesis of Annulated y-Carbolines and Heteropolycycles by the Palladium-Catalyzed Intramolecular Annulation of Alkynes, J. Org. Chem, 2003, 68, 5132-5138.

Markgraf, J. Hodge, et al., "A versatile route to benzocanthinones", Tetrahedron 61 (2005), pp. 9102-9110.

ORGANIC ELECTROLUMINESCENT DEVICES

CROSS-REFERENCE TO RELATED APPLICATIONS

This application is a national stage application (under 35 U.S.C. §371) of PCT/EP2011/001573, filed Mar. 29, 2011, which claims benefit of German application 10 2010 019 306.2, filed May 4, 2010.

The present invention relates to electronic devices, in particular organic electroluminescent devices, and materials for use in electronic devices, in particular in organic electroluminescent devices.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold energy and power efficiency is possible using organometallic compounds as phosphorescent emitters. In general, however, there is still a need for improvement, for example with respect to efficiency, operating voltage and lifetime, in the case of OLEDs, in particular also in the case of OLEDs which exhibit triplet emission (phosphorescence). This applies, in particular, to OLEDs which emit in the relatively short-wave region, for example green.

The properties of phosphorescent OLEDs are determined not only by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties. There is also still a need for improvement in the case of these materials for fluorescent OLEDs.

In accordance with the prior art, ketones (for example in accordance with WO 2004/093207 or WO 2010/006680) or phosphine oxides (for example in accordance with WO 2005/003253), inter alia, are used as matrix materials for phosphorescent emitters. However, there is still a need for improvement, in particular with respect to the efficiency and lifetime of the device, on use of these matrix materials, as in the case of other matrix materials.

In accordance with the prior art, carbazole derivatives, for example in accordance with WO 2005/039246, US 2005/0069729, JP 2004/288381, EP 1205527 or WO 2008/086851, and indolocarbazole derivatives, for example in accordance with WO 2007/063754 or WO 2008/056746, are furthermore employed as matrix materials for phosphorescent emitters in organic electroluminescent devices. These have the disadvantage that they are frequently very oxidation-sensitive, which adversely affects the preparation, purification and storage of the materials and the long-term stability of solutions comprising the materials. Further improvements are desirable here, and also with respect to the efficiency, lifetime and thermal stability of the materials.

The object of the present invention is the provision of compounds which are suitable for use in a fluorescent or phosphorescent OLED, in particular a phosphorescent OLED, for example as matrix material or as hole-transport/electron-blocking material or exciton-blocking material or as electron-transport or hole-blocking material. In particular, it is the object of the present invention to provide matrix materials which are suitable for green- and red-phosphorescent OLEDs.

Surprisingly, it has been found that certain compounds described in greater detail below achieve this object and result in significant improvements in the organic electroluminescent device, in particular with respect to the lifetime, efficiency and operating voltage. This applies, in particular, to red- and green-phosphorescent electroluminescent devices, especially on use of the compounds according to the invention as matrix material. The materials are furthermore distinguished by high oxidation stability in solution and by high temperature stability. The present invention therefore relates to electronic devices, in particular organic electroluminescent devices, which comprise compounds of this type.

The present invention relates to an electronic device comprising a compound of the following formula (1), formula (1)

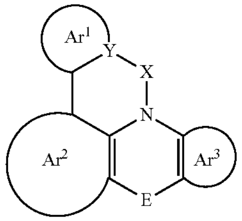

where the following applies to the symbols and indices used:

X is C═O, $C(R)_2$, NR, O, S, C═S, C═NR, C═$C(R)_2$, $Si(R)_2$, BR, PR, P(═O)R, SO or $SO_2$;

Y is C if $Ar^1$ represents a 6-membered aryl or heteroaryl ring group or is C or N if $Ar^1$ represents a 5-membered heteroaryl ring group;

E is a single bond, $C(R)_2$, NR, O, S, C═O, C═S, C═NR, C═$C(R)_2$, $Si(R)_2$, BR, PR, P(═O)R, SO or $SO_2$;

$Ar^1$ is, together with the group Y and the carbon atom explicitly depicted, an aromatic or heteroaromatic ring system having 5 to 30 aromatic ring atoms, which may be substituted by one or more radicals R;

$Ar^2$, $Ar^3$ is, identically or differently on each occurrence, together with the carbon atoms explicitly depicted, an aromatic or heteroaromatic ring system having 5 to 30 aromatic ring atoms, which may be substituted by one or more radicals R;

R is selected on each occurrence, identically or differently, from the group consisting of H, D, F, Cl, Br, I, CN, $NO_2$, $N(Ar^4)_2$, $N(R^1)_2$, C(═O)$Ar^4$, C(═O)$R^1$, P(═O)$(Ar^4)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may be replaced by $R^1C$═$CR^1$, C≡C, $Si(R^1)_2$, $Ge(R^1)_2$, $Sn(R^1)_2$, C═O, C═S, C═Se, C═$NR^1$, P(═O)(R'), SO, $SO_2$, $NR^1$, O, S or $CONR^1$ and where one or more H atoms may be replaced by D, F, Cl, Br, I, CN or $NO_2$, an aromatic or heteroaromatic ring system having 5 to 80, preferably 5 to 60, aromatic ring atoms, which may in each case be substituted by one or more radicals $R^1$, an aryloxy or heteroaryloxy group having 5 to 60 aromatic ring atoms, which may be substituted by one or more radicals $R^1$, or a combination of these systems, where two or more adjacent substituents R may optionally form a monocyclic or polycyclic, aliphatic, aromatic or heteroaromatic ring system, which may be substituted by one or more radicals $R^1$;

$R^1$ is selected on each occurrence, identically or differently, from the group consisting of H, D, F, Cl, Br, I, CN, $NO_2$, $N(Ar^4)_2$, $N(R^2)_2$, $C(=O)Ar^4$, $C(=O)R^2$, $P(=O)(Ar^4)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^2$, an aryloxy or heteroaryloxy group having 5 to 60 aromatic ring atoms, which may be substituted by one or more radicals $R^2$, or a combination of these systems, where two or more adjacent substituents R may optionally form a monocyclic or polycyclic, aliphatic, aromatic or heteroaromatic ring system, which may be substituted by one or more radicals $R^2$;

$Ar^4$ is on each occurrence, identically or differently, an aromatic or heteroaromatic ring system having 5-30 aromatic ring atoms, which may be substituted by one or more non-aromatic radicals $R^2$; two radicals $Ar^4$ here which are bonded to the same N atom or P atom may also be bridged to one another by a single bond or a bridge selected from $N(R^2)$, $C(R^2)_2$ or O;

$R^2$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^2$ may form a mono- or polycyclic, aliphatic, aromatic or heteroaromatic ring system with one another.

An electronic device in the sense of the present invention is a device which comprises at least one layer which comprises at least one organic compound. However, the component here may also comprise inorganic materials or also layers which are built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells (O-DSSCs), organic optical detectors, organic photoreceptors, organic field-quench devices (O-FQDs), light-emitting electrochemical cells (LECs), organic laser diodes (O-lasers) and organic plasmon emitting devices (D. M. Koller et al., *Nature Photonics* 2008, 1-4), but preferably organic electroluminescent devices (OLEDs), particularly preferably phosphorescent OLEDs.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (anellated) aryl or heteroaryl group, for example naphthalene, anthracene, phenanthrene, quinoline, isoquinoline, etc. Aromatic groups which are linked to one another by a single bond, such as, for example, biphenyl, are, by contrast, not referred to as aryl or heteroaryl group, but instead as aromatic ring system.

An aromatic ring system in the sense of this invention contains 6 to 80 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be connected by a non-aromatic unit, such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are connected, for example, by a short alkyl group.

For the purposes of the present invention, an aliphatic hydrocarbon radical or an alkyl group or an alkenyl or alkynyl group, which may contain 1 to 40 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5-80 aromatic ring atoms, which may also in each case be substituted by the above-mentioned radicals $R^2$ or a hydrocarbon radical and which may be linked via any desired positions on the aromatic or heteroaromatic ring system, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combination of these systems.

In a preferred embodiment of the invention, X stands for C═O, $CR_2$, $SiR_2$, P(═O)R or $SO_2$, particularly preferably for C═O, $SiR_2$ or $SO_2$.

In a further preferred embodiment of the invention, E stands for a single bond, $CR_2$, C═O, NR, O or S, particularly preferably for a single bond, $CR_2$, C═O or NR, very particularly preferably for a single bond, $CR_2$ or C═O, in particular for a single bond.

In a further preferred embodiment of the invention, the group $Ar^1$ stands for a group of the following formula (2), (3), (4), (5) or (6), formula (2)

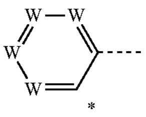

formula (3)

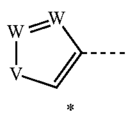

formula (4)

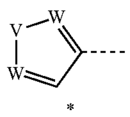

formula (5)

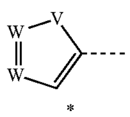

-continued formula (6)

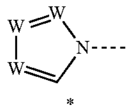

where the dashed bond indicates the link to X, * indicates the position of the link to $Ar^2$, and furthermore:

W is, identically or differently on each occurrence, CR or N; or two adjacent groups W stand for a group of the following formula (7) or (8), formula (7)

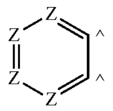

formula (8)

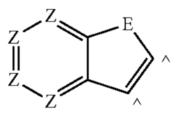

where E has the above-mentioned meaning, but preferably does not represent a single bond, Z stands, identically or differently on each occurrence, for CR or N and ^ indicate the corresponding adjacent groups W in the formula (2) to (6);

V is NR, O or S.

In a further preferred embodiment of the invention, the group $Ar^2$ stands for a group of one of the following formulae (9), (10) or (11), formula (9)

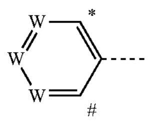

formula (10)

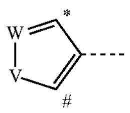

formula (11)

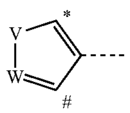

where the dashed bond indicates the link to N, # indicates the position of the link to E, * indicates the link to $Ar^1$ and W and V have the above-mentioned meanings.

In a further preferred embodiment of the invention, the group $Ar^3$ stands for a group of one of the following formulae (12), (13), (14) or (15), formula (12)

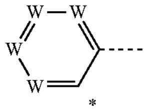

formula (13)

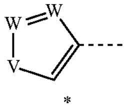

formula (14)

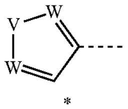

formula (15)

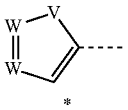

where the dashed bond indicates the link to N, * indicates the link to E and W and V have the above-mentioned meanings.

In a particularly preferred embodiment of the invention, the above-mentioned preferences occur simultaneously. Particular preference is therefore given to compounds of the formula (1) for which:

X is C═O, $CR_2$, $SiR_2$, P(═O)R or $SO_2$;

E is, identically or differently on each occurrence, a single bond, $CR_2$, C═O, NR, O or S;

$Ar^1$ is selected from the groups of the above-mentioned formulae (2), (3), (4), (5) or (6);

$Ar^2$ is selected from the groups of the above-mentioned formulae (9), (10) or (11);

$Ar^3$ is selected from the groups of the above-mentioned formulae (12), (13), (14) or (15).

In a very particularly preferred embodiment of the invention, the following applies to compounds of the formula (1):

X is C═O, $SiR_2$ or $SO_2$;

E is, identically or differently on each occurrence, a single bond, $CR_2$, C═O or NR, preferably a single bond, $CR_2$ or C═O, particularly preferably a single bond;

$Ar^1$ is selected from the groups of the above-mentioned formulae (2), (3), (4), (5) or (6);

$Ar^2$ is selected from the groups of the above-mentioned formulae (9), (10) or (11);

$Ar^3$ is selected from the groups of the above-mentioned formulae (12), (13), (14) or (15).

The above-mentioned preferred groups $Ar^1$, $Ar^2$ and $Ar^3$ may be combined with one another as desired here. Suitable combinations are thus the following:

| $Ar^1$ | $Ar^2$ | $Ar^3$ |
|---|---|---|
| formula (2) | formula (9) | formula (12) |
| formula (2) | formula (9) | formula (13) |
| formula (2) | formula (9) | formula (14) |
| formula (2) | formula (9) | formula (15) |
| formula (2) | formula (10) | formula (12) |
| formula (2) | formula (10) | formula (13) |
| formula (2) | formula (10) | formula (14) |
| formula (2) | formula (10) | formula (15) |
| formula (2) | formula (11) | formula (12) |

-continued

| $Ar^1$ | $Ar^2$ | $Ar^3$ |
|---|---|---|
| formula (2) | formula (11) | formula (13) |
| formula (2) | formula (11) | formula (14) |
| formula (2) | formula (11) | formula (15) |
| formula (2) | formula (12) | formula (12) |
| formula (2) | formula (12) | formula (13) |
| formula (2) | formula (12) | formula (14) |
| formula (2) | formula (12) | formula (15) |
| formula (3) | formula (9) | formula (12) |
| formula (3) | formula (9) | formula (13) |
| formula (3) | formula (9) | formula (14) |
| formula (3) | formula (9) | formula (15) |
| formula (3) | formula (10) | formula (12) |
| formula (3) | formula (10) | formula (13) |
| formula (3) | formula (10) | formula (14) |
| formula (3) | formula (10) | formula (15) |
| formula (3) | formula (11) | formula (12) |
| formula (3) | formula (11) | formula (13) |
| formula (3) | formula (11) | formula (14) |
| formula (3) | formula (11) | formula (15) |
| formula (3) | formula (12) | formula (12) |
| formula (3) | formula (12) | formula (13) |
| formula (3) | formula (12) | formula (14) |
| formula (3) | formula (12) | formula (15) |
| formula (4) | formula (9) | formula (12) |
| formula (4) | formula (9) | formula (13) |
| formula (4) | formula (9) | formula (14) |
| formula (4) | formula (9) | formula (15) |
| formula (4) | formula (10) | formula (12) |
| formula (4) | formula (10) | formula (13) |
| formula (4) | formula (10) | formula (14) |
| formula (4) | formula (10) | formula (15) |
| formula (4) | formula (11) | formula (12) |
| formula (4) | formula (11) | formula (13) |
| formula (4) | formula (11) | formula (14) |
| formula (4) | formula (11) | formula (15) |
| formula (4) | formula (12) | formula (12) |
| formula (4) | formula (12) | formula (13) |
| formula (4) | formula (12) | formula (14) |
| formula (4) | formula (12) | formula (15) |
| formula (5) | formula (9) | formula (12) |
| formula (5) | formula (9) | formula (13) |
| formula (5) | formula (9) | formula (14) |
| formula (5) | formula (9) | formula (15) |
| formula (5) | formula (10) | formula (12) |
| formula (5) | formula (10) | formula (13) |
| formula (5) | formula (10) | formula (14) |
| formula (5) | formula (10) | formula (15) |
| formula (5) | formula (11) | formula (12) |
| formula (5) | formula (11) | formula (13) |
| formula (5) | formula (11) | formula (14) |
| formula (5) | formula (11) | formula (15) |
| formula (5) | formula (12) | formula (12) |
| formula (5) | formula (12) | formula (13) |
| formula (5) | formula (12) | formula (14) |
| formula (5) | formula (12) | formula (15) |
| formula (6) | formula (9) | formula (12) |
| formula (6) | formula (9) | formula (13) |
| formula (6) | formula (9) | formula (14) |
| formula (6) | formula (9) | formula (15) |
| formula (6) | formula (10) | formula (12) |
| formula (6) | formula (10) | formula (13) |
| formula (6) | formula (10) | formula (14) |
| formula (6) | formula (10) | formula (15) |
| formula (6) | formula (11) | formula (12) |
| formula (6) | formula (11) | formula (13) |
| formula (6) | formula (11) | formula (14) |
| formula (6) | formula (11) | formula (15) |
| formula (6) | formula (12) | formula (12) |
| formula (6) | formula (12) | formula (13) |
| formula (6) | formula (12) | formula (14) |
| formula (6) | formula (12) | formula (15) |

Particularly preferably, at least two of the groups $Ar^1$, $Ar^2$ and $Ar^3$ stand for a 6-membered aryl or 6-membered heteroaryl ring group. Particularly preferably, $Ar^1$ thus stands for a group of the formula (2) and at the same time $Ar^2$ stands for a group of the formula (9), or $Ar^1$ stands for a group of the formula (2) and at the same time $Ar^3$ stands for a group of the formula (12), or $Ar^2$ stands for a group of the formula (9) and at the same time $Ar^3$ stands for a group of the formula (12).

Particularly preferred embodiments of the invention are therefore the compounds of the following formulae (16) to (25), formula (16)

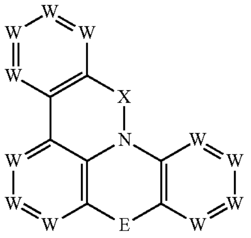

formula (17)

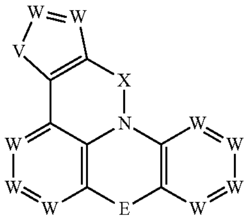

formula (18)

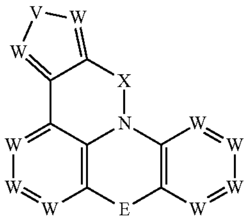

formula (19)

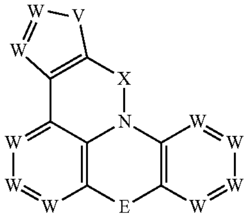

formula (20)

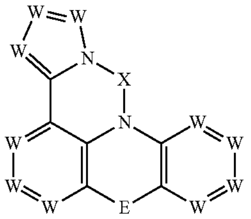

formula (21)

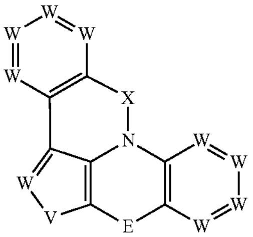

-continued formula (22)

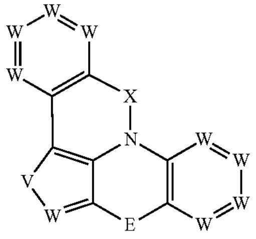

formula (23)

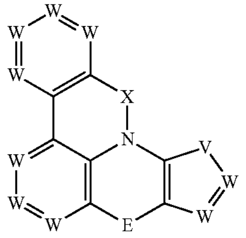

formula (24)

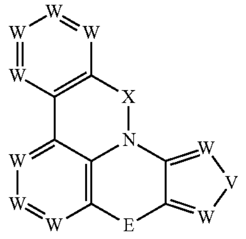

formula (25)

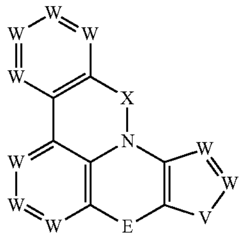

where the symbols used have the above-mentioned meanings.

As already stated above, two adjacent groups W may also stand for a group of the above-mentioned formula (7) or (8). If two adjacent groups W stand for a group of the above-mentioned formula (7), structures are obtained as depicted by way of example by the following formulae (26) to (31). These structures of the formulae (26) to (30) are derived from the above-mentioned formula (16) and the structure of the formula (31) is derived from the above-mentioned formula (25). Further corresponding structures of the above-mentioned formulae (17) to (25) can be derived entirely analogously.

formula (26)

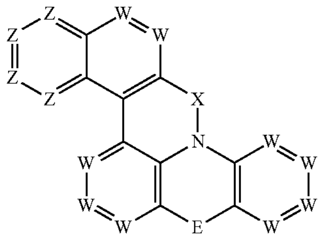

-continued formula (27)

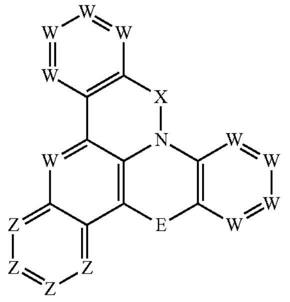

formula (28)

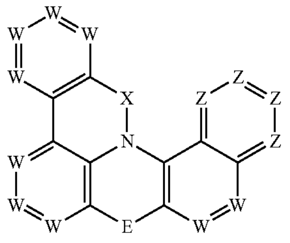

formula (29)

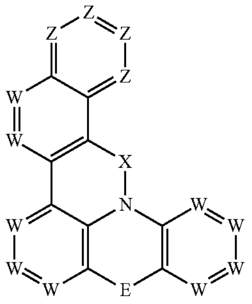

formula (30)

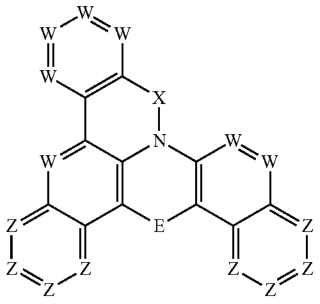

formula (31)

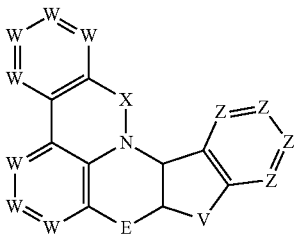

The symbols used have the above-mentioned meanings.

If two adjacent groups W stand for a group of the above-mentioned formula (8), structures are obtained as depicted by way of example by the following formulae (32) to (37). These structures are derived from the above-mentioned formula (16). Corresponding structures of the above-mentioned formulae (17) to (25) can be derived entirely analogously.

formula (32)

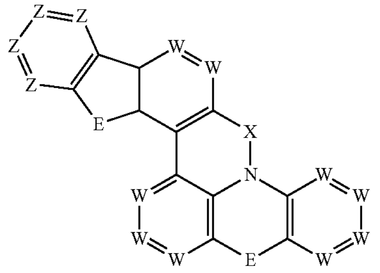

formula (33)

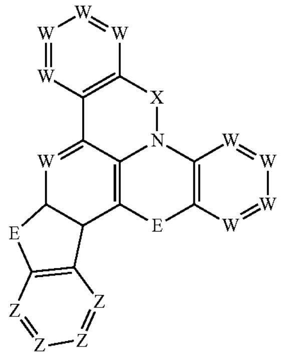

formula (34)

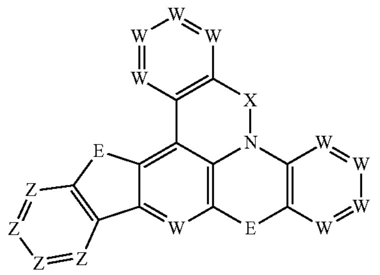

formula (35)

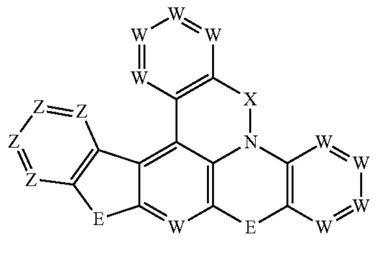

formula (36)

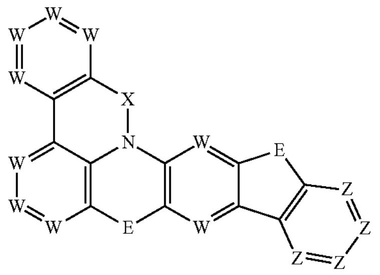

-continued formula (37)

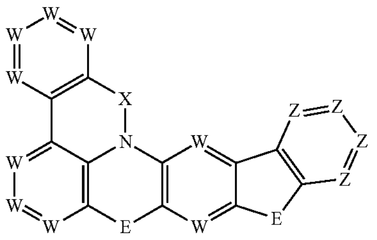

The symbols used have the above-mentioned meanings.

In a further preferred embodiment of the compounds of the formula (16) to (25), in total a maximum of one symbol W per ring stands for N, and the remaining symbols W which do not stand for a group of the formula (7) or (8) stand for CR. In a particularly preferred embodiment of the invention, all symbols W which do not stand for a group of the formula (7) or (8) stand for CR. Particular preference is therefore given to the compounds of the following formulae (16a) to (25a), formula (16a)

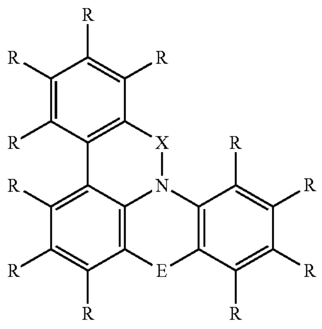

formula (17a)

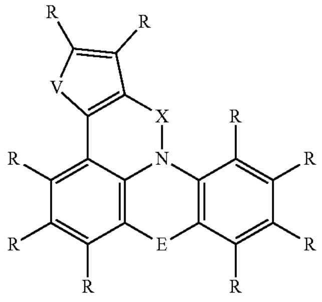

formula (18a)

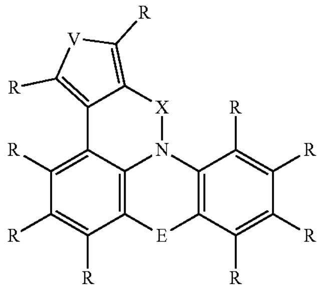

-continued formula (19a)

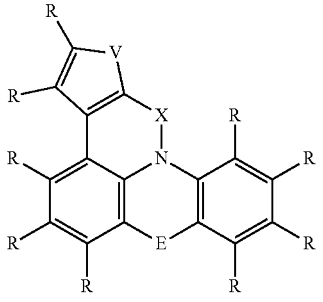

formula (20a)

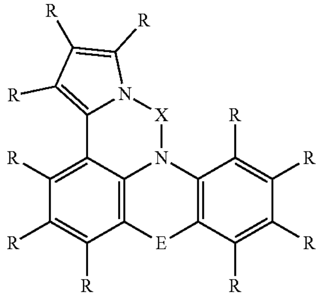

formula (21a)

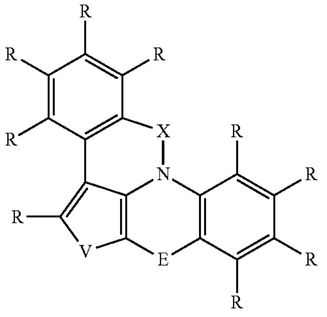

formula (22a)

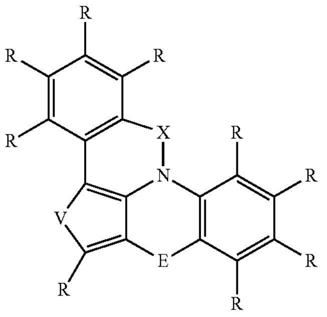

formula (23a)

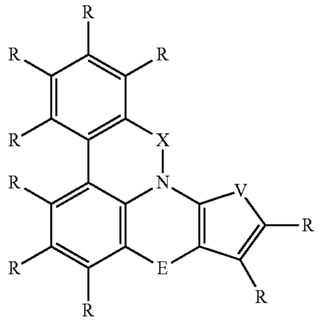

-continued
formula (24a)
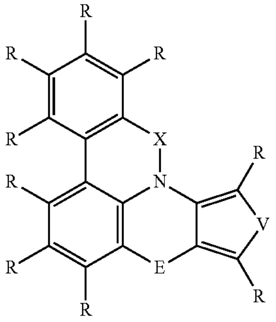
formula (25a)
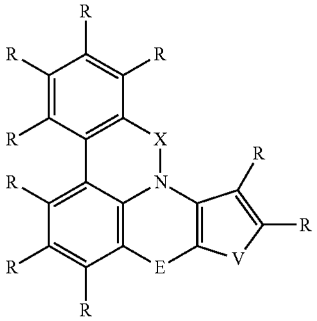
where the symbols used have the above-mentioned meanings.
Very particular preference is given to the compounds of the following formulae (16b) to (25b),
formula (16b)
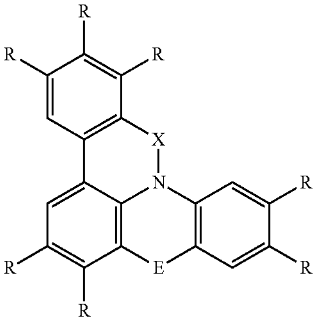
formula (17b)
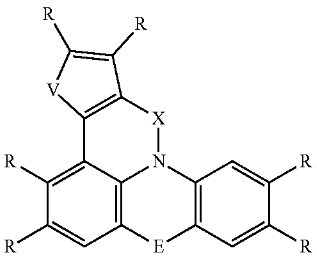
-continued
formula (18b)
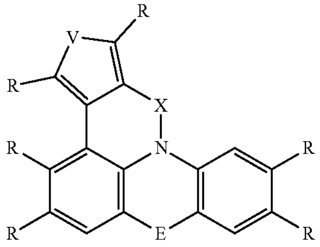
formula (19b)
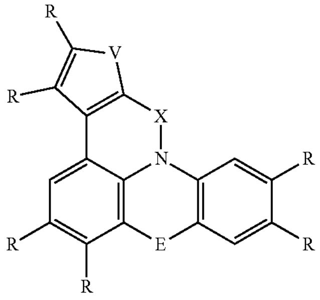
formula (20b)
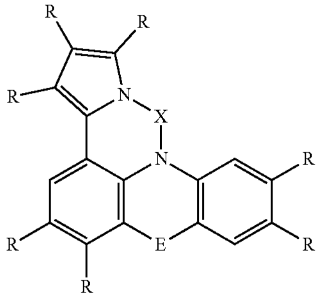
formula (21b)
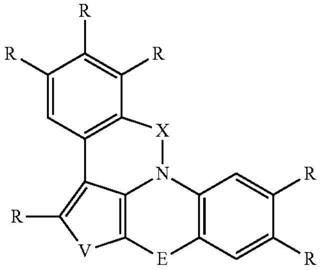
formula (22b)
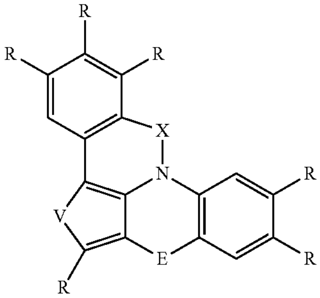

-continued
formuls (23b)
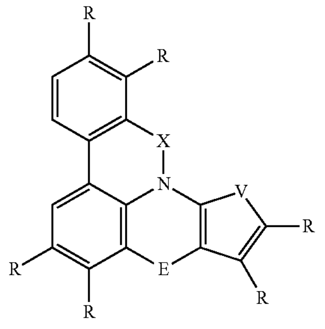
formula (24b)
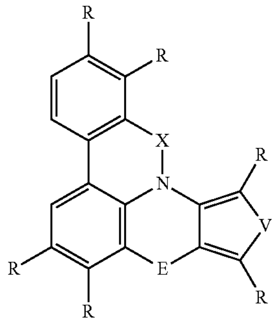
formula (25b)
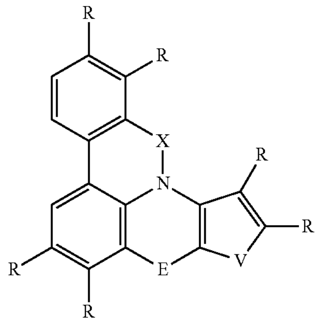
where the symbols used have the above-mentioned meanings.
Especial preference is given to the structures of the formulae (16c) to (25c),
formula (16c)
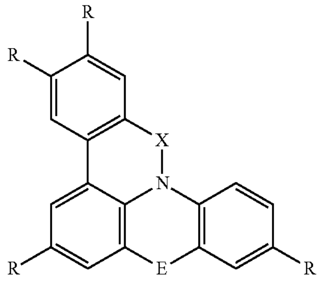
-continued
formula (17c)
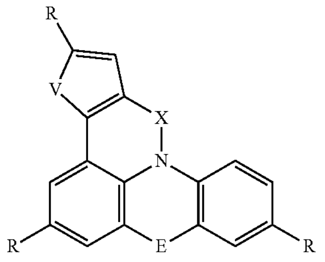
formula (18c)
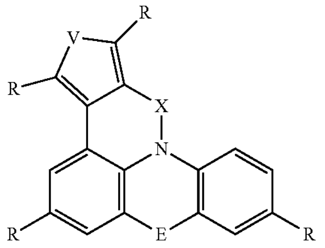
formula (19c)
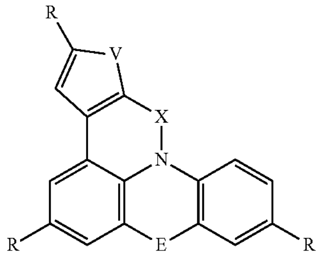
formula (20c)
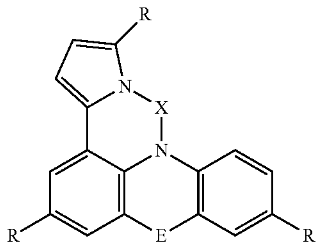
formula (21c)
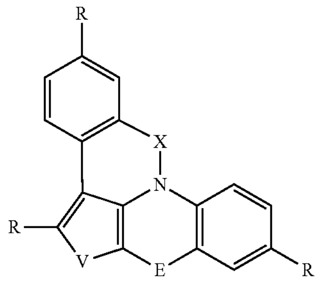
formula (22c)
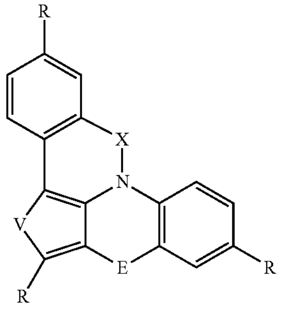

-continued formula (23c)

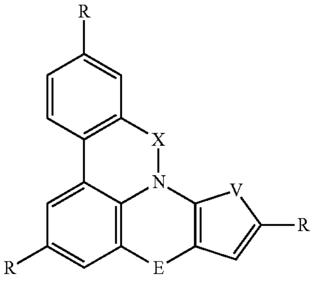

formula (24c)

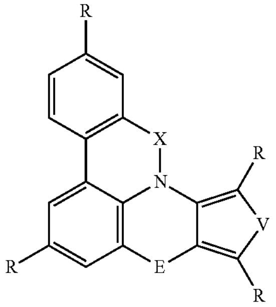

formula (25c)

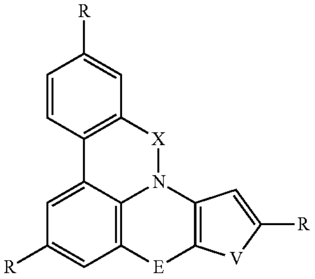

where the symbols used have the above-mentioned meanings.

X in the formulae (16) to (25), (16a) to (25a), (16b) to (25b) and (16c) to (25c) preferably stands for C=O, $CR_2$, $SiR_2$ or $SO_2$.

Furthermore, E in the formulae (16) to (25), (16a) to (25a), (16b) to (25b) and (16c) to (25c) preferably stands for a single bond, $CR_2$, NR, O or S.

Particularly preferably, X in the formulae (16) to (25), (16a) to (25a), (16b) to (25b) and (16c) to (25c) stands for C=O, $CR_2$, $SiR_2$ or $SO_2$ and at the same time E stands for a single bond, $CR_2$, NR, O or S.

Particularly preferred combinations of the symbols X, E and V in the compounds of the formulae (16) to (25), (16a) to (25a), (16b) to (25b) and (16c) to (25c) are therefore the following combinations:

| X | E | V |
|---|---|---|
| C=O | single bond | N—R |
| C=O | single bond | O |
| C=O | single bond | S |
| C=O | $CR_2$ | N—R |
| C=O | $CR_2$ | O |
| C=O | $CR_2$ | S |
| C=O | C=O | N—R |
| C=O | C=O | O |
| C=O | C=O | S |
| C=O | N—R | N—R |
| C=O | N—R | O |
| C=O | N—R | S |

-continued

| X | E | V |
|---|---|---|
| $CR_2$ | single bond | N—R |
| $CR_2$ | single bond | O |
| $CR_2$ | single bond | S |
| $CR_2$ | $CR_2$ | N—R |
| $CR_2$ | $CR_2$ | O |
| $CR_2$ | $CR_2$ | S |
| $CR_2$ | C=O | N—R |
| $CR_2$ | C=O | O |
| $CR_2$ | C=O | S |
| $CR_2$ | N—R | N—R |
| $CR_2$ | N—R | O |
| $CR_2$ | N—R | S |
| $SiR_2$ | single bond | N—R |
| $SiR_2$ | single bond | O |
| $SiR_2$ | single bond | S |
| $SiR_2$ | $CR_2$ | N—R |
| $SiR_2$ | $CR_2$ | O |
| $SiR_2$ | $CR_2$ | S |
| $SiR_2$ | C=O | N—R |
| $SiR_2$ | C=O | O |
| $SiR_2$ | C=O | S |
| $SiR_2$ | N—R | N—R |
| $SiR_2$ | N—R | O |
| $SiR_2$ | N—R | S |
| $SO_2$ | single bond | N—R |
| $SO_2$ | single bond | O |
| $SO_2$ | single bond | S |
| $SO_2$ | $CR_2$ | N—R |
| $SO_2$ | $CR_2$ | O |
| $SO_2$ | $CR_2$ | S |
| $SO_2$ | C=O | N—R |
| $SO_2$ | C=O | O |
| $SO_2$ | C=O | S |
| $SO_2$ | N—R | N—R |
| $SO_2$ | N—R | O |
| $SO_2$ | N—R | S |

It is furthermore preferred, if two adjacent groups W stand for a group of the formula (7) or (8), for a maximum of one group Z to stand for N. Particularly preferably, all groups Z stand for CR. It is furthermore preferred, if two adjacent groups W stand for a group of the formula (8), for E in the group of the formula (8) to stand for $CR_2$, C=O or NR.

In a preferred embodiment of the invention, R in the above-mentioned formulae is selected, identically or differently on each occurrence, from the group consisting of H, D, F, Cl, Br, CN, $N(Ar^1)_2$, $C(=O)Ar^1$, a straight-chain alkyl or alkoxy group having 1 to 10 C atoms or a branched or cyclic alkyl or alkoxy group having 3 to 10 C atoms or an alkenyl or alkynyl group having 2 to 10 C atoms, each of which may be substituted by one or more radicals $R^1$, where one or more non-adjacent $CH_2$ groups may be replaced by 0 and where one or more H atoms may be replaced by D or F, an aromatic or heteroaromatic ring system having 5 to 30 aromatic ring atoms, which may in each case be substituted by one or more radicals $R^1$, an aryloxy or heteroaryloxy group having 5 to 30 aromatic ring atoms, which may be substituted by one or more radicals $R^1$, or a combination of these systems.

In a particularly preferred embodiment of the invention, R in the above-mentioned formulae is selected, identically or differently on each occurrence, from the group consisting of H, D, F, Cl, Br, CN, a straight-chain alkyl group having 1 to 10 C atoms or a branched or cyclic alkyl group having 3 to 10 C atoms, each of which may be substituted by one or more radicals $R^1$, where one or more H atoms may be replaced by D or F, an aromatic or heteroaromatic ring system having 5 to 18 aromatic ring atoms, which may in each case be substituted by one or more radicals $R^1$, or a combination of these systems.

If the compounds of the formula (1) or the preferred embodiments are used as electron-transport material, it is preferred for the group X to stand for C═O or $SO_2$ and/or for at least one of the radicals R to stand for an aromatic ring system or an electron-deficient heteroaromatic ring system. Electron-deficient heterocycles are in accordance with the invention five-membered heterocyclic rings having at least two heteroatoms or six-membered heterocyclic rings, onto which in each case one or more aromatic or heteroaromatic groups may also be condensed.

If the compounds of the formula (1) or the preferred embodiments are used as matrix material for a phosphorescent emitter, it is preferred for the group X to stand for C═O and/or for at least one of the radicals R to stand for a substituted or unsubstituted carbazole, indenocarbazole or indolocarbazole, each of which may be bonded via a carbon atom or a nitrogen atom.

For compounds which are processed by vacuum evaporation, the alkyl groups preferably have not more than five C atoms, particularly preferably not more than 4 C atoms, very particularly preferably not more than 1 C atom. For compounds which are processed from solution, compounds which are substituted by alkyl groups having up to 10 C atoms or which are substituted by oligoarylene groups, for example ortho-, meta-, para- or branched terphenyl groups, are also suitable.

Examples of preferred compounds in accordance with the above-mentioned embodiments are the compounds of the following structures.

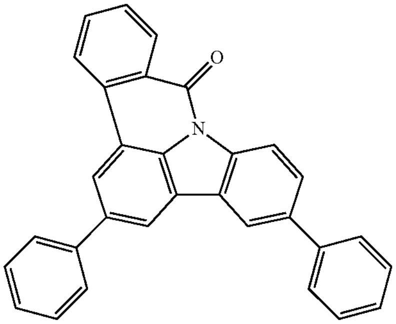

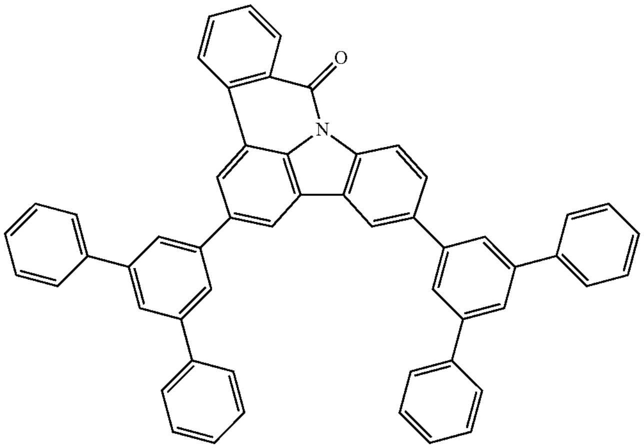

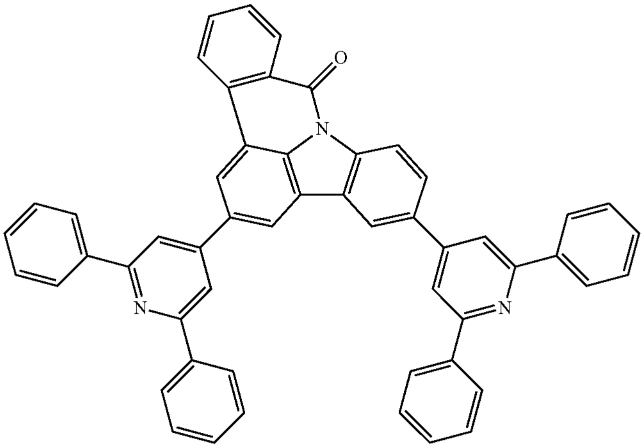

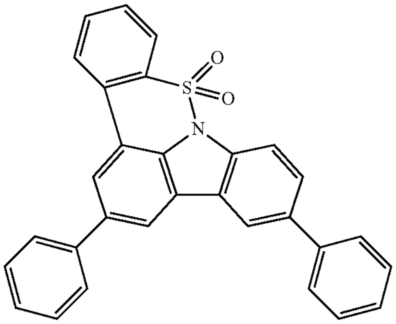

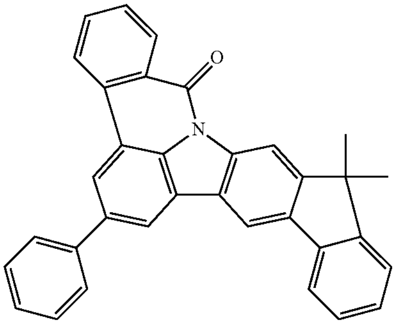

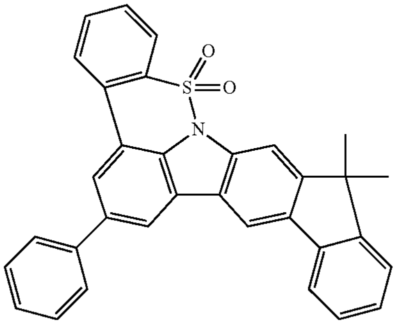

-continued
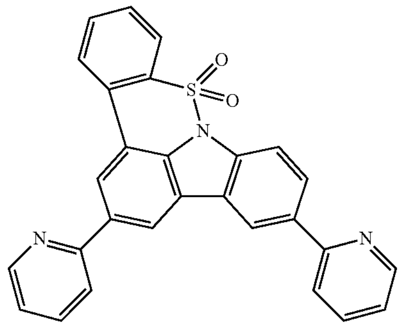
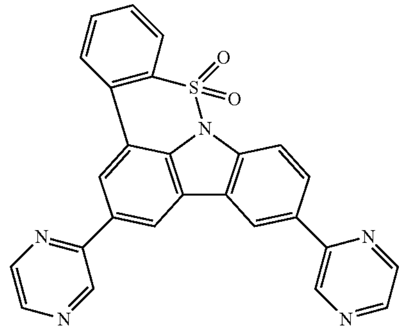
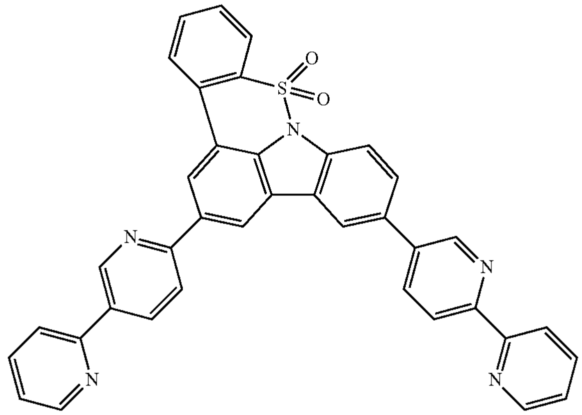
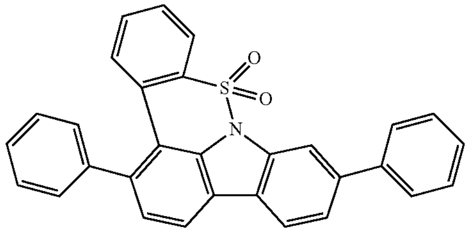
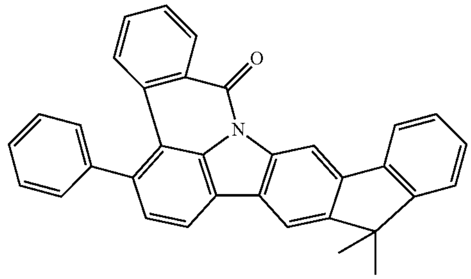
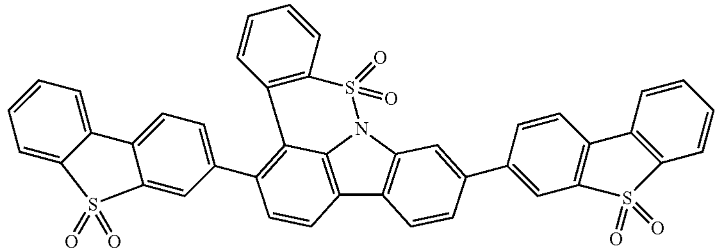
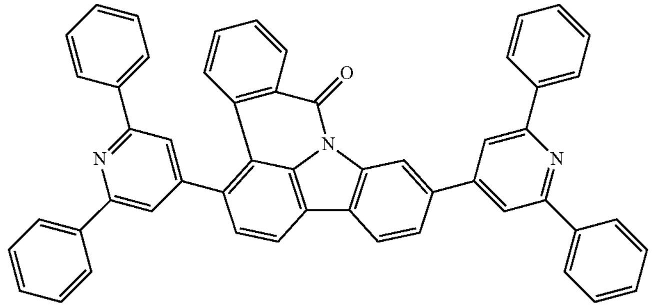
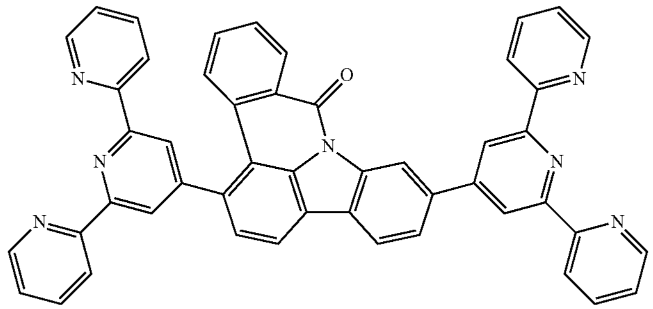

-continued
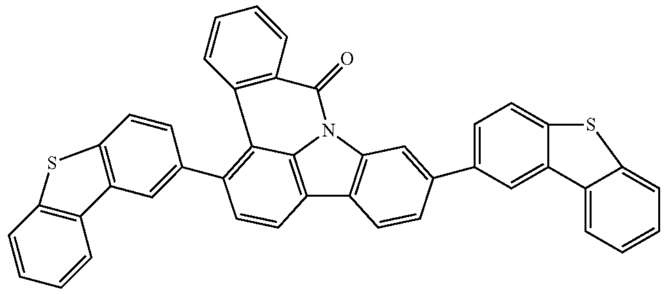
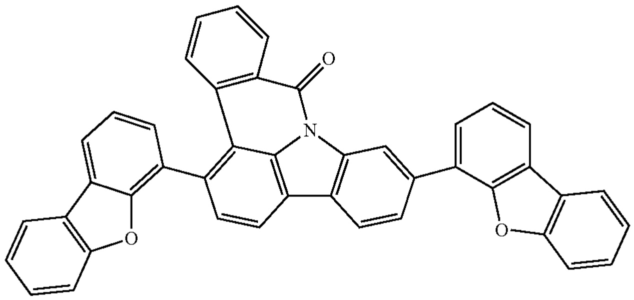
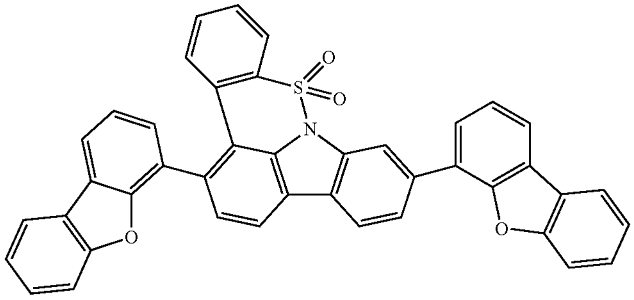
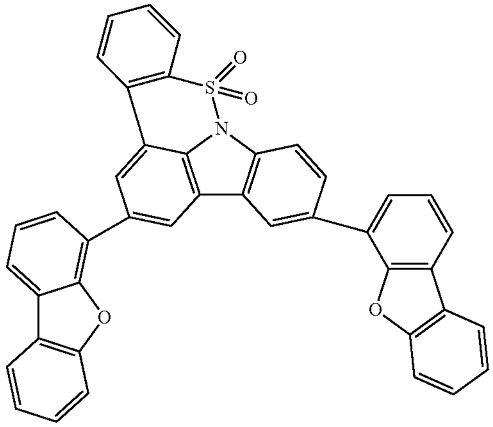
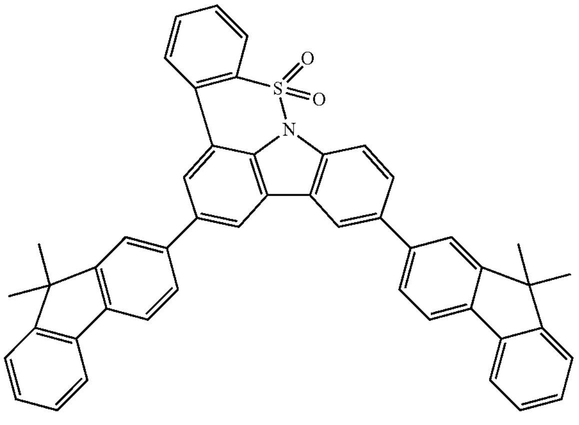
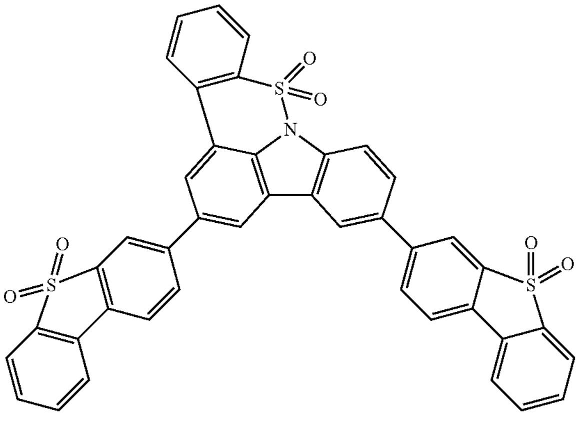

-continued
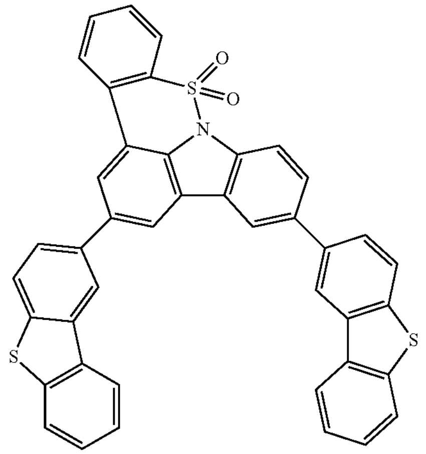
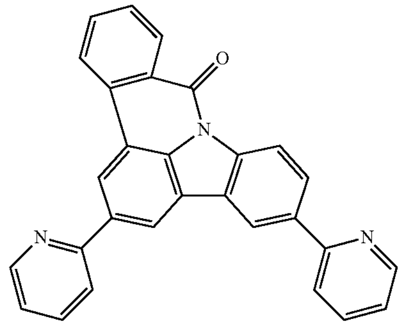
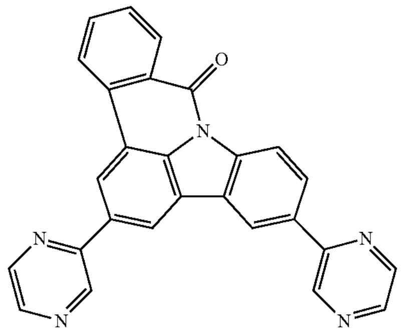
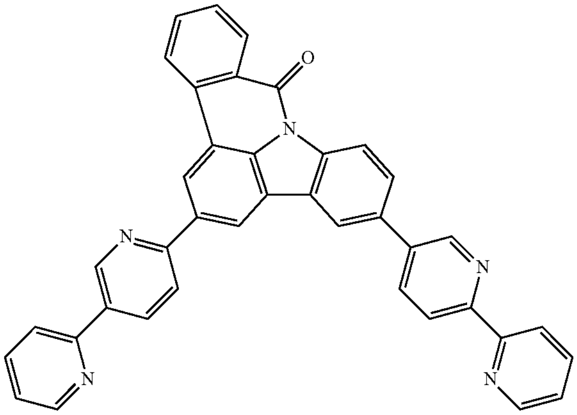
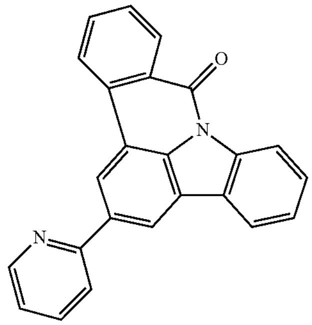
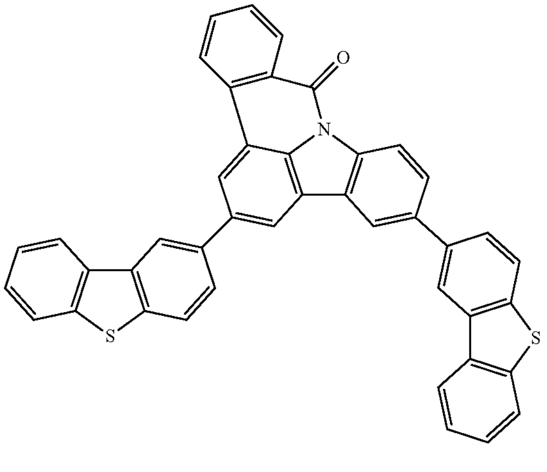

-continued
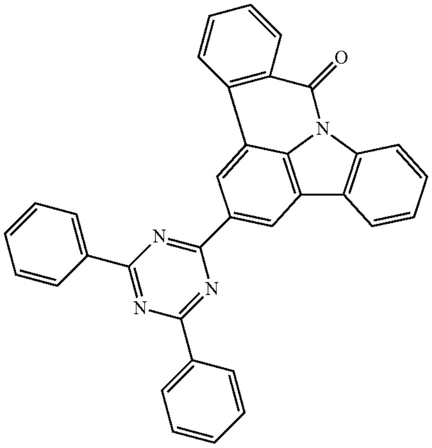
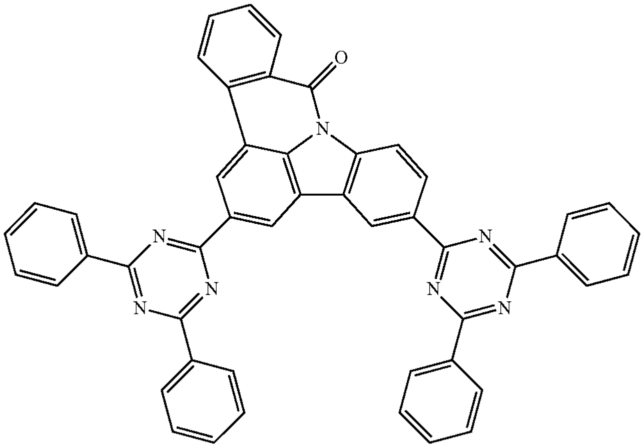
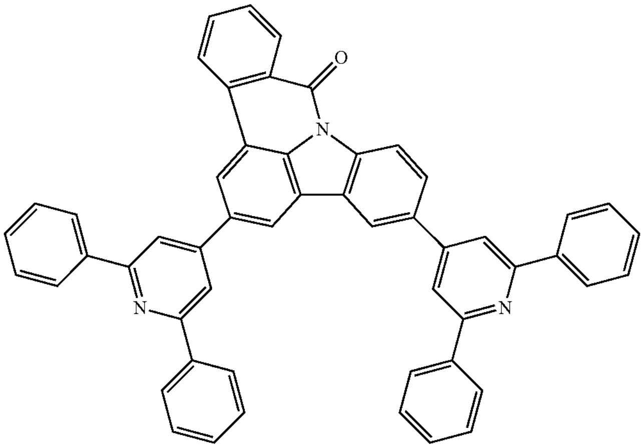
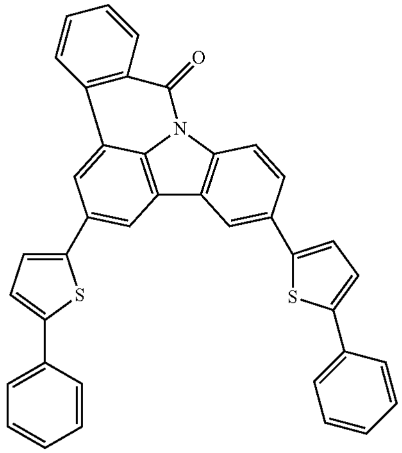
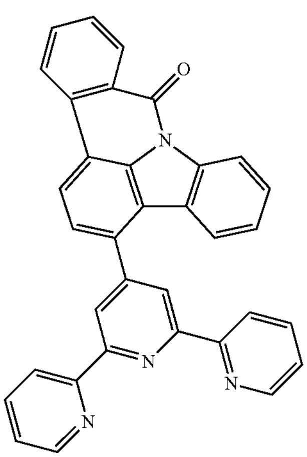
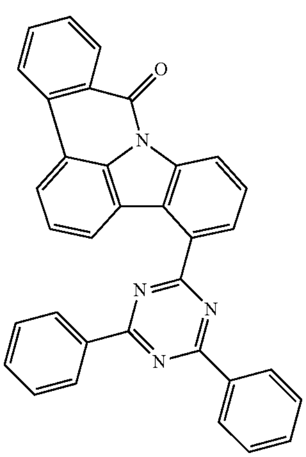
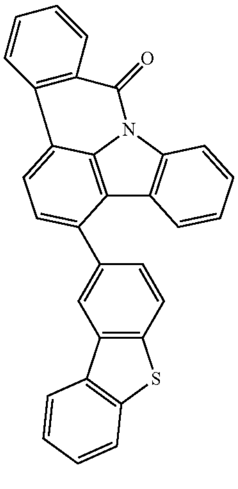
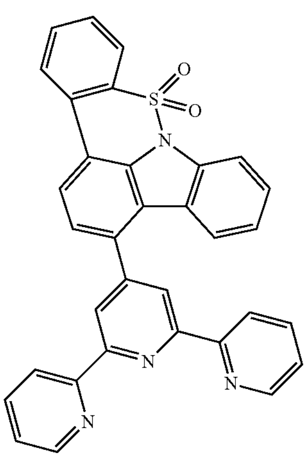

-continued
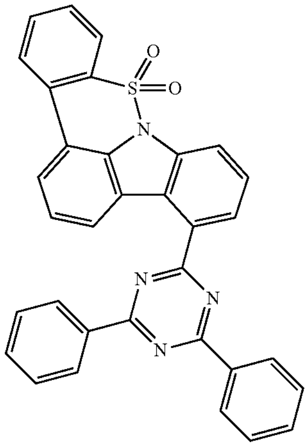
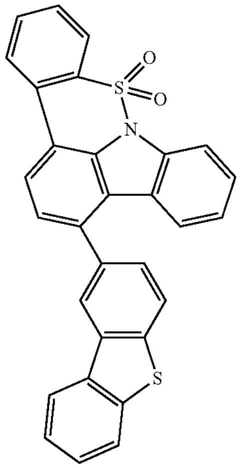
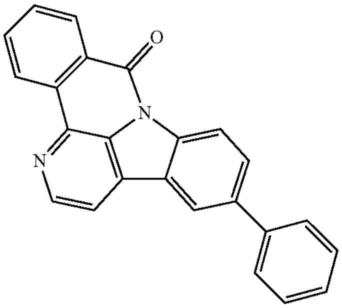
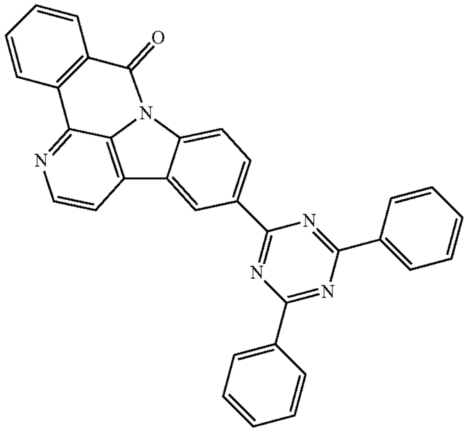
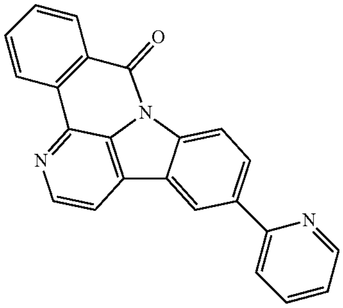
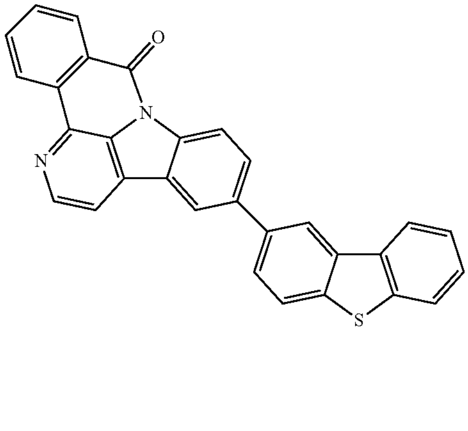
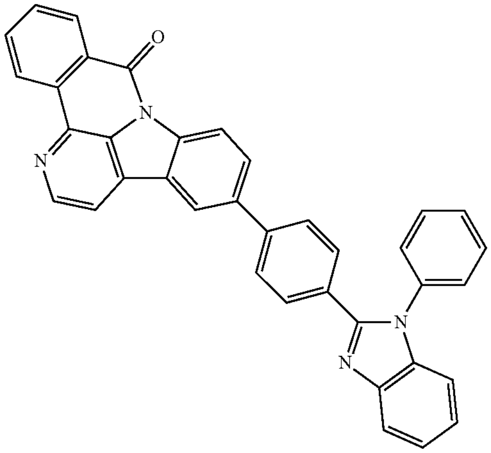

-continued
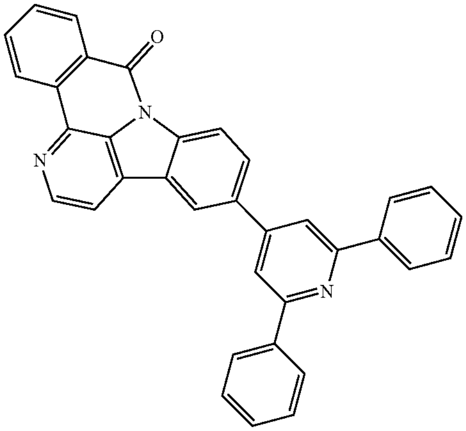
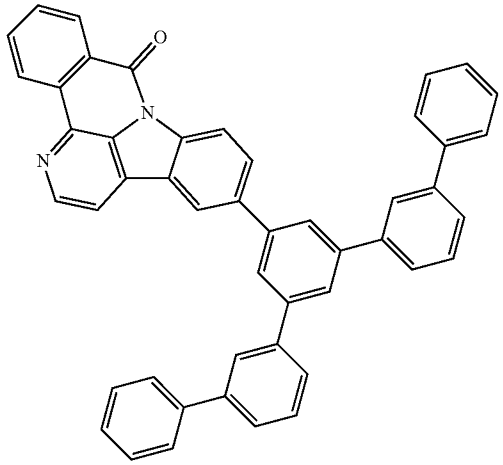
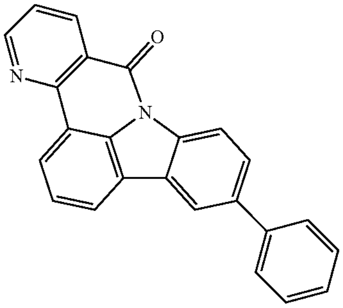
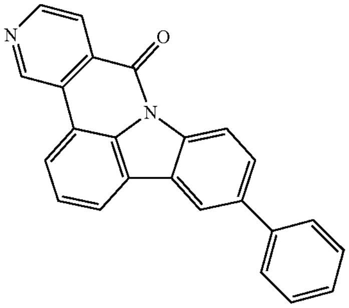
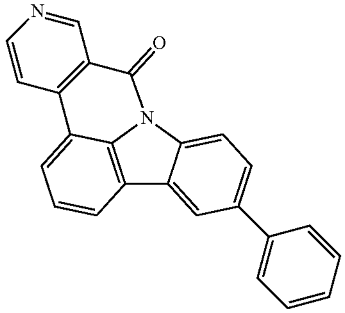
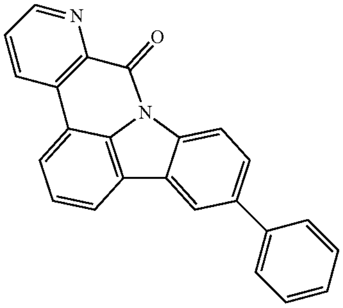
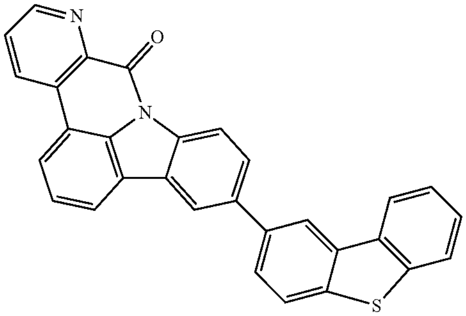
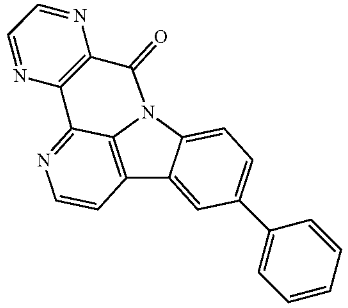
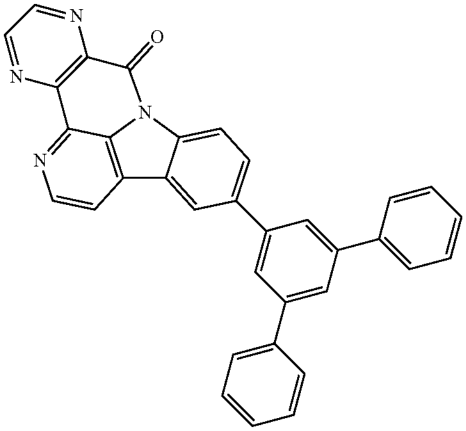
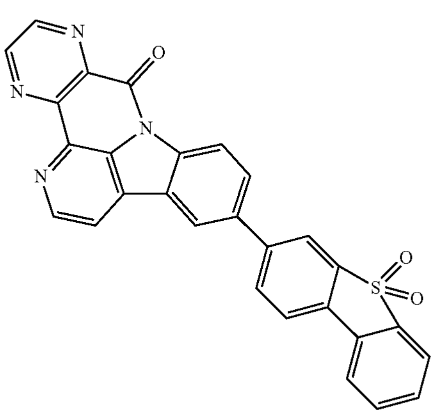

-continued
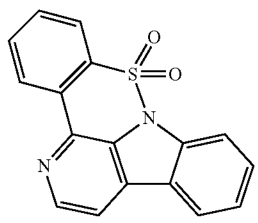
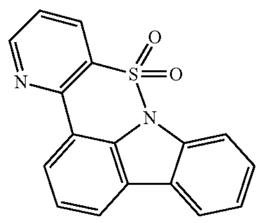
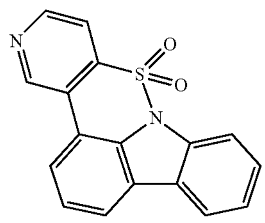
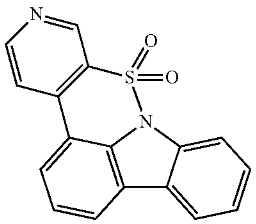
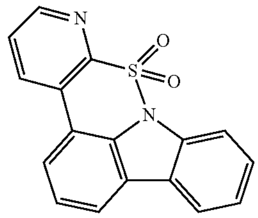
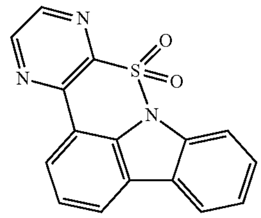
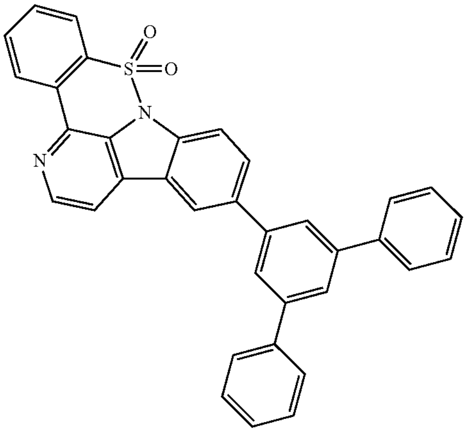
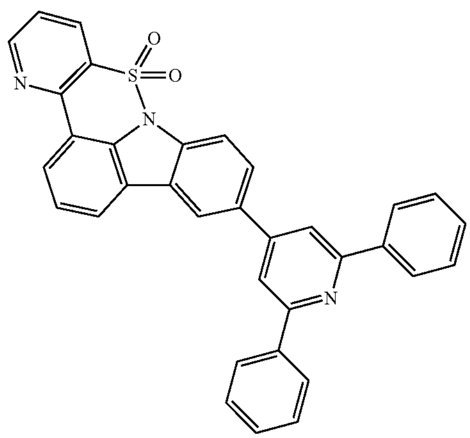
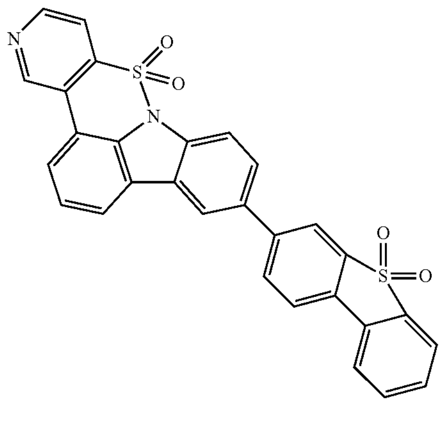
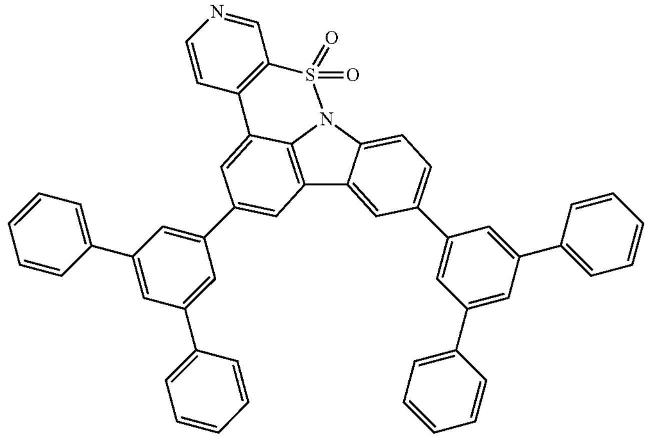
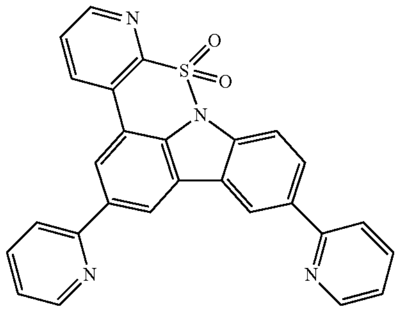

-continued
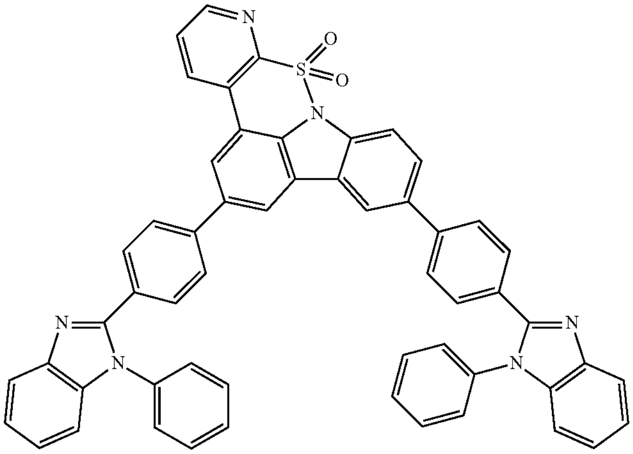
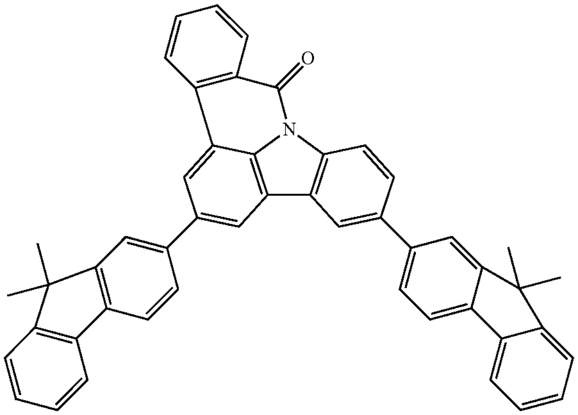
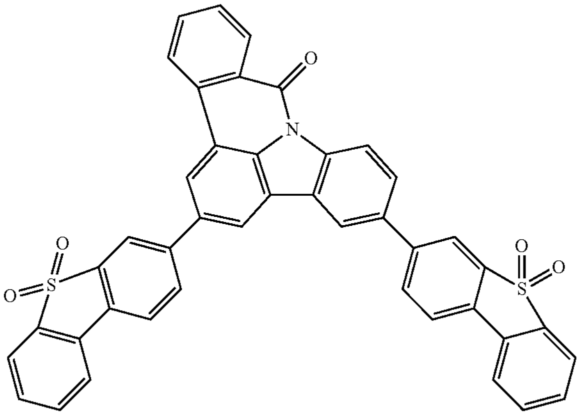
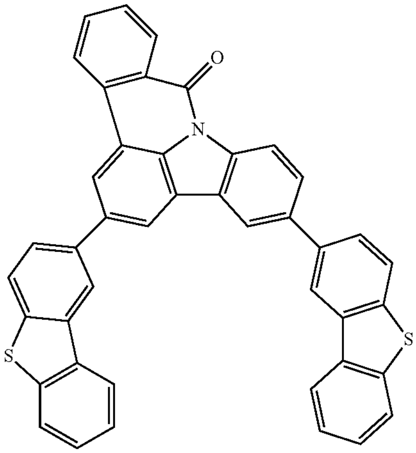
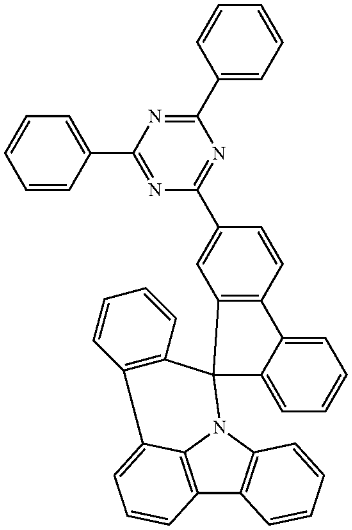
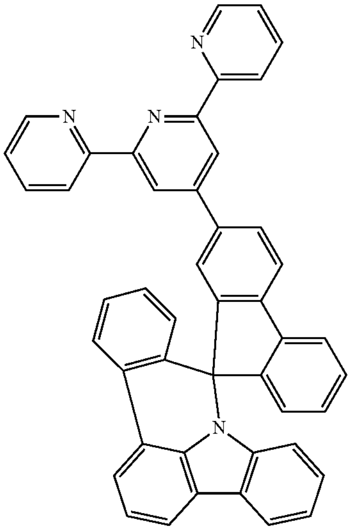

-continued
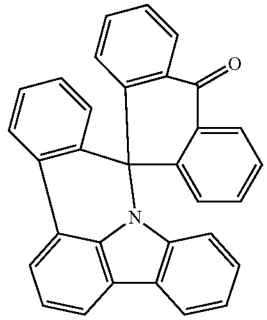
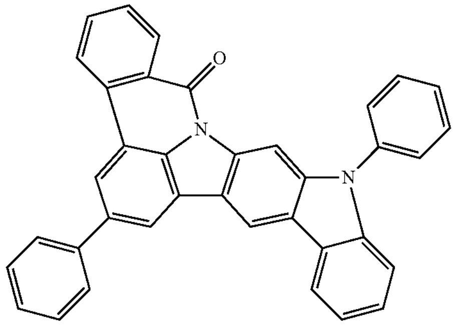
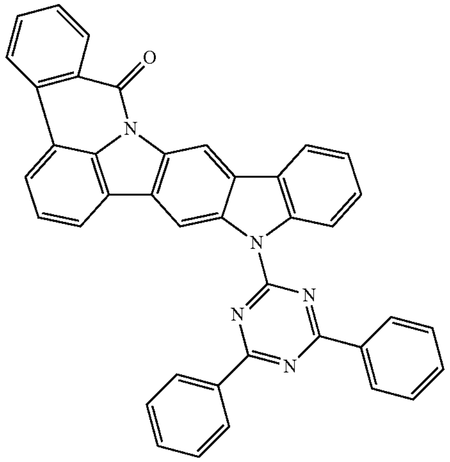
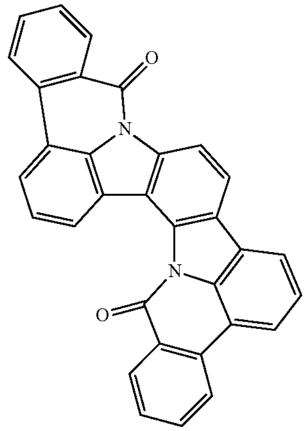
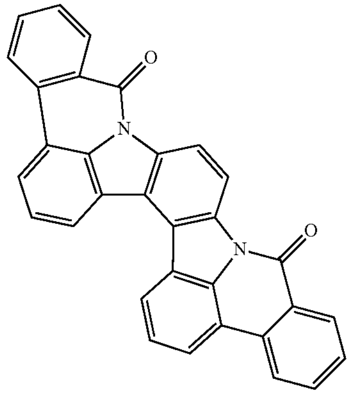
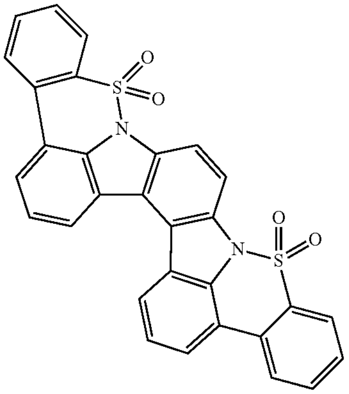
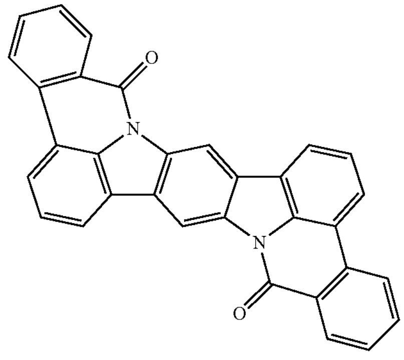
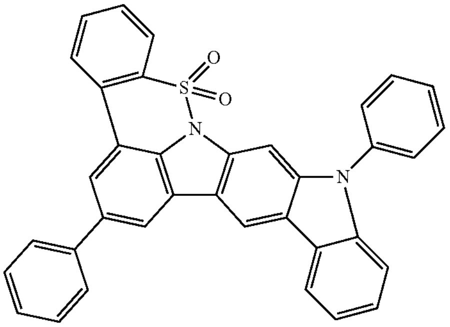
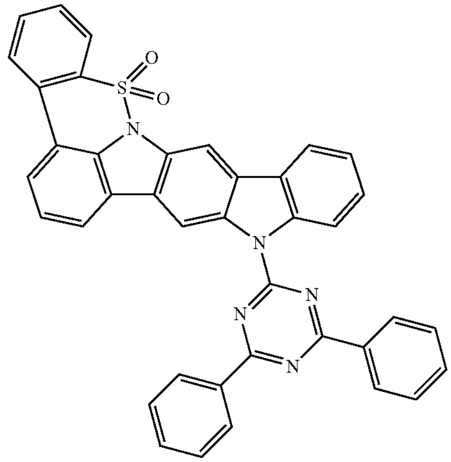
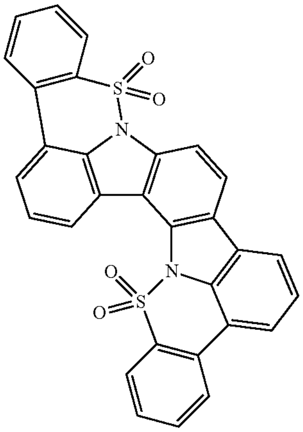

-continued
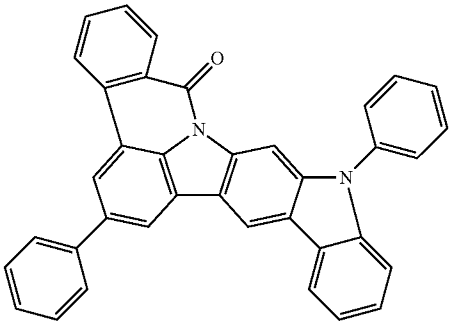
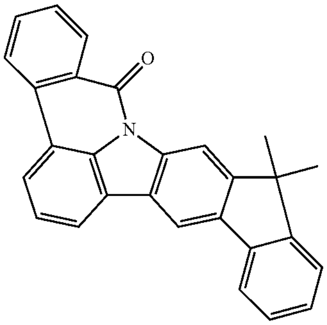
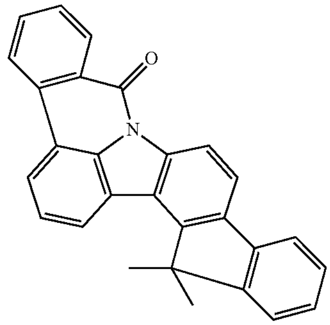
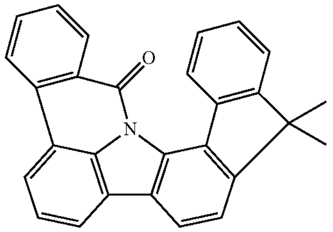
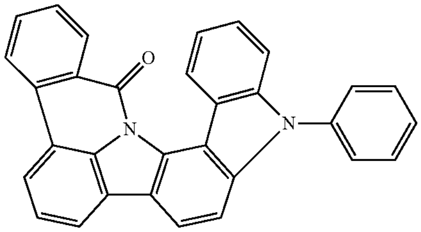
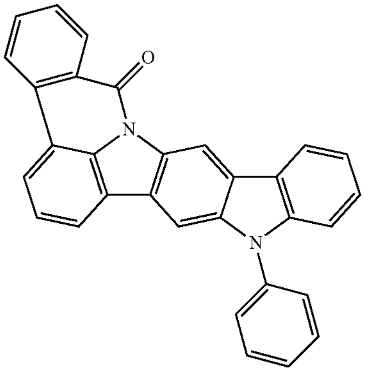
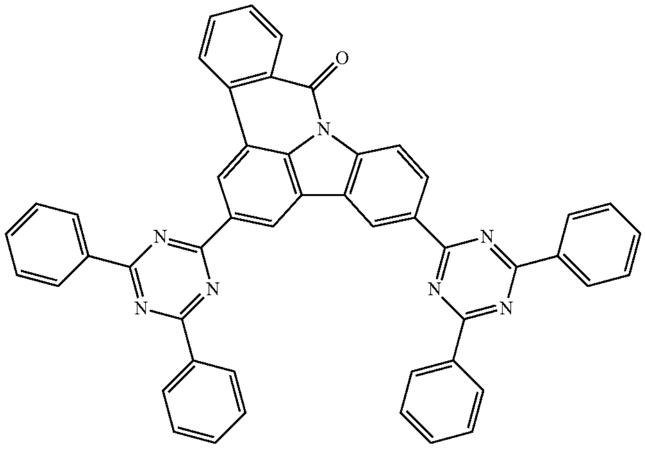
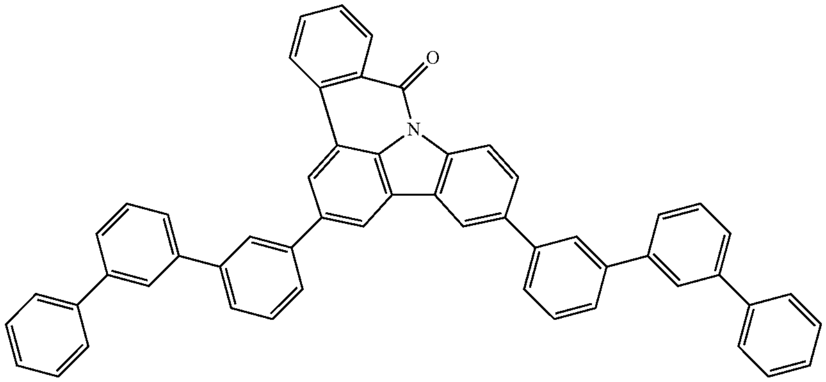

-continued
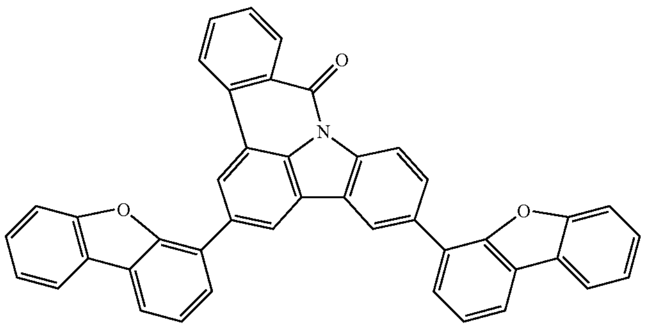
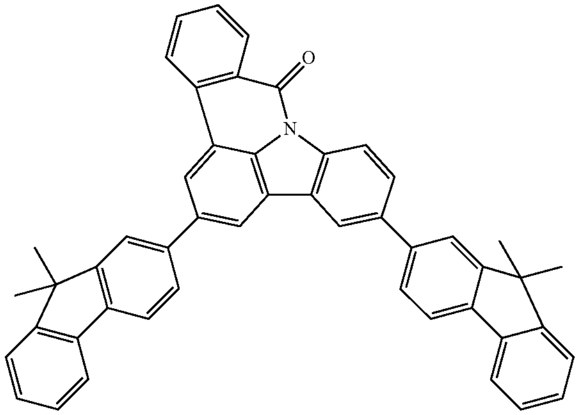
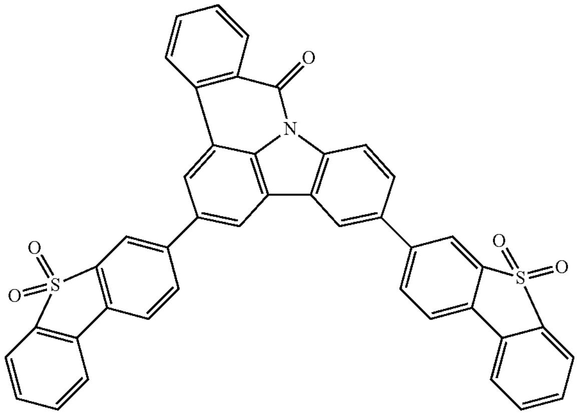
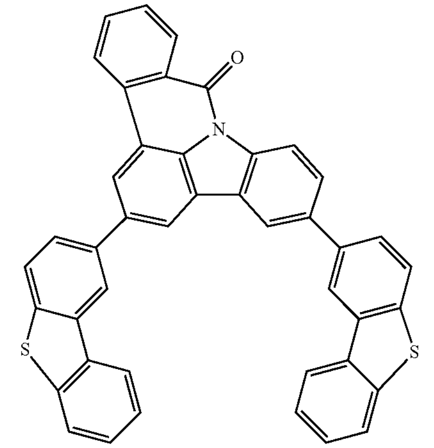
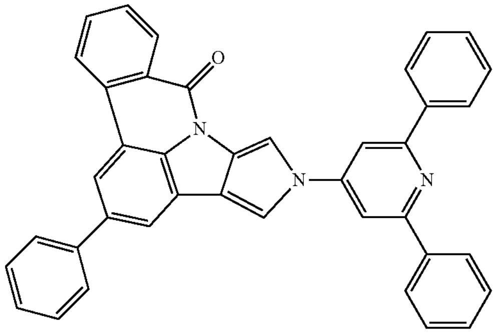
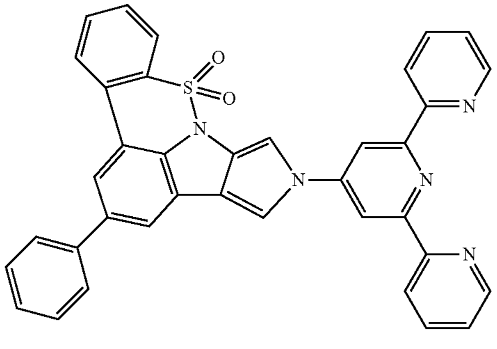
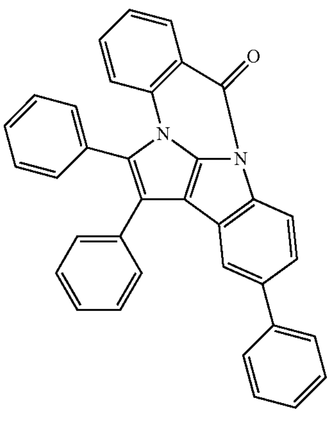
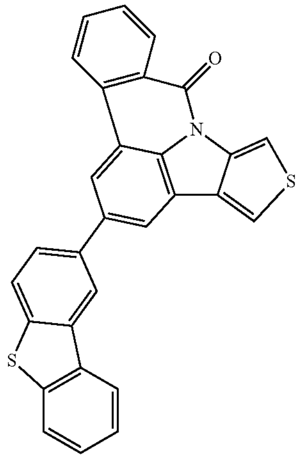

-continued
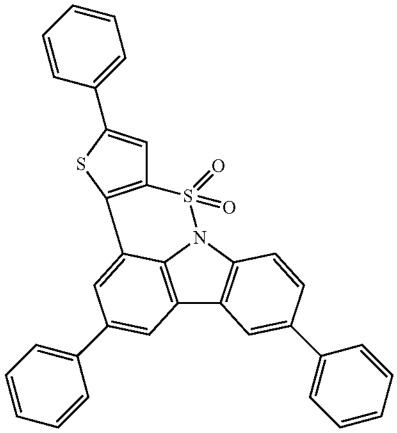
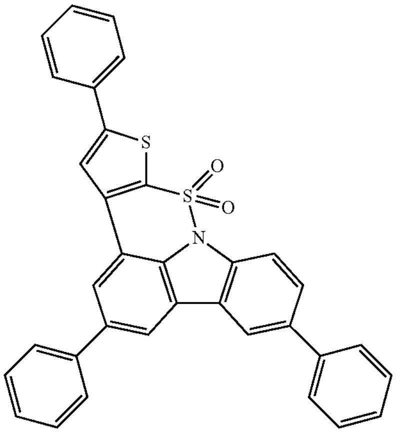
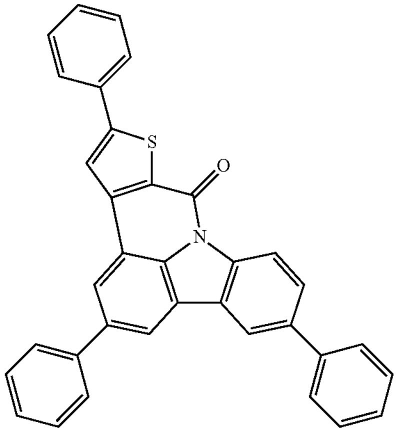
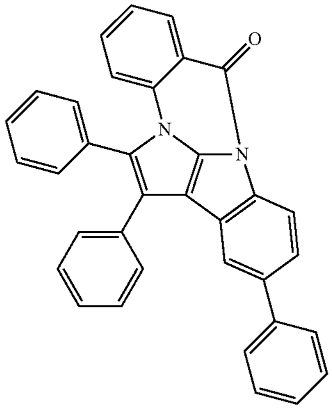
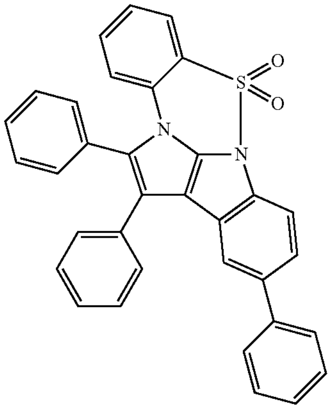
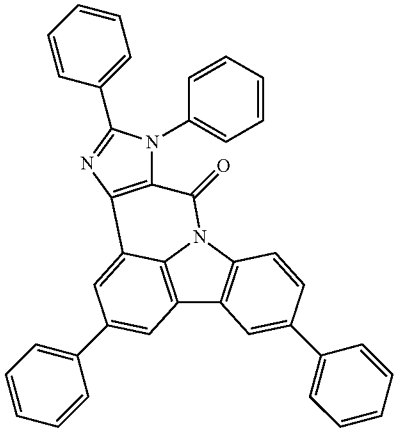
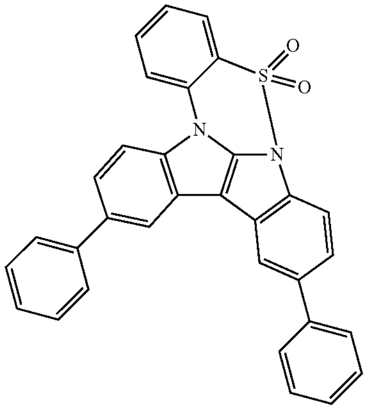
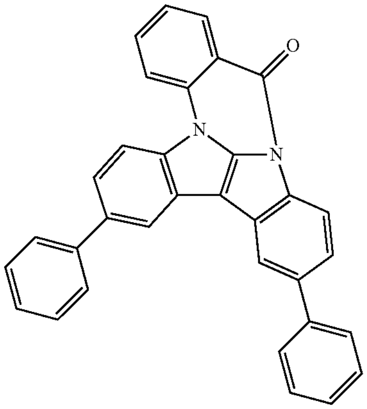
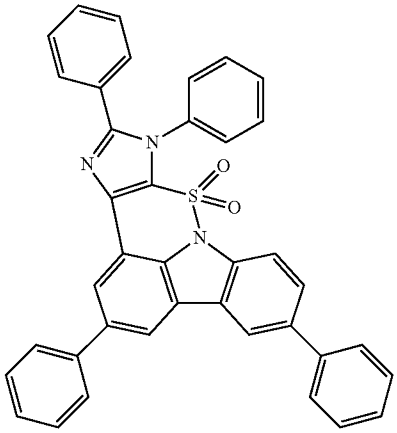
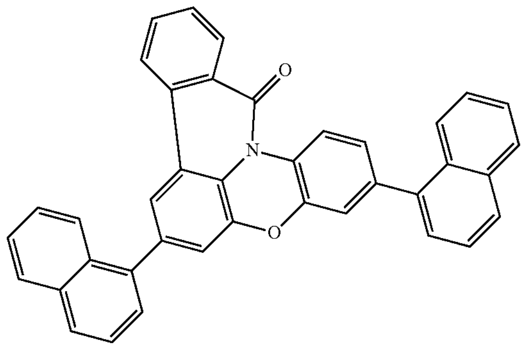

-continued
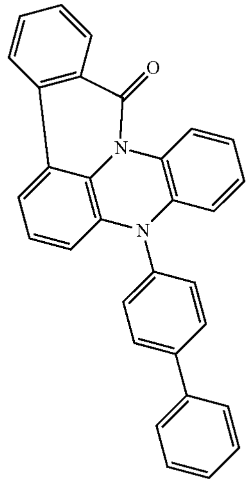
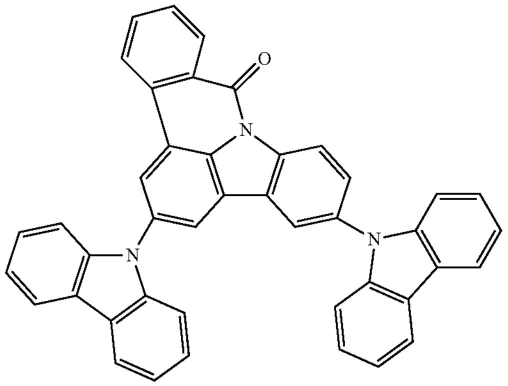
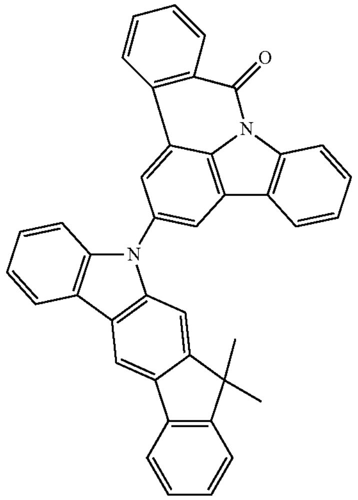
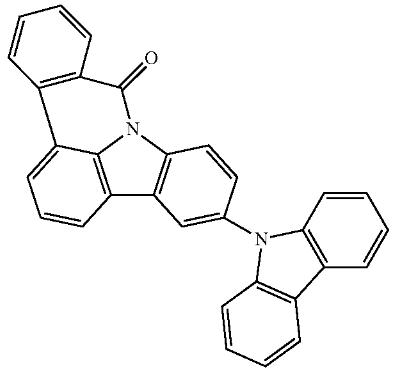
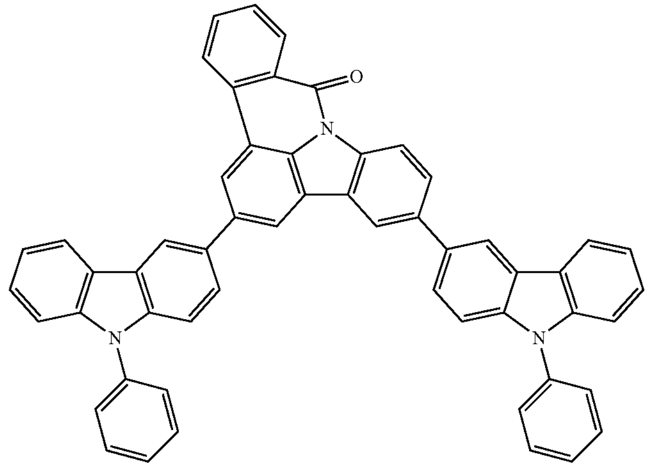
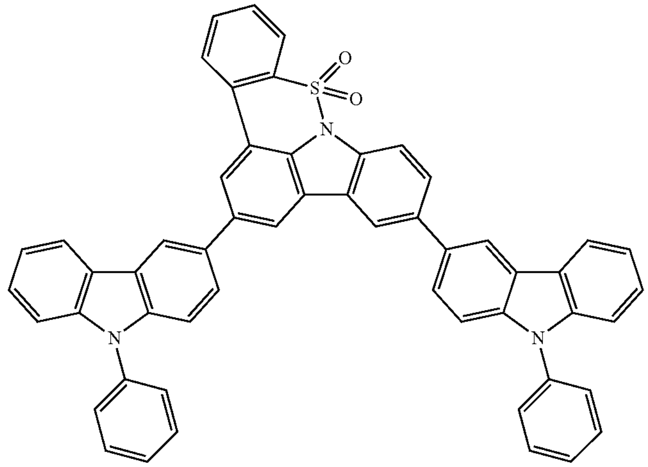
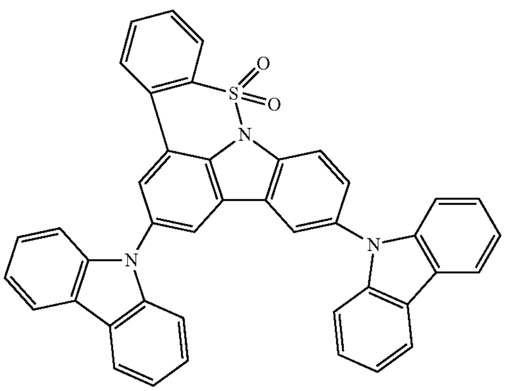

-continued
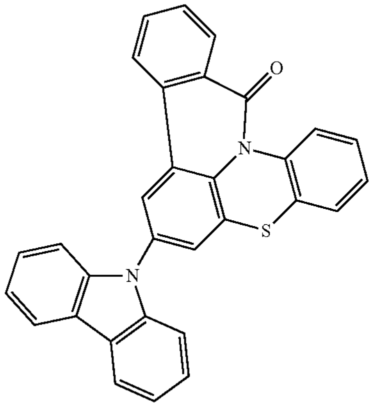
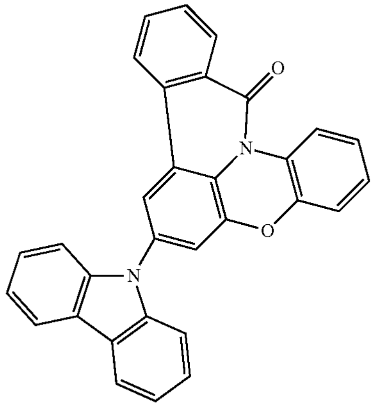
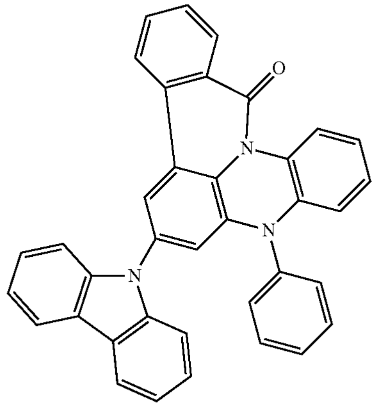
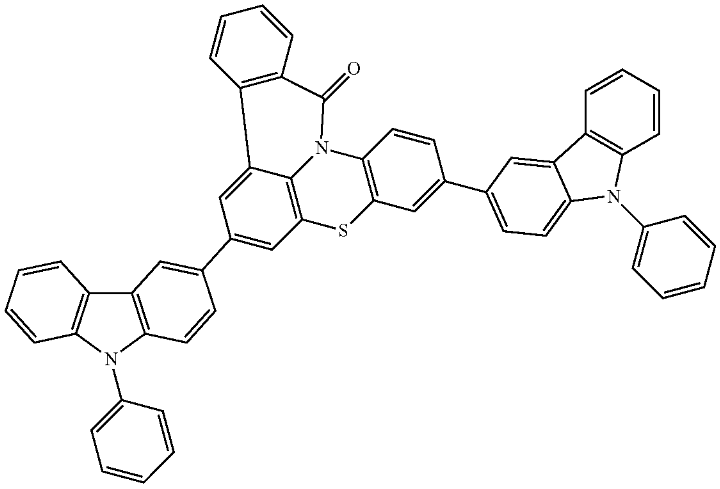
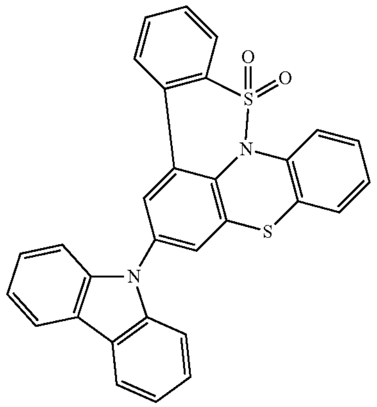
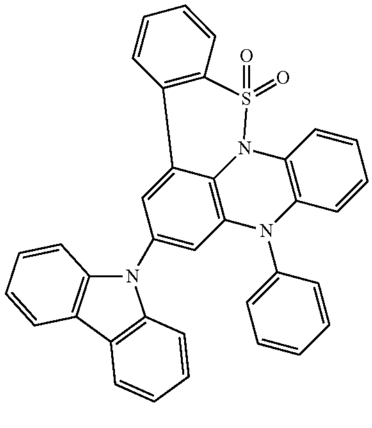
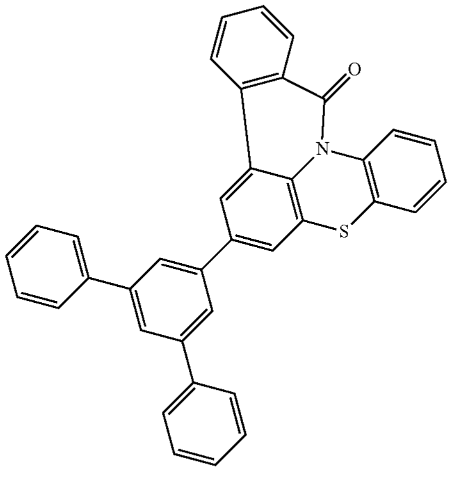
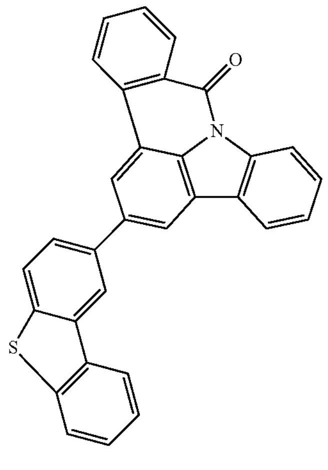

-continued
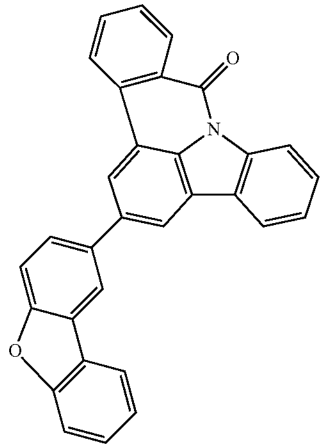
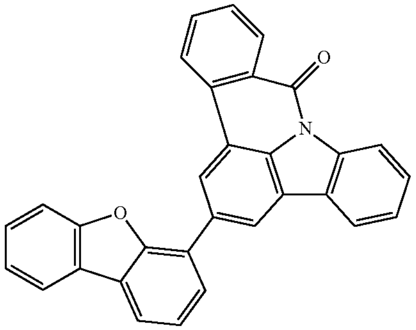
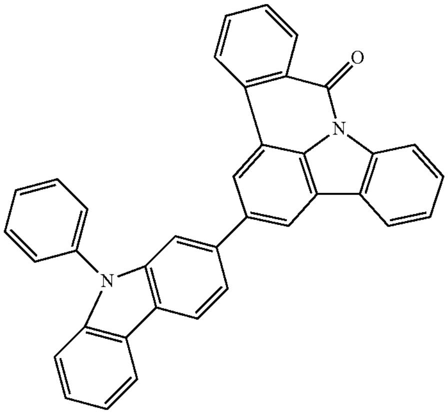
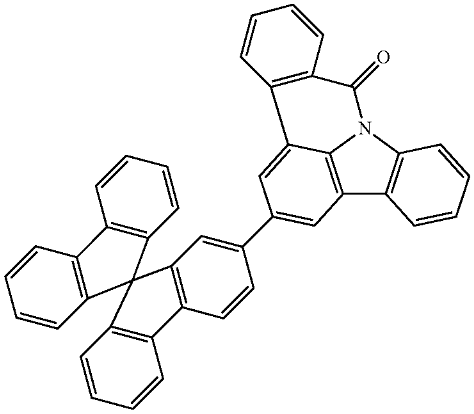
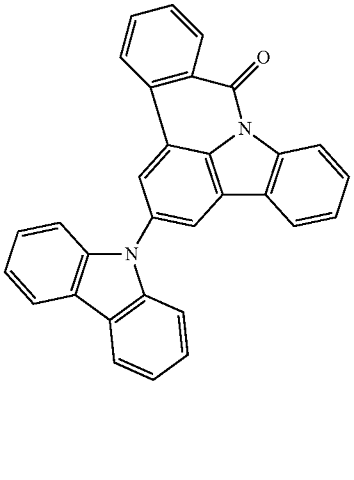
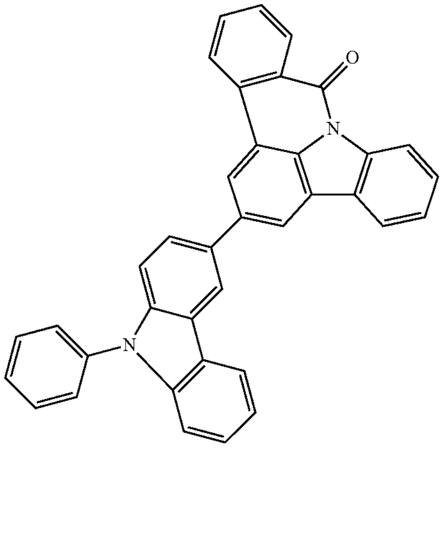

-continued

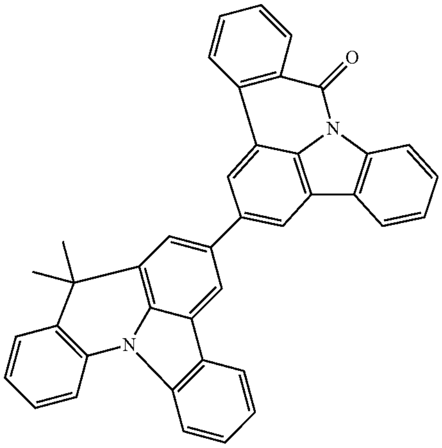

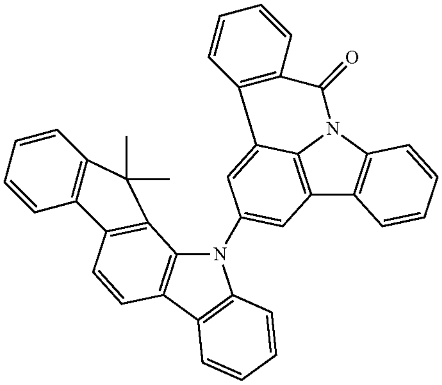

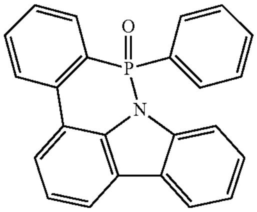

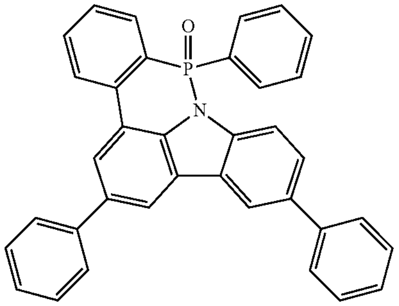

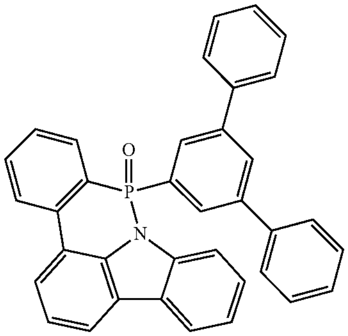

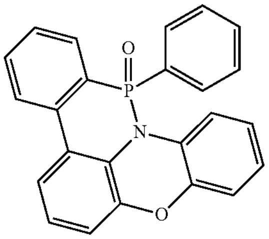

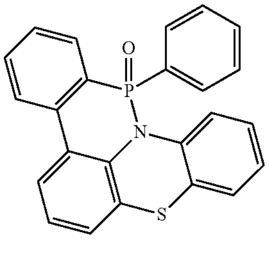

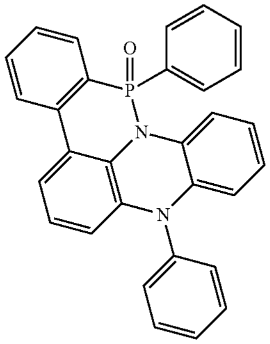

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013).

The compound according to the invention in accordance with the above-mentioned embodiments can be employed in various layers, depending on the precise structure. Preference is given to an organic electroluminescent device comprising a compound of the formula (1) or the preferred embodiments indicated above as matrix material for fluorescent or phosphorescent emitters, in particular for phosphorescent emitters, and/or in a hole-blocking layer and/or in an electron-transport layer and/or in an electron-blocking or exciton-blocking layer and/or in a hole-transport layer, depending on the precise substitution.

In a further embodiment of the invention, the organic electroluminescent device comprises the compound of the formula (1) or the preferred embodiments indicated above in an optical coupling-out layer. An optical coupling-out layer here is taken to mean a layer which is not located between the anode and the cathode, but instead which is applied to an electrode outside the actual device, for example between an electrode and a substrate, in order to improve the optical coupling-out.

In a preferred embodiment of the invention, the compound of the formula (1) or the preferred embodiments indicated above is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or the preferred embodiments indicated above is employed as matrix material for an emitting compound in an emitting layer, it is preferably employed in combination with one or more phosphorescent materials (triplet emitters). Phosphorescence in the sense of this invention is taken to mean the luminescence from an excited state of relatively high spin multiplicity, i.e. a spin state >1, in particular from an excited triplet state. For the purposes of this application, all luminescent complexes with transition metals or lanthanides, in particular all iridium, platinum and copper complexes, are to be regarded as phosphorescent compounds.

The mixture of the compound of the formula (1) or the preferred embodiments indicated above and the emitting compound comprises between 99 and 1% by vol., preferably between 98 and 10% by vol., particularly preferably between 97 and 60% by vol., in particular between 95 and 80% by vol., of the compound of the formula (1) or the preferred embodiments indicated above, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1) or the preferred embodiments indicated above as matrix material for a phosphorescent emitter in combination with a further matrix material. Particularly suitable matrix materials which can be employed in combination with the compounds of the formula (1) or the preferred embodiments indicated above are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 or WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2007/063754, WO 2008/056746, WO 2010/015306 or the unpublished applications DE 102009053382.6, DE 102009053644.2 or DE 102009053645.0, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with the unpublished applications DE 102009048791.3 and DE 102009053836.4. A further phosphorescent emitter which emits at shorter wavelength than the actual emitter may likewise be present in the mixture as co-host.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

In a further preferred embodiment of the invention, the compound of the formula (1) or the preferred embodiments indicated above is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, LiQ (lithium hydroxyquinolinate).

In still a further preferred embodiment of the invention, the compound of the formula (1) or the preferred embodiments indicated above is employed in a hole-blocking layer. A hole-blocking layer is taken to mean a layer which is directly adjacent to an emitting layer on the cathode side.

It is furthermore possible to use the compound of the formula (1) or the preferred embodiments indicated above both in a hole-blocking layer or electron-transport layer and also as matrix in an emitting layer.

In still a further embodiment of the invention, the compound of the formula (1) or the preferred embodiments indicated above is employed in a hole-transport layer or in an electron-blocking layer or exciton-blocking layer.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1) according to the invention or the preferred embodiments indicated above.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), inkjet printing or nozzle printing. Soluble compounds, which are obtained, for example, by suitable substitution, are necessary for this purpose. These processes are also particularly suitable for oligomers, dendrimers and polymers.

Furthermore possible are hybrid processes, in which, for example, one or more layers are applied from solution and one or more further layers are applied by vapour deposition.

These processes are generally known to the person skilled in the art and can be applied by him without inventive step to organic electroluminescent devices comprising the compounds according to the invention.

The present invention furthermore relates to the compounds of the following formula (1') which are indicated as preferred above, formula (1')

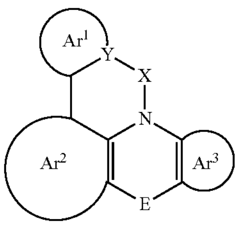

where the compound is substituted by at least one radical R which represents an aromatic or heteroaromatic ring system, and where the following applies to the symbols and indices used:

X is C═O, $C(R)_2$, NR, O, S, C═S, C═NR, C═$C(R)_2$, $Si(R)_2$, BR, PR, P(═O)R, SO or $SO_2$;

Y is C if $Ar^1$ represents a 6-membered aryl or heteroaryl ring group, or is C or N if $Ar^1$ represents a 5-membered heteroaryl ring group;

E is, identically or differently on each occurrence, a single bond, $C(R)_2$, NR, O, S, C═O, C═S, C═NR, C═$C(R)_2$, $Si(R)_2$, BR, PR, P(═O)R, SO or $SO_2$;

$Ar^1$ is, together with the group Y and the carbon atom explicitly depicted, an aromatic or heteroaromatic ring system having 5 to 30 aromatic ring atoms, which may be substituted by one or more radicals R;

$Ar^2$ is, together with the carbon atoms explicitly depicted, an aromatic or heteroaromatic ring system having 5 to 30 aromatic ring atoms, which may be substituted by one or more radicals R; if $Ar^2$ stands for an aromatic ring system having at least one nitrogen atom which is substituted by an aromatic or heteroaromatic radical R, this radical R then contains more than 6 aromatic C atoms;

$Ar^3$ is, together with the carbon atoms explicitly depicted, an aromatic or heteroaromatic ring system having 5 to 30 aromatic ring atoms, which may be substituted by one or more radicals R;

R is selected on each occurrence, identically or differently, from the group consisting of H, D, F, Cl, Br, I, CN, $NO_2$, $N(Ar^4)_2$, $N(R^1)_2$, C(═O)$Ar^4$, C(═O)$R^1$, P(═O)$(Ar^4)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may be replaced by $R^1C$═$CR^1$, C≡C, $Si(R^1)_2$, $Ge(R^1)_2$, $Sn(R^1)_2$, C═O, C═S, C═Se, C═$NR^1$, P(═O)($R^1$), SO, $SO_2$, $NR^1$, O, S or $CONR^1$ and where one or more H atoms may be replaced by D, F, Cl, Br, I, CN or $NO_2$, an aromatic or heteroaromatic ring system having 5 to 80, preferably 5 to 60, aromatic ring atoms, which may in each case be substituted by one or more radicals $R^1$, an aryloxy or heteroaryloxy group having 5 to 60 aromatic ring atoms, which may be substituted by one or more radicals $R^1$, or a combination of these systems, where two or more adjacent substituents R may optionally form a monocyclic or polycyclic, aliphatic, aromatic or heteroaromatic ring system, which may be substituted by one or more radicals $R^1$;

$R^1$ is selected on each occurrence, identically or differently, from the group consisting of H, D, F, Cl, Br, I, CN, $NO_2$, $N(Ar^4)_2$, $N(R^2)_2$, C(═O)$Ar^4$, C(═O)$R^2$, P(═O)$(Ar^4)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent $CH_2$ groups may be replaced by $R^2C$═$CR^2$, C≡C, $Si(R^2)_2$, $Ge(R^2)_2$, $Sn(R^2)_2$, C═O, C═S, C═Se, C═$NR^2$, P(═O)($R^2$), SO, $SO_2$, $NR^2$, O, S or $CONR^2$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^2$, an aryloxy or heteroaryloxy group having 5 to 60 aromatic ring atoms, which may be substituted by one or more radicals $R^2$, or a combination of these systems, where two or more adjacent substituents R may optionally form a monocyclic or polycyclic, aliphatic, aromatic or heteroaromatic ring system, which may be substituted by one or more radicals $R^2$;

$Ar^4$ is on each occurrence, identically or differently, an aromatic or heteroaromatic ring system having 5-30 aromatic ring atoms, which may be substituted by one or more non-aromatic radicals $R^2$; two radicals $Ar^4$ which are bonded to the same N atom or P atom may also be bridged to one another by a single bond or a bridge selected from $N(R^2)$, $C(R^2)_2$ or O;

$R^2$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^2$ may form a mono- or polycyclic, aliphatic, aromatic or heteroaromatic ring system with one another;

the following compounds are excluded from the invention:

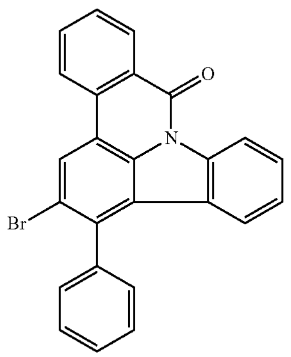
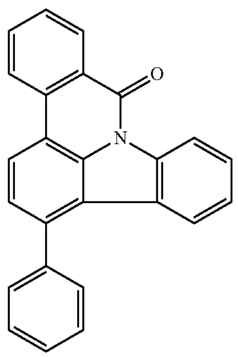
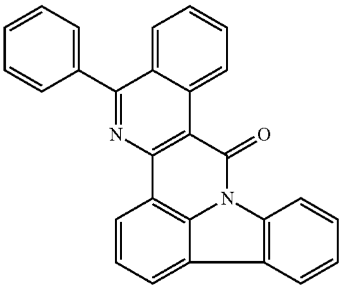
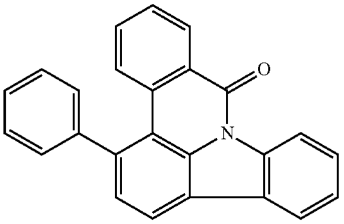
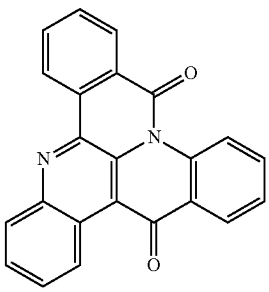
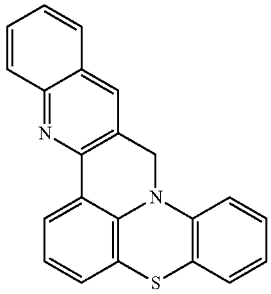
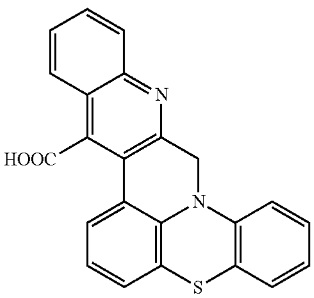

-continued

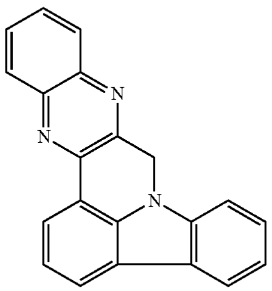
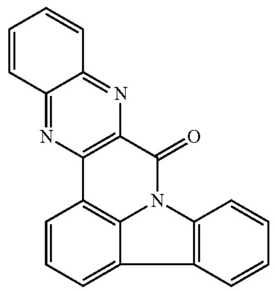
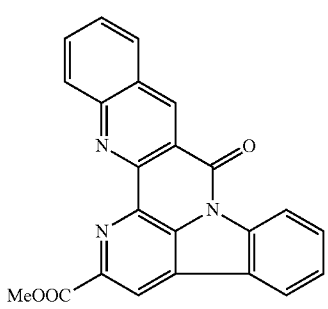
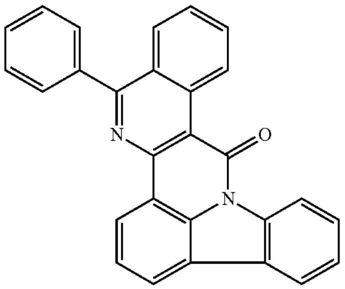
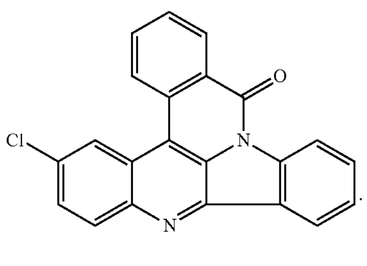

The same preferences as indicated above for the compounds of the formula (1) apply to the compounds of the formula (1') according to the invention.

The compounds of the formula (1) or (1') or the preferred embodiments can be prepared by synthetic steps known to the person skilled in the art, as depicted schematically in Scheme 1 to 3.

Scheme 1:
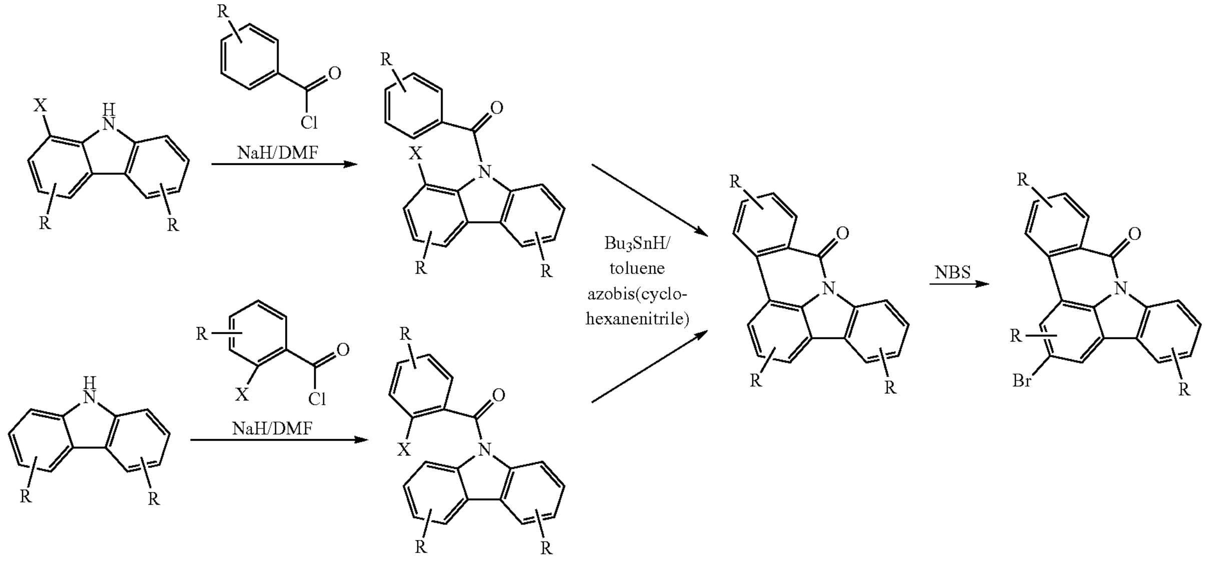
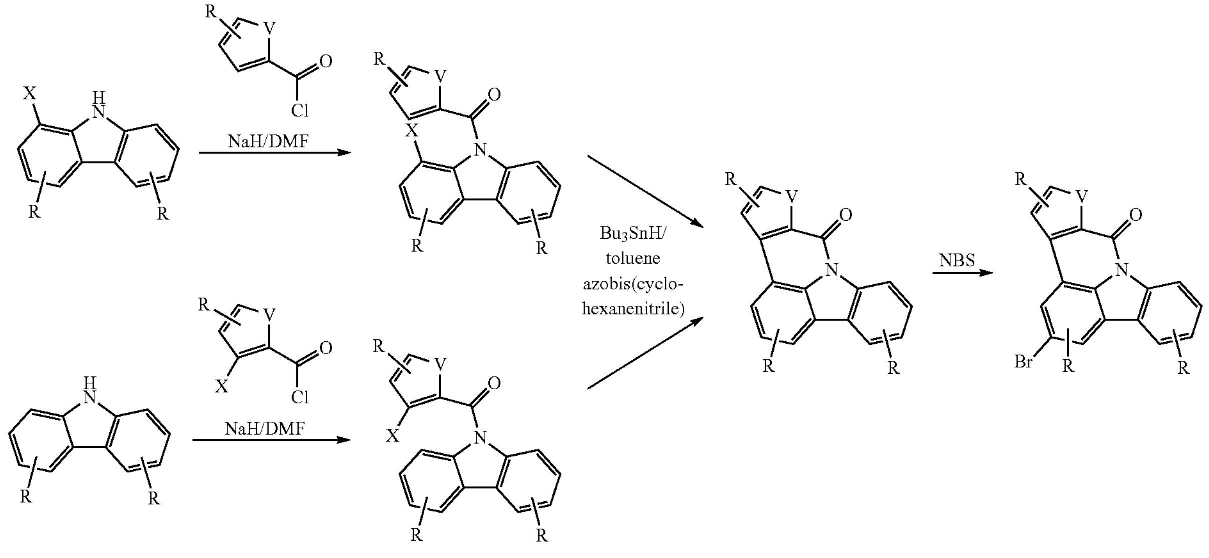
V = O, N, S
X = Cl, Br, I

Scheme 2:
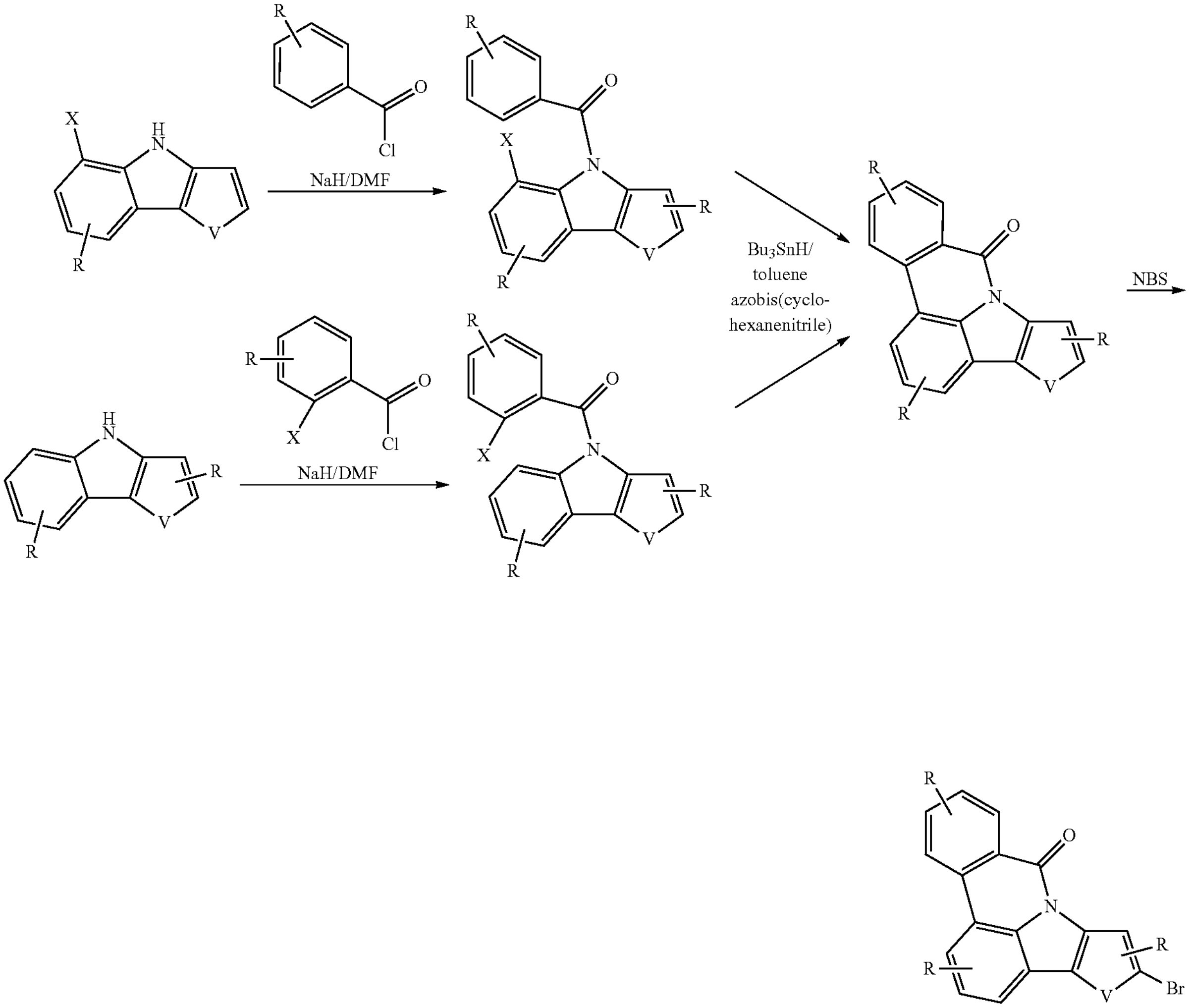
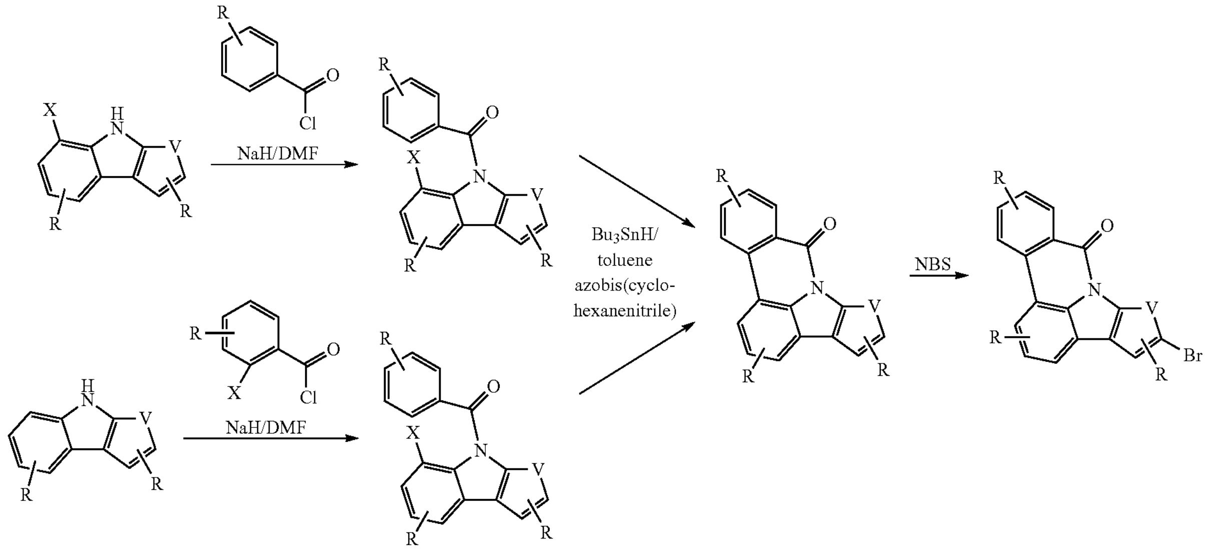

-continued

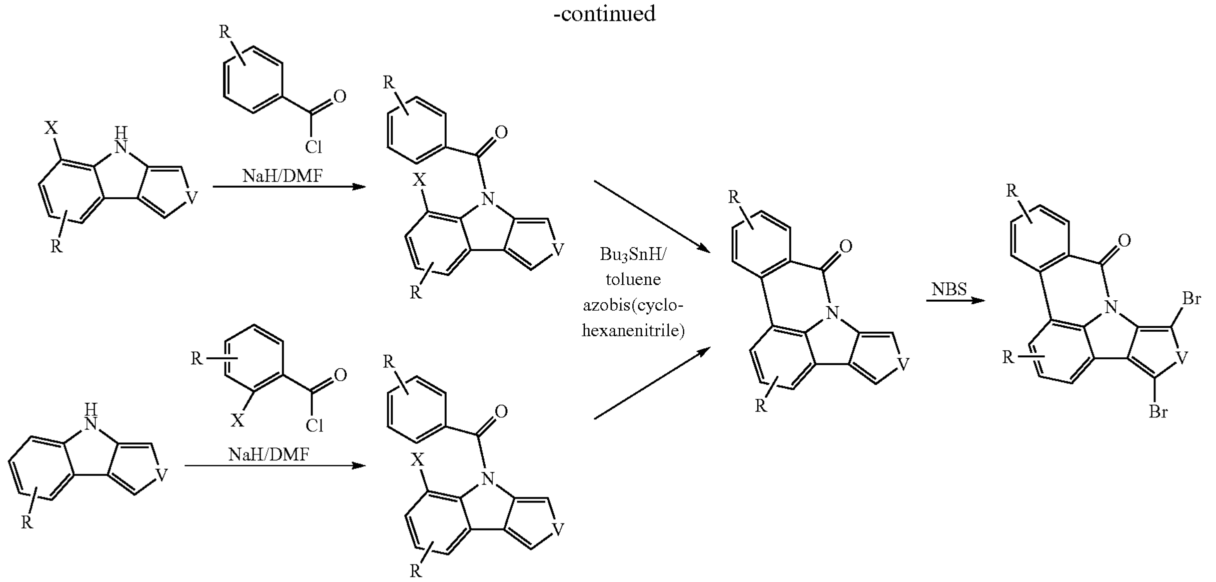

V = O, N, S
X = Cl, Br, I

Scheme 3:

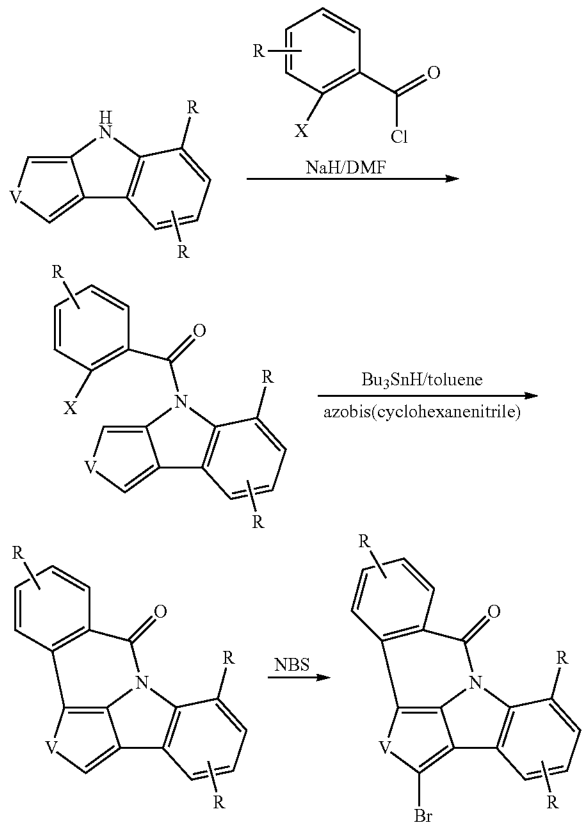

V = O, N, S
X = Cl, Br, I

The functionalised, in particular brominated compounds represent the central building block for further functionalisation, as depicted in Scheme 1 to 3. Thus, these functionalised compounds can easily be converted into compounds of the formula (1) or formula (1') by Suzuki coupling or coupling to diarylamines by the Hartwig-Buchwald method with carbazole derivatives or triarylamine derivatives.

The brominated compounds can furthermore be lithiated and converted into ketones by reaction with electrophiles, such as benzonitrile, and subsequent acidic hydrolysis or into phosphine oxides with chlorodiphenyl-phosphines and subsequent oxidation.

The present invention therefore furthermore relates to a process for the preparation of a compound of the formula (1'), comprising the reaction steps:

a) synthesis of the skeleton which carries a reactive leaving group instead of the group R; and
b) introduction of the group R, preferably by a coupling reaction, for example Suzuki coupling or Hartwig-Buchwald coupling.

The reactive leaving group here is preferably selected from Cl, Br, I, boronic acid or boronic acid derivatives, triflate or tosylate or V stands for NH, i.e. the reactive leaving group is hydrogen, if a bond is formed between N and R.

The compounds according to the invention described above, in particular compounds which are substituted by reactive leaving groups, such as bromine, iodine, chlorine, boronic acid or boronic acid ester, or by reactive, polymerisable groups, such as olefins or oxetanes, can be used as monomers for the generation of corresponding oligomers, dendrimers or polymers. The oligomerisation or polymerisation here preferably takes place via the halogen functionality or the boronic acid functionality or via the polymerisable group. It is furthermore possible to crosslink the polymers via groups of this type. The compounds and polymers according to the invention can be employed as crosslinked or uncrosslinked layer.

The invention therefore furthermore relates to oligomers, polymers or dendrimers comprising one or more of the compounds according to the invention mentioned above, where one or more bonds are present from the compound according to the invention to the polymer, oligomer or dendrimer. Depending on the linking of the compound according to the invention, this therefore forms a side chain of the oligomer or polymer or is linked in the main chain. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to homopolymers or copolymers in which the units of the formula (1') or the above-mentioned preferred embodiments are present to the extent of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 2000/22026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers may also comprise further units, for example hole-transport units, in particular those based on triarylamines, and/or electron-transport units. In addition, the polymers may comprise triplet emitters, either copolymerised or mixed in as a blend. In particular, the combination of units of the formula (1') or the above-mentioned preferred embodiments with triplet emitters results in particularly good results.

Furthermore, the compounds of the formula (1') or the above-mentioned preferred embodiments may also be functionalised further and thus converted into extended structures. The reaction with arylboronic acids by the Suzuki method or with primary or secondary amines by the Hartwig-Buchwald method may be mentioned here as an example. Thus, the compounds of the formula (1') or the above-mentioned preferred embodiments may also be bonded directly to phosphorescent metal complexes or also to other metal complexes.

The present invention therefore furthermore relates to the use of the above-mentioned compounds of the formula (1') according to the invention in an electronic device, in particular in an organic electroluminescent device.

The compounds according to the invention and the organic electroluminescent devices according to the invention are distinguished by the following surprising advantages over the prior art:

1. The compounds according to the invention or compounds of the formula (1) or the above-mentioned preferred embodiments, employed as matrix material for fluorescent or phosphorescent emitters, result in very high efficiencies and in long lifetimes. This applies in particular if the compounds are employed as matrix material for a red- or green-phosphorescent emitter.
2. The compounds according to the invention have high thermal stability.
3. The compounds according to the invention, employed in organic electroluminescent devices, result in high efficiencies and in steep current/voltage curves with low use voltages.
4. Also on use as electron-transport material, the compounds according to the invention result in very good properties with respect to the efficiency, lifetime and operating voltage of organic electroluminescent devices.

These above-mentioned advantages are not accompanied by an impairment of the other electronic properties.

The invention is explained in greater detail by the following examples without wishing to restrict it thereby. The person skilled in the art will be able to use the descriptions to carry out the invention throughout the range disclosed and prepare further compounds according to the invention without inventive step and use them in electronic devices or apply the process according to the invention.

EXAMPLES

The following syntheses are carried out under a protective-gas atmosphere, unless indicated otherwise. The starting materials can be purchased from ALDRICH or ABCR (palladium(II) acetate, tri-o-tolylphosphine, inorganic chemicals, solvents). The synthesis of 3-phenyl-4-(phenylsulfonyl)-4H-furo[3,4-b]indole can be carried out in accordance with the literature (Journal of Organic Chemistry 2002, 67(3), 1001-1003). The syntheses of 11,12-dihydro-11-phenylindolo[2,3-a]carbazole (WO 2009/136595) and 2,12-dimethyl-10-phenyl-10,12-dihydro-10-azaindeno-[2,1-b]fluorene (unpublished application DE 102009023155.2) are likewise known from the literature.

Example 1a

3-Phenyl-4H-furo[3,4-b]indole

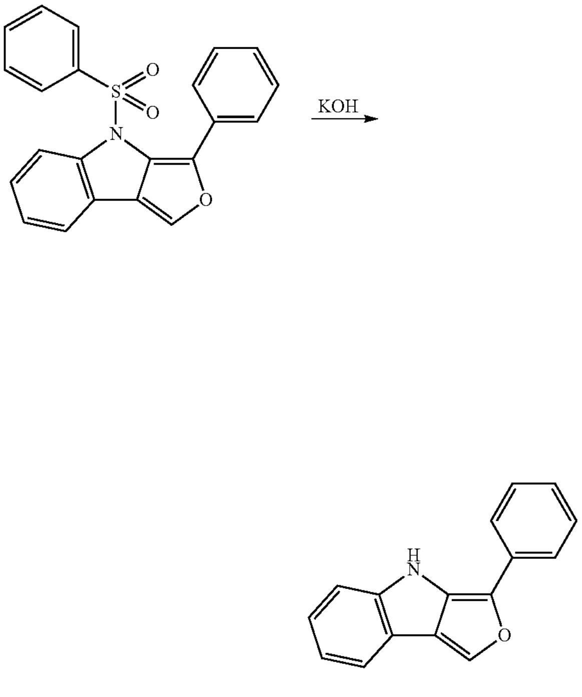

45 g (123 mmol) of 3-phenyl-4-(phenylsulfonyl)-4H-furo[3,4-b]indole and 48 g (856 mmol) of potassium hydroxide in 65 ml of DMSO and 21 ml of water are heated under reflux for 1 h. The mixture is subsequently cooled to room temperature, neutralised using 1M HCl solution and extracted with dichloromethane. The solvent is evaporated in vacuo, and the residue is purified by chromatography (heptane/ethyl acetate 10:1). Yield: 22.4 g (96 mmol), 80%.

The following compound is obtained analogously:

| Ex. | Starting material | Product | Yield |
|---|---|---|---|
| 1b | 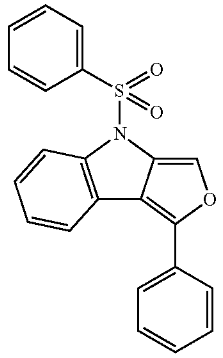 [SMILES: O=S(=O)(c1ccccc1)n1c2ccccc2c2c(-c3ccccc3)occ21] Journal of Organic Chemistry (1992), 57(22), 5878-91. | 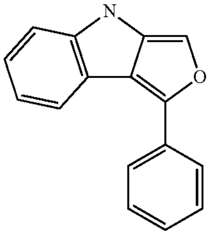 [SMILES: c1ccc(-c2occ3[nH]c4ccccc4c23)cc1] | 81% |

Example 2a

2-Bromophenyl-(3-phenylfuro[3,4-b]indol-4-yl) methanone

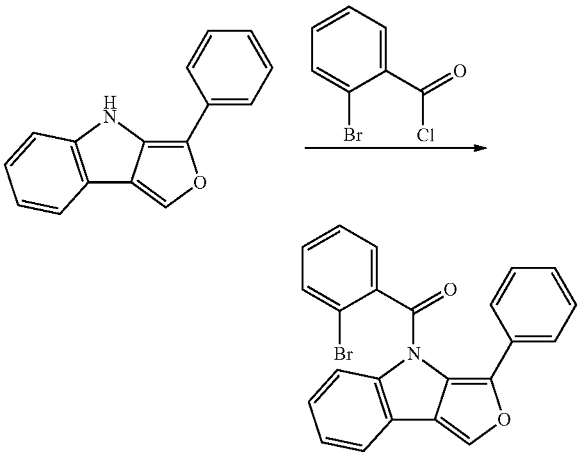

2.1 g (52.5 mmol) of NaH (60% in mineral oil) are dissolved in 500 ml of THF under a protective-gas atmosphere. 11.5 g (50 mmol) of 3-phenyl-4H-furo[3,4-b]indole and 11.5 g (52.5 mmol) of 15-crown-5, dissolved in 200 ml of THF, are added. After 1 h at room temperature, a solution of 12 g (55 mmol) of 2-bromobenzoyl chloride in 250 ml of THF is added dropwise.

The reaction mixture is stirred at room temperature for 18 h. After this time, the reaction mixture is poured onto ice and extracted three times with dichloromethane. The combined organic phases are dried over $Na_2SO_4$ and evaporated. The residue is extracted with hot toluene and recrystallised from toluene/n-heptane. The yield is 12 g (60%).

The following compounds are obtained analogously:

| Ex. | Starting material | Product | Yield |
|---|---|---|---|
| 2b | 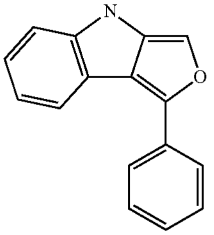 [SMILES: c1ccc(-c2occ3[nH]c4ccccc4c23)cc1] | 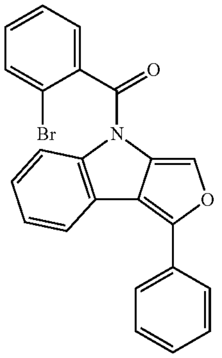 [SMILES: O=C(c1ccccc1Br)n1c2ccccc2c2c(-c3ccccc3)occ21] | 57% |
| 2c | 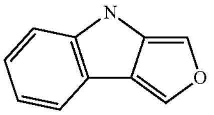 [SMILES: c1ccc2c(c1)[nH]c1cocc12] Journal of Organic Chemistry (1998), 63(22), 7680-7686. | 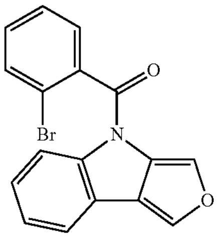 [SMILES: O=C(c1ccccc1Br)n1c2ccccc2c2cocc21] | 58% |
| 2d | 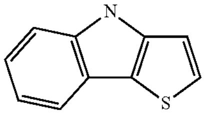 [SMILES: c1ccc2c(c1)[nH]c1ccsc12] Organic Letters (2004), 6(4), 533-535. | 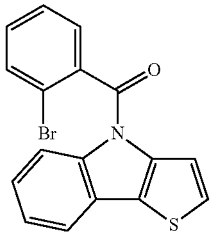 [SMILES: O=C(c1ccccc1Br)n1c2ccccc2c2sccc21] | 61% |
| 2e | 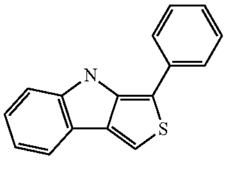 [SMILES: c1ccc(-c2scc3c2[nH]c2ccccc23)cc1] Journal of Heterocyclic Chemistry (1982), 19(2), 227-31. | 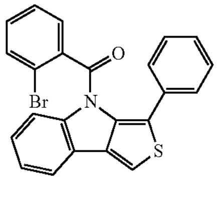 [SMILES: O=C(c1ccccc1Br)n1c2ccccc2c2csc(-c3ccccc3)c21] | 49% |
| 2f | 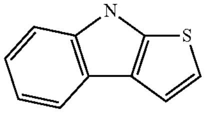 [SMILES: c1ccc2c(c1)[nH]c1sccc12] Bioorganic & Medicinal Chemistry, 14(3), 714-723; 2006 | 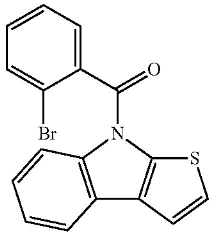 [SMILES: O=C(c1ccccc1Br)n1c2ccccc2c2ccsc21] | 64% |
| 2g | 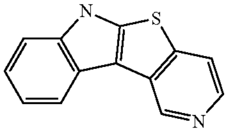 [SMILES: c1ccc2c(c1)[nH]c1sc3ccncc3c12] Bulletin de la Societe Chimique de France, (1), 198-8; 1987 | 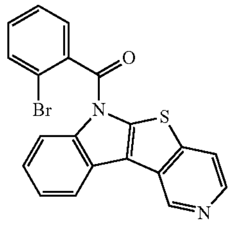 [SMILES: O=C(c1ccccc1Br)n1c2ccccc2c2c3cnccc3sc21] | 43% |

-continued

| Ex. | Starting material | Product | Yield |
|---|---|---|---|
| 2h | 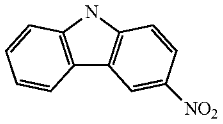 [SMILES: O=[N+]([O-])c1ccc2[nH]c3ccccc3c2c1] | 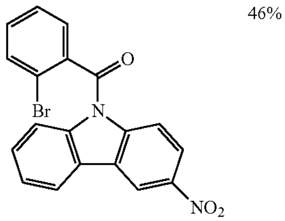 | 46% |

Example 2i (1-Chlorobenzo[4,5]furo[3,2-b]indol-10-yl)phenyl-methanone

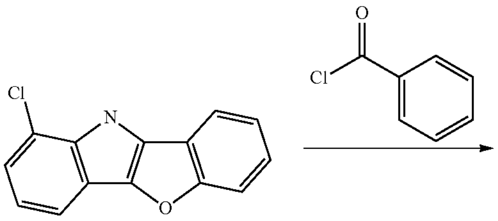

-continued

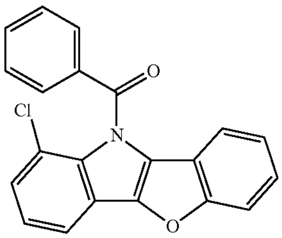

2.1 g (52.5 mmol) of NaH (60% in mineral oil) are dissolved in 500 ml of THF under a protective-gas atmosphere. 12.6 g (50 mmol) of 3-phenyl-4H-furo[3,4-b]indole and 11.5 g (52.5 mmol) of 15-crown-5 dissolved in 200 ml of THF are added. After 1 h at room temperature, a solution of 7.7 g (55 mmol) of benzoyl chloride in 250 ml of THF is added dropwise. The reaction mixture is then stirred at room temperature for 18 h. After this time, the reaction mixture is poured onto ice and extracted three times with dichloromethane. The combined organic phases are dried over $Na_2SO_4$ and evaporated. The residue is extracted with hot toluene and recrystallised from toluene/n-heptane. The yield is 12.5 g (69%).

The following compounds are obtained analogously:

| Ex. | Starting material 1 | Product | Yield |
|---|---|---|---|
| 2j | 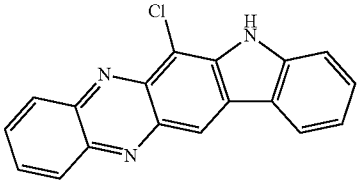 [SMILES: Clc1c2nc3ccccc3nc2cc2c1[nH]c1ccccc12] DE 1197462 | 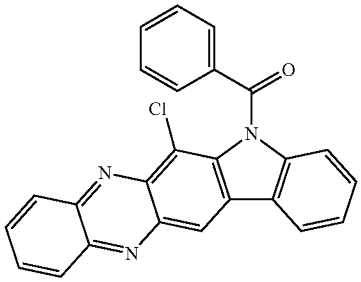 [SMILES: O=C(c1ccccc1)n1c2ccccc2c2cc3nc4ccccc4nc3c(Cl)c21] | 78% |
| 2k | 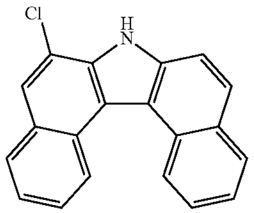 [SMILES: Clc1cc2ccccc2c2c1[nH]c1ccc3ccccc3c12] Journal of Organic Chemistry (1988), 53(4), 794-9. | 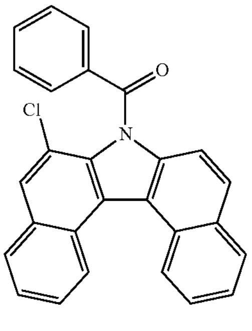 [SMILES: O=C(c1ccccc1)n1c2ccc3ccccc3c2c2c3ccccc3cc(Cl)c21] | 90% |

-continued

| Ex. | Starting material 1 | Product | Yield |
|---|---|---|---|
| 2l | 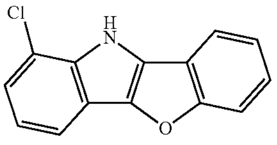 [SMILES: Clc1cccc2c1[nH]c1c3ccccc3oc21] WO 2006096030 | 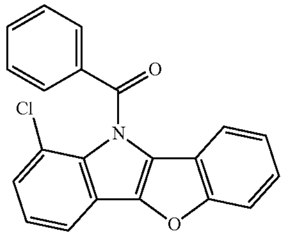 [SMILES: O=C(c1ccccc1)n1c2c(Cl)cccc2c2oc3ccccc3c21] | 87% |

Example 2m

4-(2-Bromobenzenesulfonyl)-3-phenyl-4H-furo[3,4-b]indole

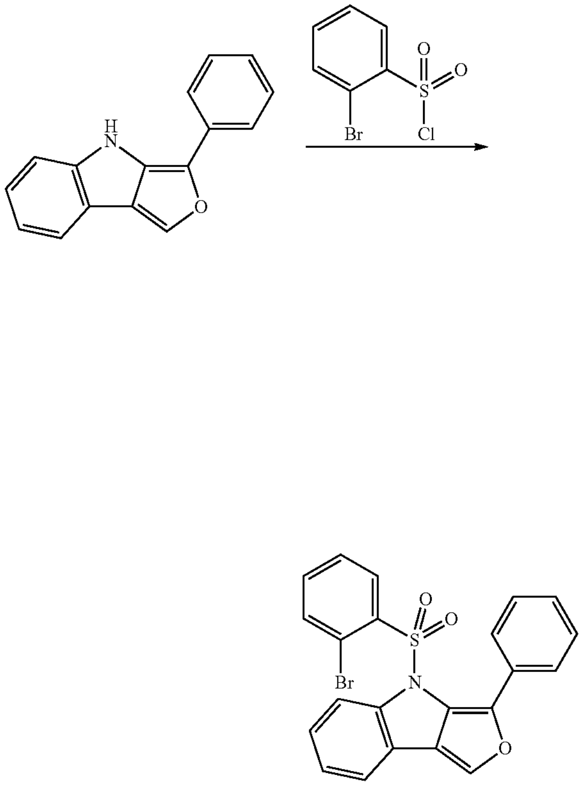

2.1 g (52.5 mmol) of NaH (60% in mineral oil) are dissolved in 500 ml of THF under a protective-gas atmosphere. 11.5 g (50 mmol) of 3-phenyl-4H-furo[3,4-b]indole and 11.5 g (52.5 mmol) of 15-crown-5 dissolved in 200 ml of THF are added. After 1 h at room temperature, a solution of 12.7 g (55 mmol) of 2-bromobenzenesulfonyl chloride in 250 ml of THF is added dropwise. The reaction mixture is stirred at room temperature for 18 h. After this time, the reaction mixture is poured onto ice and extracted three times with dichloromethane. The combined organic phases are dried over $Na_2SO_4$ and evaporated. The residue is extracted with hot toluene and recrystallised from toluene/n-heptane. The yield is 16 g (75%).

The following compounds are obtained analogously:

| Ex. | Starting material 1 | Product | Yield |
|---|---|---|---|
| 2n | 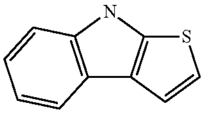 | 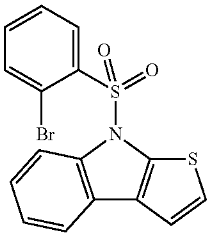 [SMILES: O=S(=O)(c1ccccc1Br)n1c2ccccc2c2ccsc21] | 80% |
| 2o | 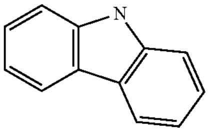 [SMILES: c1ccc2c(c1)[nH]c1ccccc12] | 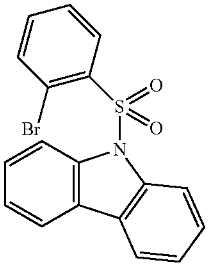 [SMILES: O=S(=O)(c1ccccc1Br)n1c2ccccc2c2ccccc21] | 86% |

Example 3a

Cyclisation

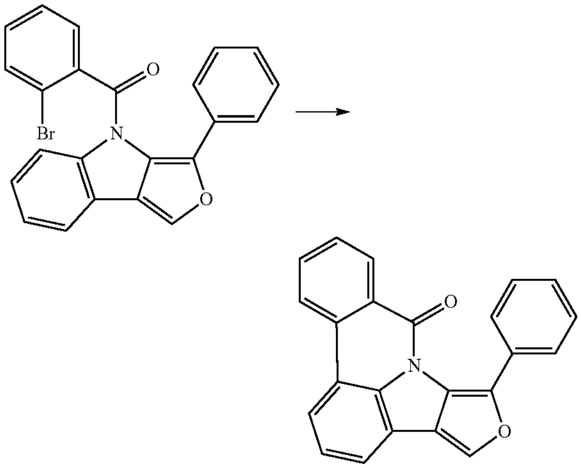

Under a protective-gas atmosphere, 43 ml of tributyltin hydride (16 mmol) and 30 g (12.5 mmol) of 1,1"-azobis (cyclohexane-1-carbonitrile) in 600 ml of toluene are added dropwise over a period of 4 h to a boiling solution of 5.2 g (12.5 mmol) of 2-bromophenyl-(3-phenylfuro[3,4-b]indol-4-yl)-methanone in 600 ml of toluene. The mixture is subsequently heated under reflux for 3 h. After this time, the reaction mixture is poured onto ice and extracted three times with dichloromethane. The combined organic phases are dried over $Na_2SO_4$ and evaporated. The residue is recrystallised from toluene. The yield is 3.1 g (76%).

The following compounds are obtained analogously. The isomers can be separated by recrystallisation from toluene/isopropanol.

| Ex. | Starting material 1 | Product 1 | Yield | Ex. | Product 2 | Yield |
|---|---|---|---|---|---|---|
| 3b | 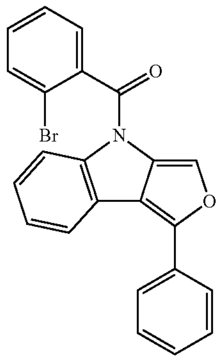 [SMILES: O=C(c1ccccc1Br)n1c2ccccc2c2c(-c3ccccc3)occ21] | 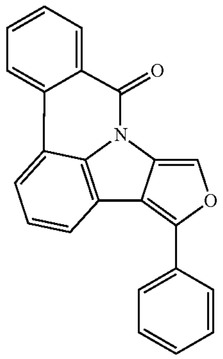 [SMILES: O=c1c2ccccc2c2cccc3c4c(-c5ccccc5)occ4n1c23] | 43% | 3c | 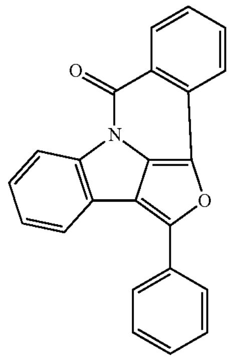 [SMILES: O=c1c2ccccc2c2oc(-c3ccccc3)c3c4ccccc4n1c23] | 23% |
| 3d | 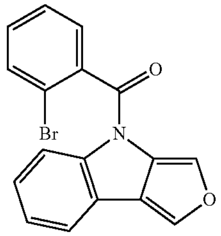 [SMILES: O=C(c1ccccc1Br)n1c2ccccc2c2cocc21] | 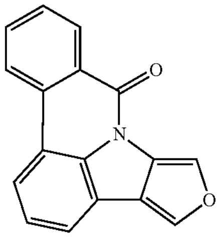 [SMILES: O=c1c2ccccc2c2cccc3c4cocc4n1c23] | 42% | 3e | 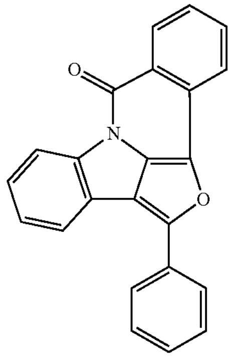 [SMILES: O=c1c2ccccc2c2oc(-c3ccccc3)c3c4ccccc4n1c23] | 21% |
| 3f | 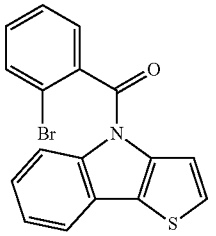 [SMILES: O=C(c1ccccc1Br)n1c2ccccc2c2sccc21] | 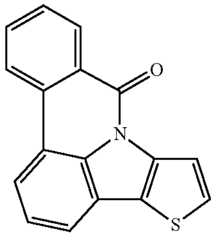 [SMILES: O=c1c2ccccc2c2cccc3c4sccc4n1c23] | 37% | 3g | 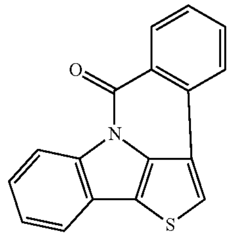 [SMILES: O=c1c2ccccc2c2csc3c4ccccc4n1c23] | 24% |
| 3h | 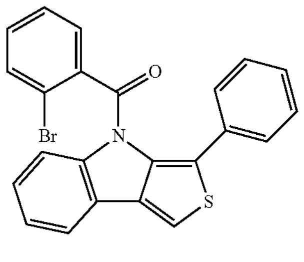 [SMILES: O=C(c1ccccc1Br)n1c2ccccc2c2csc(-c3ccccc3)c21] | 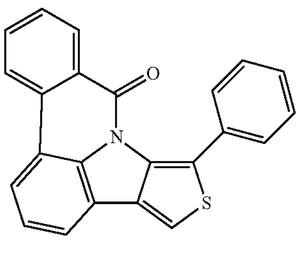 [SMILES: O=c1c2ccccc2c2cccc3c4csc(-c5ccccc5)c4n1c23] | 69% | | | |

-continued
| Ex. | Starting material 1 | Product 1 | Yield | Ex. | Product 2 | Yield |
|---|---|---|---|---|---|---|
| 3i | 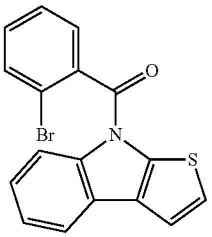 [SMILES: O=C(c1ccccc1Br)n1c2ccccc2c2ccsc21] | 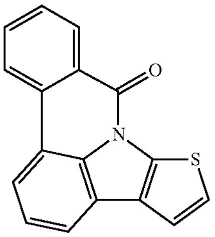 [SMILES: O=c1c2ccccc2c2cccc3c4ccsc4n1c23] | | | | |
| 3j | 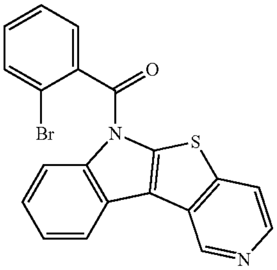 [SMILES: O=C(c1ccccc1Br)n1c2ccccc2c2c3cnccc3sc21] | 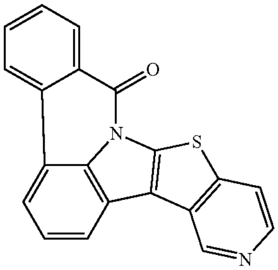 [SMILES: O=c1c2ccccc2c2cccc3c4c5cnccc5sc4n1c23] | 73% | | | |
| 3k | 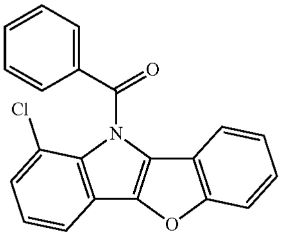 [SMILES: O=C(c1ccccc1)n1c2c(Cl)cccc2c2oc3ccccc3c21] | 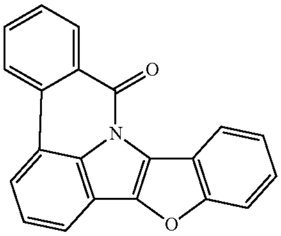 [SMILES: O=c1c2ccccc2c2cccc3c4oc5ccccc5c4n1c23] | 73% | | | |
| 3l | 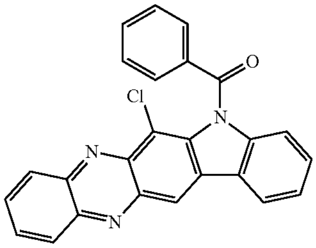 [SMILES: O=C(c1ccccc1)n1c2ccccc2c2cc3nc4ccccc4nc3c(Cl)c21] | 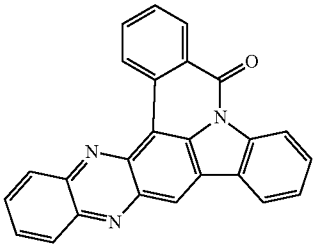 [SMILES: O=c1c2ccccc2c2c3nc4ccccc4nc3cc3c4ccccc4n1c32] | 73% | | | |
| 3m | 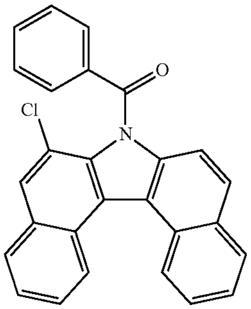 [SMILES: O=C(c1ccccc1)n1c2ccc3ccccc3c2c2c3ccccc3cc(Cl)c21] | 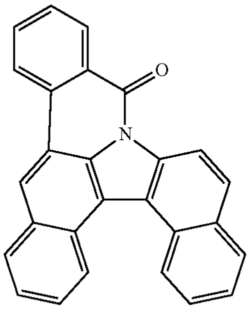 [SMILES: O=c1c2ccccc2c2cc3ccccc3c3c4c5ccccc5ccc4n1c23] | 73% | | | |

-continued

| Ex. | Starting material 1 | Product 1 | Yield | Ex. | Product 2 | Yield |
|---|---|---|---|---|---|---|
| 3n | 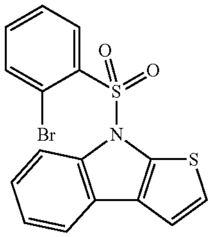 [SMILES: O=S(=O)(c1ccccc1Br)n1c2ccccc2c2ccsc21] | 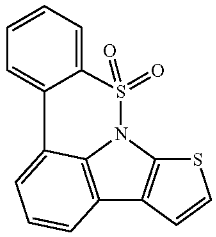 [SMILES: O=S1(=O)c2ccccc2-c2cccc3c4ccsc4n1c23] | 50% | | | |
| 3o | 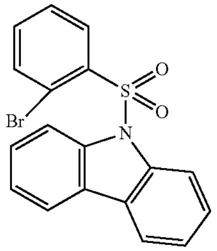 [SMILES: O=S(=O)(c1ccccc1Br)n1c2ccccc2c2ccccc21] | 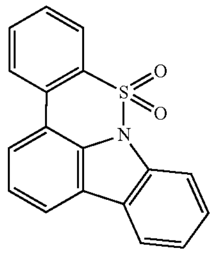 [SMILES: O=S1(=O)c2ccccc2-c2cccc3c4ccccc4n1c23] | 52% | | | |
| 3p | 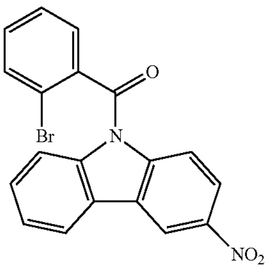 [SMILES: O=C(c1ccccc1Br)n1c2ccccc2c2cc([N+](=O)[O-])ccc21] | 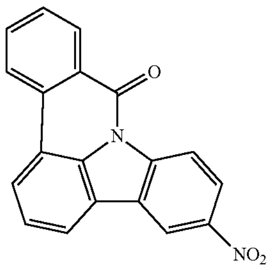 [SMILES: O=c1c2ccccc2c2cccc3c4cc([N+](=O)[O-])ccc4n1c23] | 53% | | | |
| 3q | 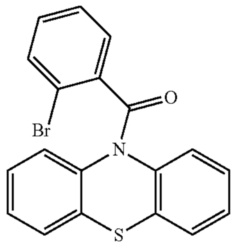 349144-33-8 | 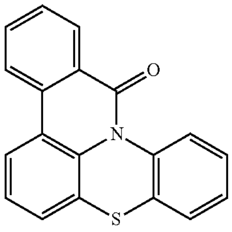 [SMILES: O=c1c2ccccc2c2cccc3c2n1-c1ccccc1S3] | 53% | | | |

Example 4a

Monobromination

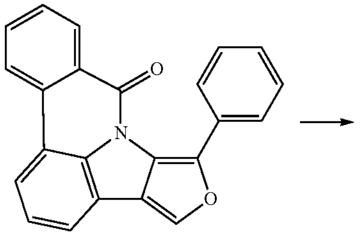

-continued

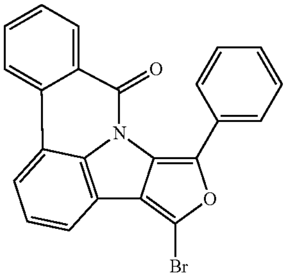

7.4 g (22.2 mmol) of 3a are initially introduced in 150 ml of $CH_2Cl_2$. A solution of 4 g (22.5 mmol) of NBS in 100 ml of acetonitrile is subsequently added dropwise at −15° C. with exclusion of light, the mixture is allowed to come to room temperature and is stirred at this temperature for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane and filtered off with suction. Yield: 7.3 g (17.7 mmol), 80% of theory, purity according to $^1$H-NMR about 97%.
The following compounds are obtained analogously:
| Ex. | Starting material 1 | Product 1 | Yield |
|---|---|---|---|
| 4b | 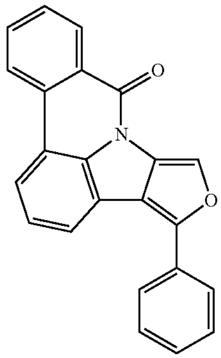 [SMILES: O=c1c2ccccc2c2cccc3c4c(-c5ccccc5)occ4n1c23] | 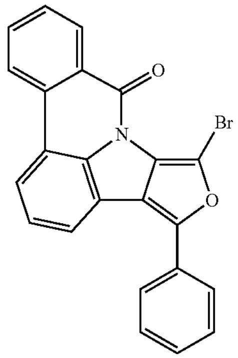 [SMILES: O=c1c2ccccc2c2cccc3c4c(-c5ccccc5)oc(Br)c4n1c23] | 65% |
| 4c | 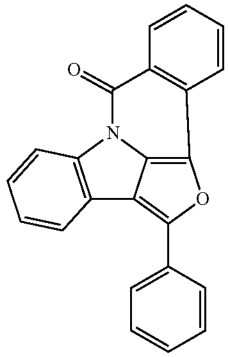 [SMILES: O=c1c2ccccc2c2oc(-c3ccccc3)c3c4ccccc4n1c23] | 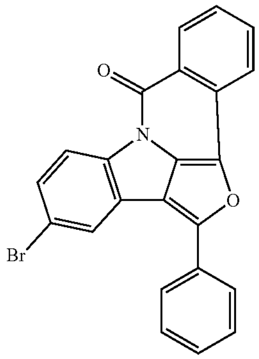 [SMILES: O=c1c2ccccc2c2oc(-c3ccccc3)c3c4cc(Br)ccc4n1c23] | 83% |
| 4d | 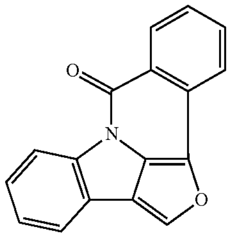 [SMILES: O=c1c2ccccc2c2occ3c4ccccc4n1c32] | 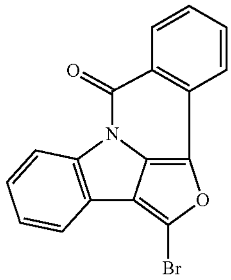 | 72% |
| 4e | 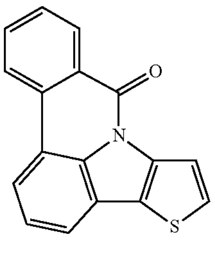 [SMILES: O=c1c2ccccc2c2cccc3c4sccc4n1c23] | 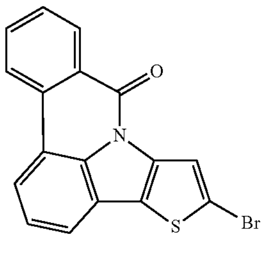 [SMILES: O=c1c2ccccc2c2cccc3c4sc(Br)cc4n1c23] | 64% |
| 4f | 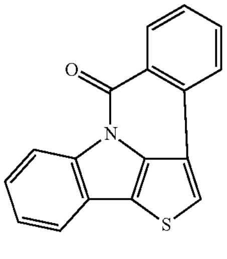 [SMILES: O=c1c2ccccc2c2csc3c4ccccc4n1c23] | 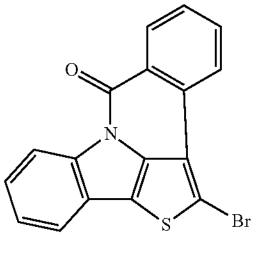 [SMILES: O=c1c2ccccc2c2c(Br)sc3c4ccccc4n1c32] | 87% |

-continued
| Ex. | Starting material 1 | Product 1 | Yield |
|---|---|---|---|
| 4g | 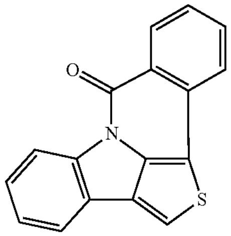 [SMILES: O=c1c2ccccc2c2scc3c4ccccc4n1c32] | 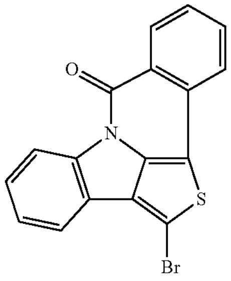 [SMILES: O=c1c2ccccc2c2sc(Br)c3c4ccccc4n1c23] | 66% |
| 4h | 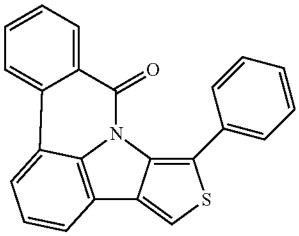 [SMILES: O=c1c2ccccc2c2cccc3c4csc(-c5ccccc5)c4n1c23] | 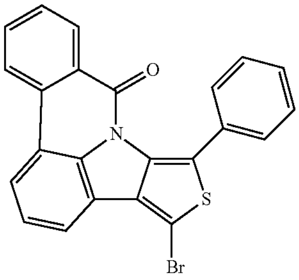 [SMILES: O=c1c2ccccc2c2cccc3c4c(Br)sc(-c5ccccc5)c4n1c23] | 43% |
| 4i | 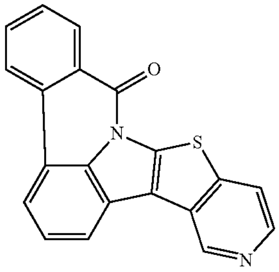 [SMILES: O=c1c2ccccc2c2cccc3c4c5cnccc5sc4n1c23] | 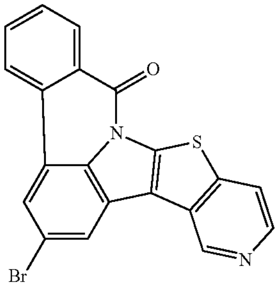 [SMILES: O=c1c2ccccc2c2cc(Br)cc3c4c5cnccc5sc4n1c23] | 92% |
| 4j | 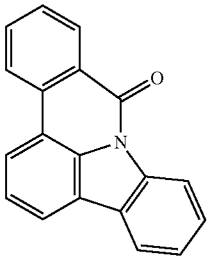 Tetrahedron (1989), 45(12), 3775-86 | 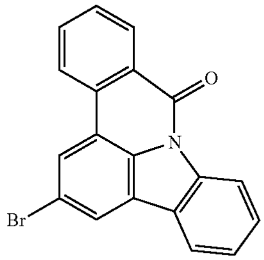 [SMILES: O=c1c2ccccc2c2cc(Br)cc3c4ccccc4n1c23] | 48% |
| 4k | 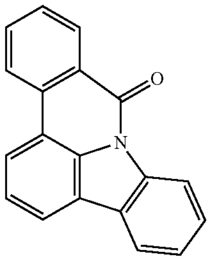 [SMILES: O=c1c2ccccc2c2cccc3c4ccccc4n1c23] | 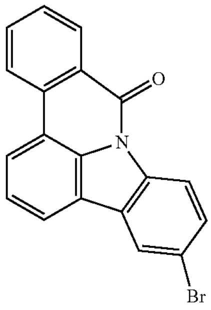 [SMILES: O=c1c2ccccc2c2cccc3c4cc(Br)ccc4n1c23] | 32% |

-continued
| Ex. | Starting material 1 | Product 1 | Yield |
|---|---|---|---|
| 4l | 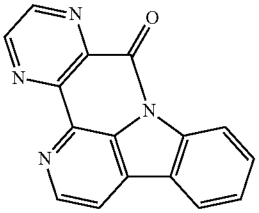<br>Journal of Natural Products (2005), 68(11), 1581-1587 | 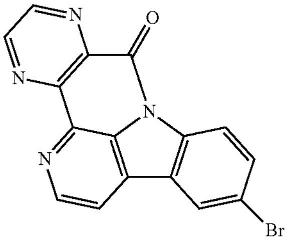 [SMILES: O=c1c2nccnc2c2nccc3c4cc(Br)ccc4n1c32] | 64% |
| 4m | 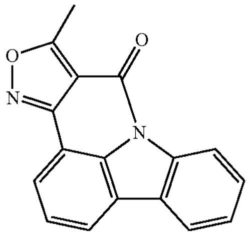<br>International Electronic Conference on Synthetic Organic Chemistry, 9th, Nov. 1-30, 2005 | 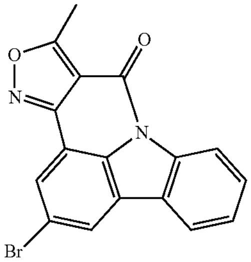 [SMILES: Cc1onc2c1c(=O)n1c3ccccc3c3cc(Br)cc2c31] | 67% |
| 4n | 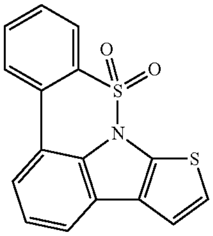 [SMILES: O=S1(=O)c2ccccc2-c2cccc3c4ccsc4n1c23] | 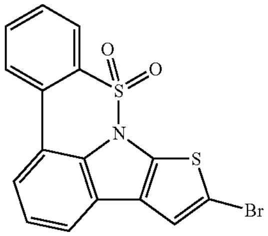 [SMILES: O=S1(=O)c2ccccc2-c2cccc3c4cc(Br)sc4n1c23] | 60% |
| 4o | 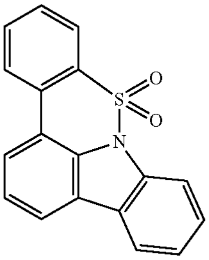 [SMILES: O=S1(=O)c2ccccc2-c2cccc3c4ccccc4n1c23] | 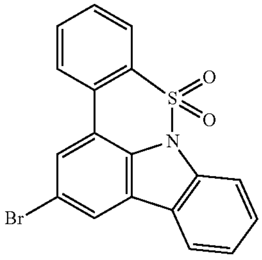 [SMILES: O=S1(=O)c2ccccc2-c2cc(Br)cc3c4ccccc4n1c23] | 79% |
| 4p | 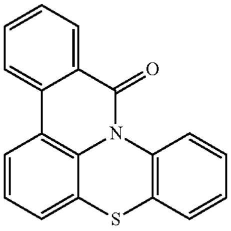 [SMILES: O=c1c2ccccc2c2cccc3c2n1-c1ccccc1S3] | 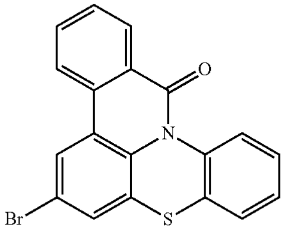 [SMILES: O=c1c2ccccc2c2cc(Br)cc3c2n1-c1ccccc1S3] | 49% |

Example 4q

Dibromination

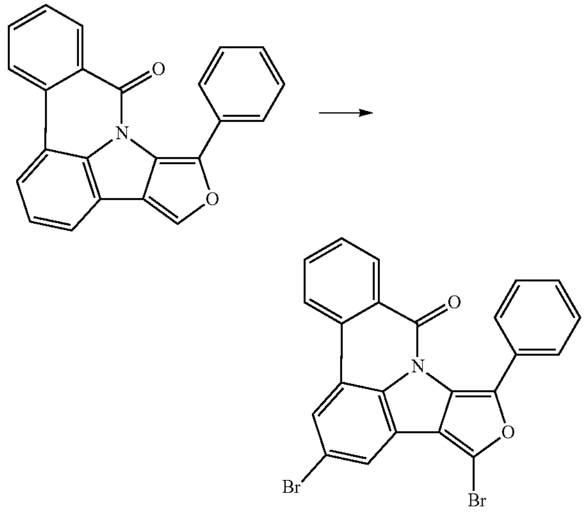

7.4 g (22.2 mmol) of 3a are initially introduced in 150 ml of $CH_2Cl_2$. A solution of 8 g (45.1 mmol) of NBS in 100 ml of acetonitrile is subsequently added dropwise at 60° C. with exclusion of light, the mixture is allowed to come to room temperature and is stirred at this temperature for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane and filtered off with suction. Yield: 10.3 g (17.7 mmol), 95% of theory, purity according to $^1$H-NMR about 97%.

The following compounds are obtained analogously:

| Ex. | Starting material 1 | Product 1 | Yield |
|---|---|---|---|
| 4r | 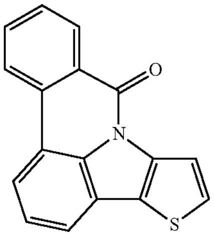 [SMILES: O=c1c2ccccc2c2cccc3c4sccc4n1c23] | 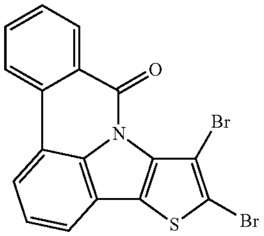 [SMILES: O=c1c2ccccc2c2cccc3c4sc(Br)c(Br)c4n1c23] | 79% |
| 4s | 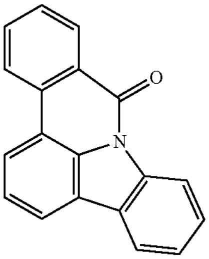 [SMILES: O=c1c2ccccc2c2cccc3c4ccccc4n1c23] | 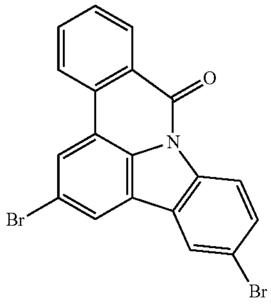 [SMILES: O=c1c2ccccc2c2cc(Br)cc3c4cc(Br)ccc4n1c23] | 87% |
| 4t | 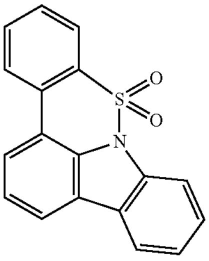 [SMILES: O=S1(=O)c2ccccc2-c2cccc3c4ccccc4n1c23] | 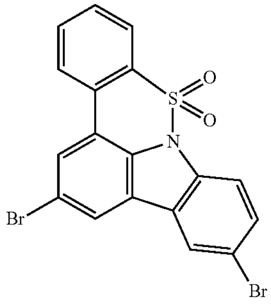 [SMILES: O=S1(=O)c2ccccc2-c2cc(Br)cc3c4cc(Br)ccc4n1c23] | 77% |

-continued

| Ex. | Starting material 1 | Product 1 | Yield |
|---|---|---|---|
| 4u | 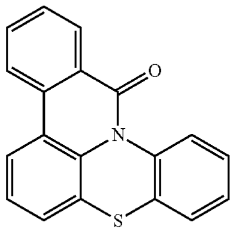 [SMILES: O=c1c2ccccc2c2cccc3c2n1-c1ccccc1S3] | 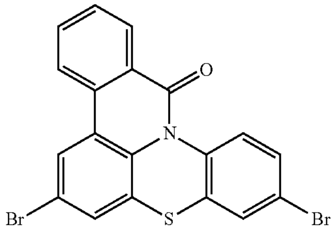 [SMILES: O=c1c2ccccc2c2cc(Br)cc3c2n1-c1ccc(Br)cc1S3] | 84% |

Example 5a

Reduction

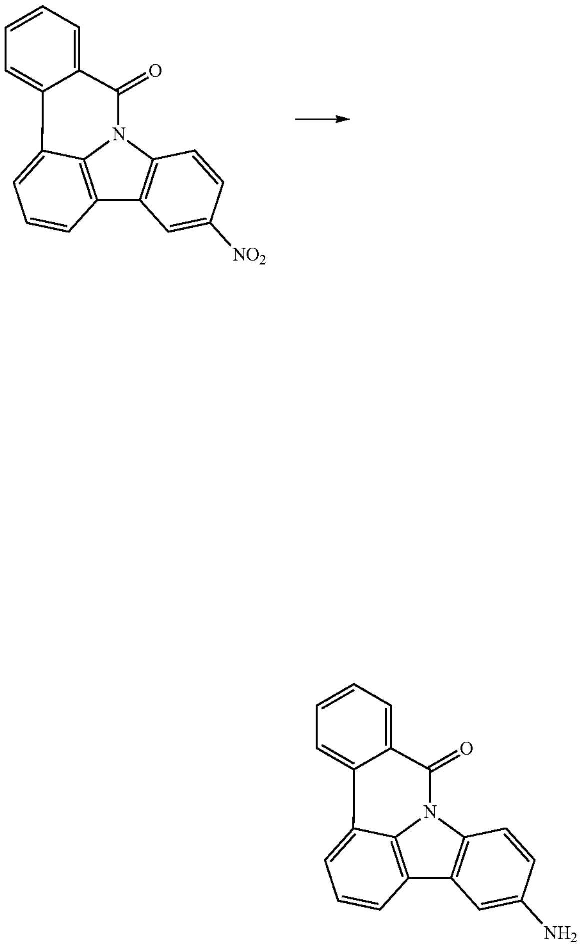

68.8 g (219 mmol) of 3m are dissolved in 820 ml of EtOH, 143 g (755 mmol) of $SnCl_2$ are added at room temperature, the mixture is heated under reflux for 6 h, allowed to come to room temperature over the course of 1 h, 20% NaOH is added. After phase separation, the solvent is removed, and the residue is purified by chromatography. The yield is 43 g (151 mmol), corresponding to 70%.

The following compounds are obtained analogously:

| Ex. | Starting material 1 | Product 1 | Yield |
|---|---|---|---|
| 5b | 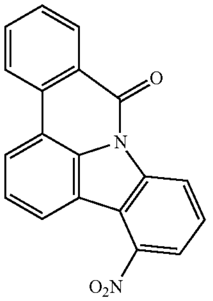 Organic Letters, 6(17), 2993-2996; 2004 | 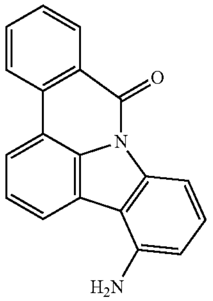 [SMILES: Nc1cccc2c1c1cccc3c4ccccc4c(=O)n2c31] | 81% |
| 5c | 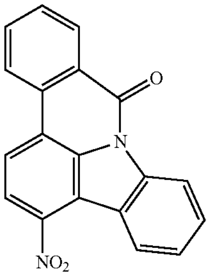 Organic Letters, 6(17), 2993-2996; 2004 | 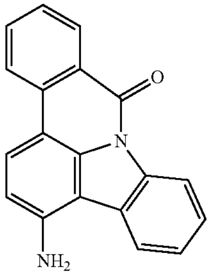 [SMILES: Nc1ccc2c3ccccc3c(=O)n3c4ccccc4c1c23] | 77% |

Example 6a

Carbazole Formation

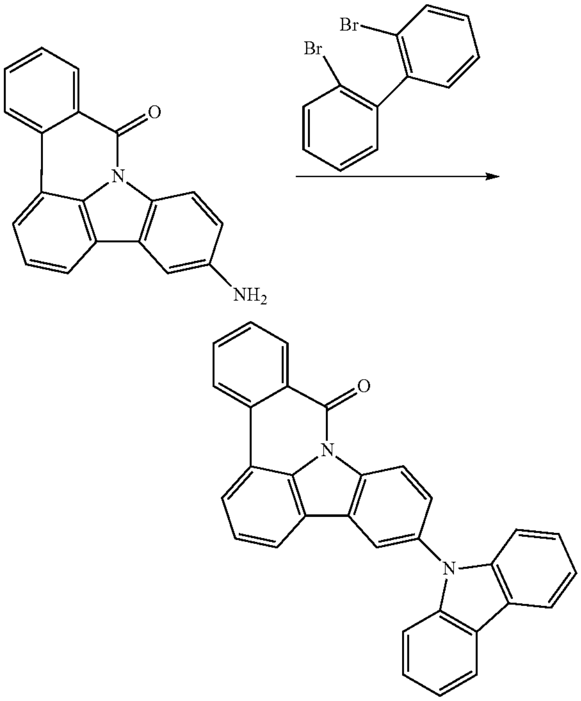

6.5 g (23 mmol) of 5-amino-7b-azabenzo[e]acephenanthrylen-8-one, 7.1 g (23 mmol) of 2,2'-dibromodiphenyl, 16 g (72 mmol) of NaOtBu, 1.4 g (1.58 mmol) of $Pd_2$ $dba_3$ and 6.3 ml (6.3 mmol) of t-$Bu_3P$ are heated at 110° C. for 36 h in 150 ml of toluene under a protective-gas atmosphere. After cooling, the precipitated solid is filtered off with suction, washed with water and ethanol and dried. The residue is extracted with hot toluene, recrystallised from toluene and finally sublimed in a high vacuum. The yield after sublimation is 7 g (16 mmol, 71%) with a purity of 99.9%.

The following compounds are obtained analogously:

| Ex. | Starting material 1 | Product 1 | Yield |
|---|---|---|---|
| 6b | 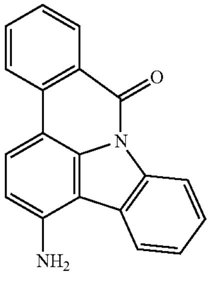 [SMILES: Nc1ccc2c3ccccc3c(=O)n3c4ccccc4c1c23] | 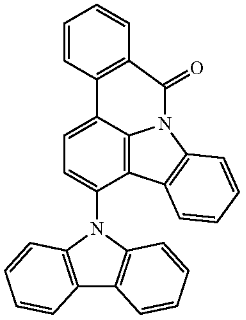 [SMILES: O=c1c2ccccc2c2ccc(-n3c4ccccc4c4ccccc43)c3c4ccccc4n1c23] | 62% |

-continued

| Ex. | Starting material 1 | Product 1 | Yield |
|---|---|---|---|
| 6c | 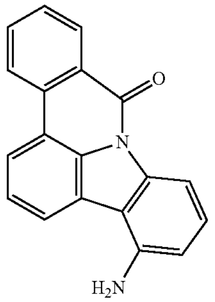 [SMILES: Nc1cccc2c1c1cccc3c4ccccc4c(=O)n2c31] | 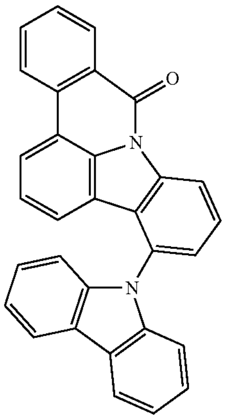 [SMILES: O=c1c2ccccc2c2cccc3c4c(-n5c6ccccc6c6ccccc65)cccc4n1c23] | 65% |

Example 7a

Hartwig-Buchwald Reaction

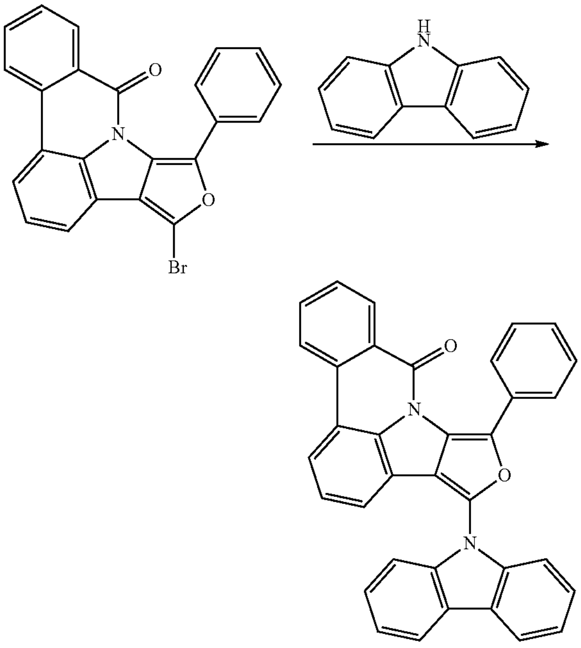

13.9 g (33.7 mmol) of 4a, 4.2 g (37.6 mmol) of carbazole and 23.34 g of $Rb_2CO_3$ are suspended in 200 ml of p-xylene. 0.76 g (3.4 mmol) of $Pd(OAc)_2$ and 10.1 ml of a 1M tri-tert-butylphosphine solution are added to this suspension. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum, purity is 99.9%.

Yield: 12.6 g (25 mmol), 75% of theory.

The following compounds are obtained analogously:
| Ex. | Starting material 1 | Starting material 2 |
|---|---|---|
| 7b | 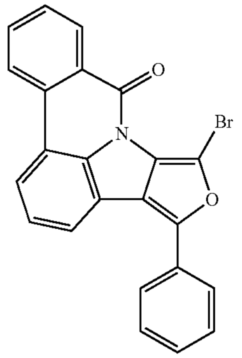 [SMILES: O=c1c2ccccc2c2cccc3c4c(-c5ccccc5)oc(Br)c4n1c23] | 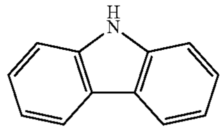 [SMILES: c1ccc2c(c1)[nH]c1ccccc12] |
| 7c | 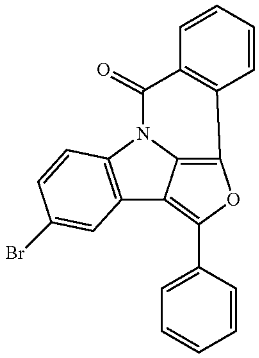 [SMILES: O=c1c2ccccc2c2oc(-c3ccccc3)c3c4cc(Br)ccc4n1c23] | 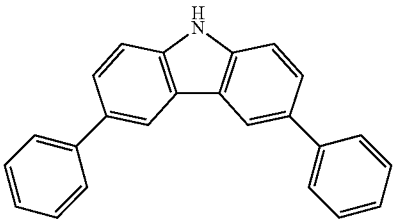 [SMILES: c1ccc(-c2ccc3[nH]c4ccc(-c5ccccc5)cc4c3c2)cc1] |
| 7d | 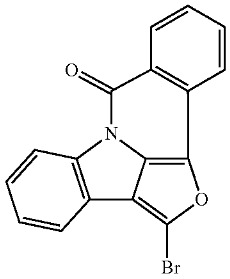 [SMILES: O=c1c2ccccc2c2oc(Br)c3c4ccccc4n1c23] | 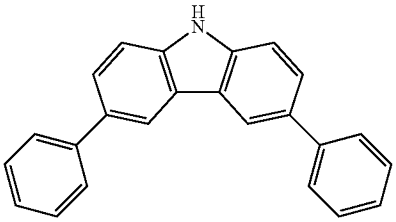 [SMILES: c1ccc(-c2ccc3[nH]c4ccc(-c5ccccc5)cc4c3c2)cc1] |
| 7e | 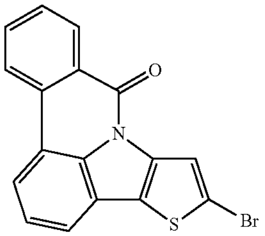 [SMILES: O=c1c2ccccc2c2cccc3c4sc(Br)cc4n1c23] | 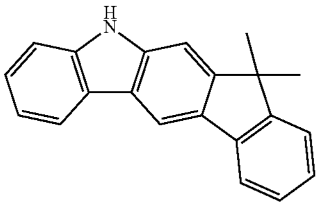 [SMILES: CC1(C)c2ccccc2-c2cc3c(cc21)[nH]c1ccccc13] |
| 7f | 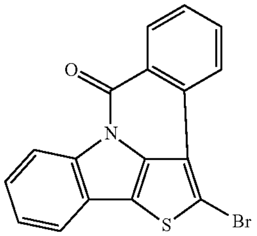 [SMILES: O=c1c2ccccc2c2c(Br)sc3c4ccccc4n1c32] | 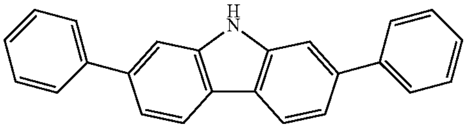 [SMILES: c1ccc(-c2ccc3c(c2)[nH]c2cc(-c4ccccc4)ccc23)cc1] |

-continued
7g
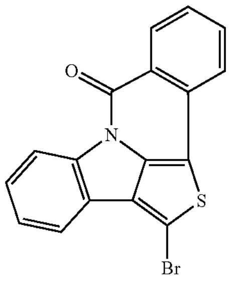 [SMILES: O=c1c2ccccc2c2sc(Br)c3c4ccccc4n1c23]
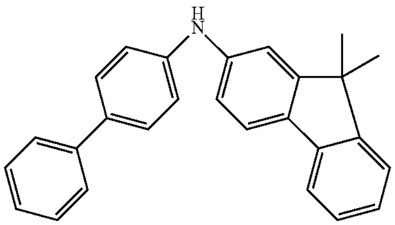 [SMILES: CC1(C)c2ccccc2-c2ccc(Nc3ccc(-c4ccccc4)cc3)cc21]
7h
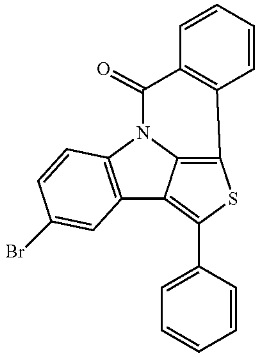 [SMILES: O=c1c2ccccc2c2sc(-c3ccccc3)c3c4cc(Br)ccc4n1c23]
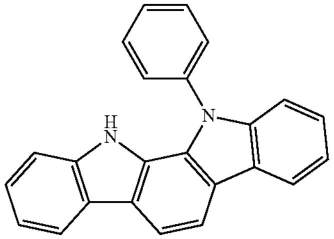 [SMILES: c1ccc(-n2c3ccccc3c3ccc4c5ccccc5[nH]c4c32)cc1]
7i
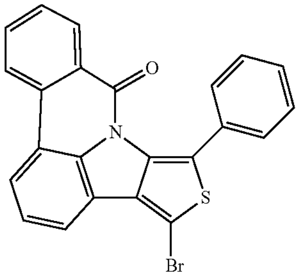 [SMILES: O=c1c2ccccc2c2cccc3c4c(Br)sc(-c5ccccc5)c4n1c23]
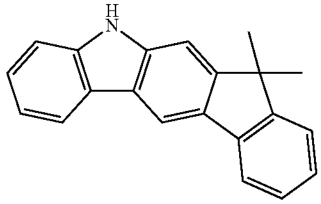 [SMILES: CC1(C)c2ccccc2-c2cc3c(cc21)[nH]c1ccccc13]
7j
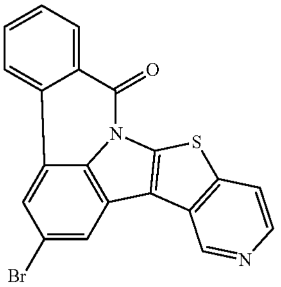 [SMILES: O=c1c2ccccc2c2cc(Br)cc3c4c5cnccc5sc4n1c23]
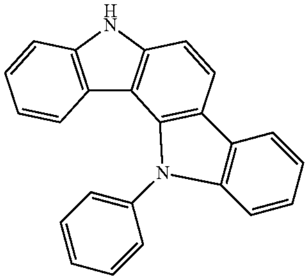 [SMILES: c1ccc(-n2c3ccccc3c3ccc4[nH]c5ccccc5c4c32)cc1]
7k
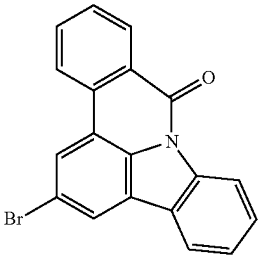 [SMILES: O=c1c2ccccc2c2cc(Br)cc3c4ccccc4n1c23]
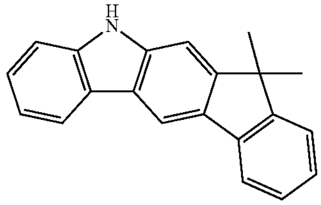 [SMILES: CC1(C)c2ccccc2-c2cc3c(cc21)[nH]c1ccccc13]

-continued
| | | |
|---|---|---|
| 7l | 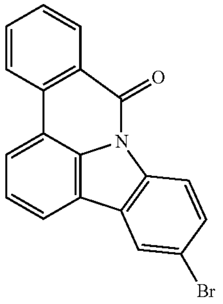 [SMILES: O=c1c2ccccc2c2cccc3c4cc(Br)ccc4n1c23] | 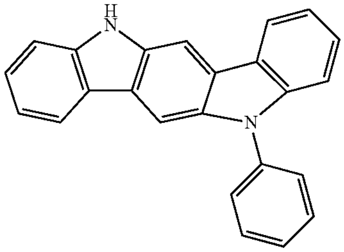 [SMILES: c1ccc(-n2c3ccccc3c3cc4[nH]c5ccccc5c4cc32)cc1] |
| 7m | 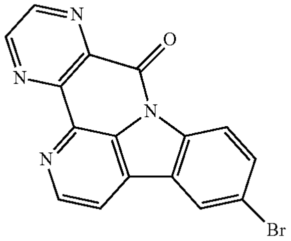 [SMILES: O=c1c2nccnc2c2nccc3c4cc(Br)ccc4n1c32] | 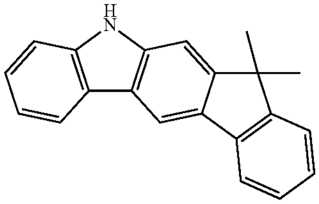 [SMILES: CC1(C)c2ccccc2-c2cc3c(cc21)[nH]c1ccccc13] |
| 7n | 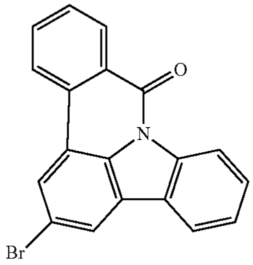 [SMILES: O=c1c2ccccc2c2cc(Br)cc3c4ccccc4n1c23] | 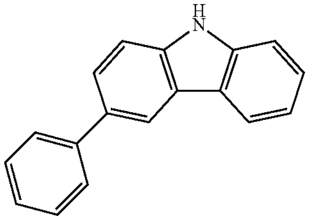 [SMILES: c1ccc(-c2ccc3[nH]c4ccccc4c3c2)cc1] |
| 7o | 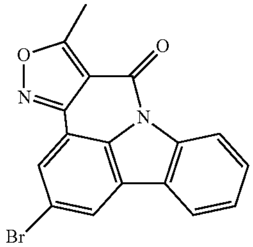 [SMILES: Cc1onc2c1c(=O)n1c3ccccc3c3cc(Br)cc2c31] | 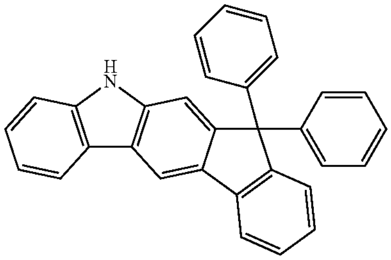 [SMILES: c1ccc(C2(c3ccccc3)c3ccccc3-c3cc4c(cc32)[nH]c2ccccc24)cc1] |
| 7p | 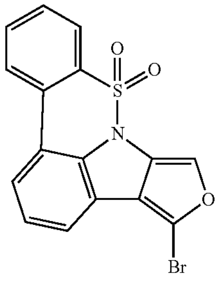 [SMILES: O=S1(=O)c2ccccc2-c2cccc3c4c(Br)occ4n1c23] | 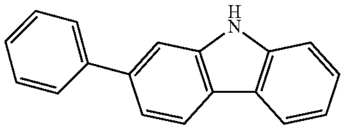 [SMILES: c1ccc(-c2ccc3c(c2)[nH]c2ccccc23)cc1] |
| 7q | 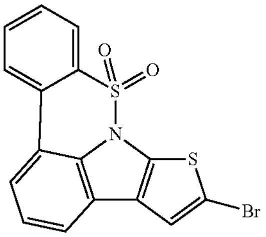 [SMILES: O=S1(=O)c2ccccc2-c2cccc3c4cc(Br)sc4n1c23] | 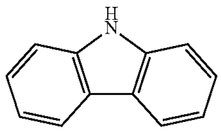 [SMILES: c1ccc2c(c1)[nH]c1ccccc12] |

-continued
7r
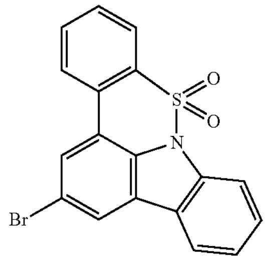 [SMILES: O=S1(=O)c2ccccc2-c2cc(Br)cc3c4ccccc4n1c23]
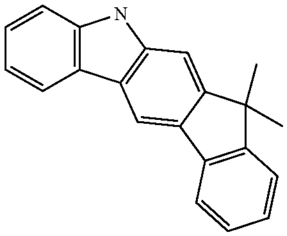 [SMILES: CC1(C)c2ccccc2-c2cc3c(cc21)[nH]c1ccccc13]
7s
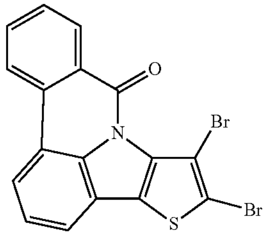 [SMILES: O=c1c2ccccc2c2cccc3c4sc(Br)c(Br)c4n1c23]
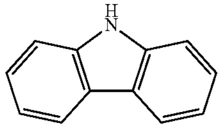 [SMILES: c1ccc2c(c1)[nH]c1ccccc12]
7t
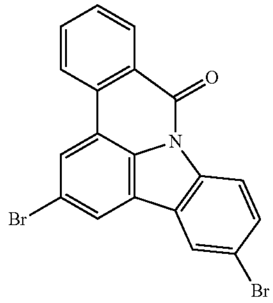 [SMILES: O=c1c2ccccc2c2cc(Br)cc3c4cc(Br)ccc4n1c23]
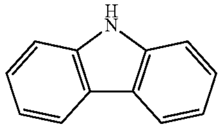 [SMILES: c1ccc2c(c1)[nH]c1ccccc12]
7u
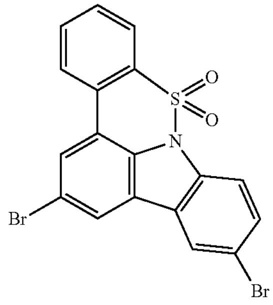 [SMILES: O=S1(=O)c2ccccc2-c2cc(Br)cc3c4cc(Br)ccc4n1c23]
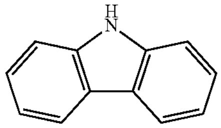 [SMILES: c1ccc2c(c1)[nH]c1ccccc12]
7v
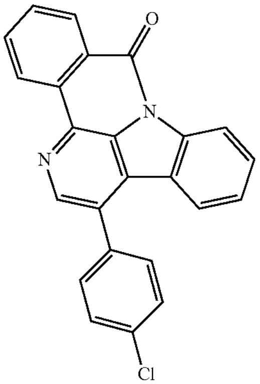
904503-77-1
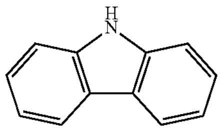 [SMILES: c1ccc2c(c1)[nH]c1ccccc12]

-continued
| | | |
|---|---|---|
| 7w | 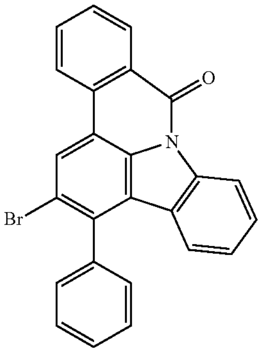<br>Australian Journal of Chemistry (1970), 23(1), 185-91. | 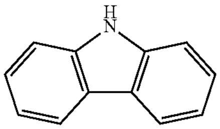 [SMILES: c1ccc2c(c1)[nH]c1ccccc12] |
| 7y | 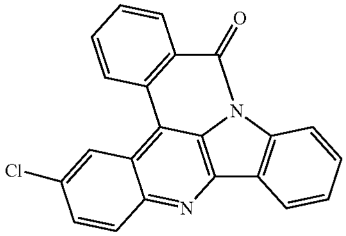<br>Helvetica Chimica Acta (1949), 32 1214-27. | 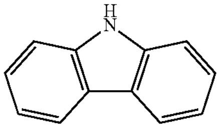 [SMILES: c1ccc2c(c1)[nH]c1ccccc12] |
| 7z | 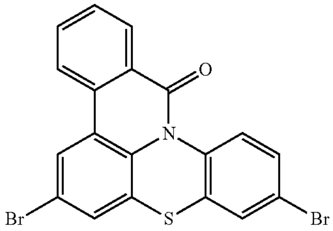 [SMILES: O=c1c2ccccc2c2cc(Br)cc3c2n1-c1ccc(Br)cc1S3] | 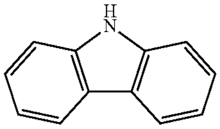 [SMILES: c1ccc2c(c1)[nH]c1ccccc12] |
| Ex. | Product | Yield. |
|---|---|---|
| 7b | 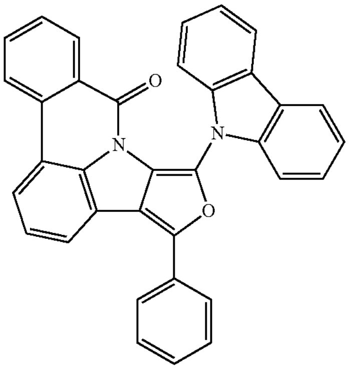 [SMILES: O=c1c2ccccc2c2cccc3c4c(-c5ccccc5)oc(-n5c6ccccc6c6ccccc65)c4n1c23] | 63% |

-continued
7c
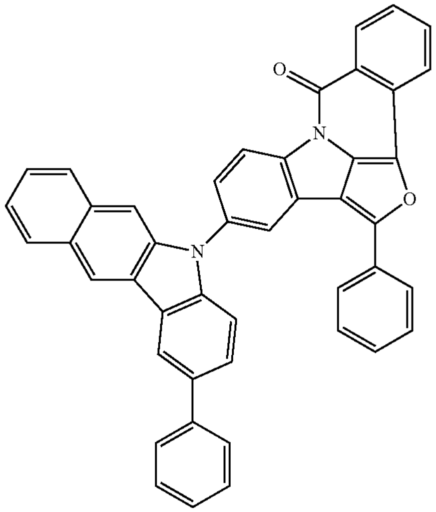 [SMILES: O=c1c2ccccc2c2oc(-c3ccccc3)c3c4cc(-n5c6ccc(-c7ccccc7)cc6c6cc7ccccc7cc65)ccc4n1c23]
56%
7d
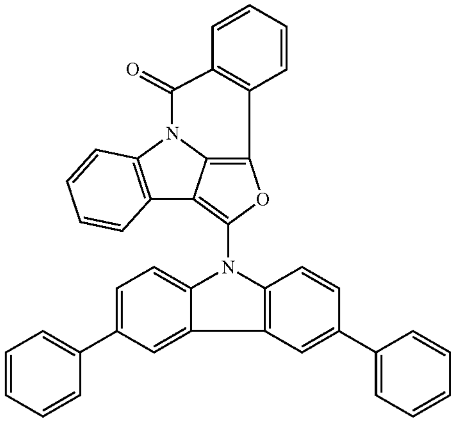 [SMILES: O=c1c2ccccc2c2oc(-n3c4ccc(-c5ccccc5)cc4c4cc(-c5ccccc5)ccc43)c3c4ccccc4n1c23]
72%
7e
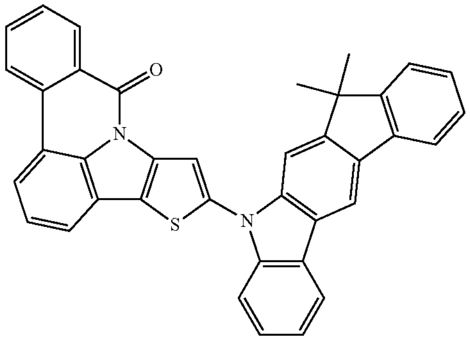 [SMILES: CC1(C)c2ccccc2-c2cc3c4ccccc4n(-c4cc5c(s4)c4cccc6c7ccccc7c(=O)n5c64)c3cc21]
67%

-continued
| | | |
|---|---|---|
| 7f | 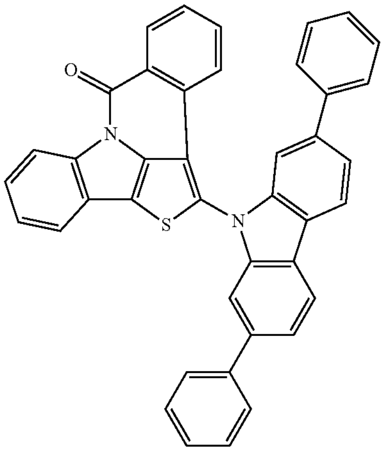 [SMILES: O=c1c2ccccc2c2c(-n3c4cc(-c5ccccc5)ccc4c4ccc(-c5ccccc5)cc43)sc3c4ccccc4n1c32] | 59% |
| 7g | 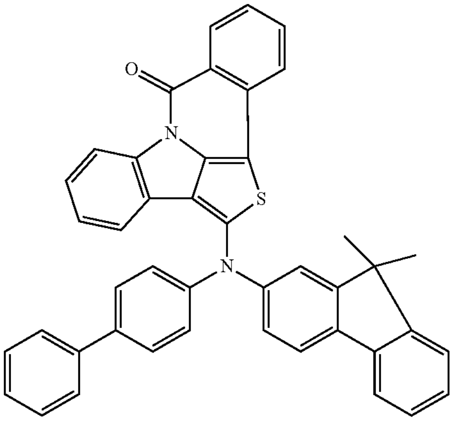 [SMILES: CC1(C)c2ccccc2-c2ccc(N(c3ccc(-c4ccccc4)cc3)c3sc4c5ccccc5c(=O)n5c6ccccc6c3c45)cc21] | 65% |
| 7h | 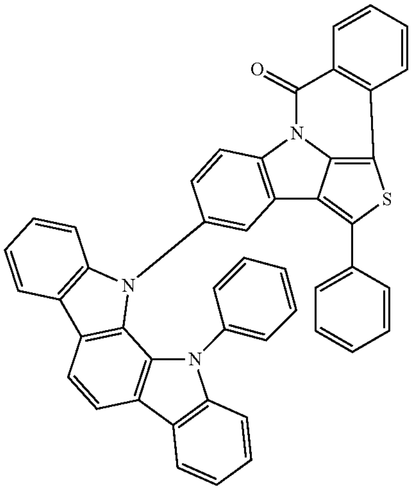 [SMILES: O=c1c2ccccc2c2sc(-c3ccccc3)c3c4cc(-n5c6ccccc6c6ccc7c8ccccc8n(-c8ccccc8)c7c65)ccc4n1c23] | 79% |

-continued
7i 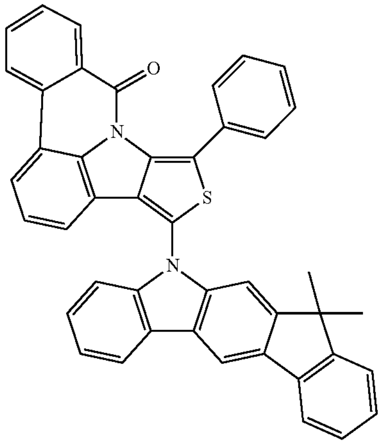 [SMILES: CC1(C)c2ccccc2-c2cc3c4ccccc4n(-c4sc(-c5ccccc5)c5c4c4cccc6c7ccccc7c(=O)n5c64)c3cc21] 80%
7j 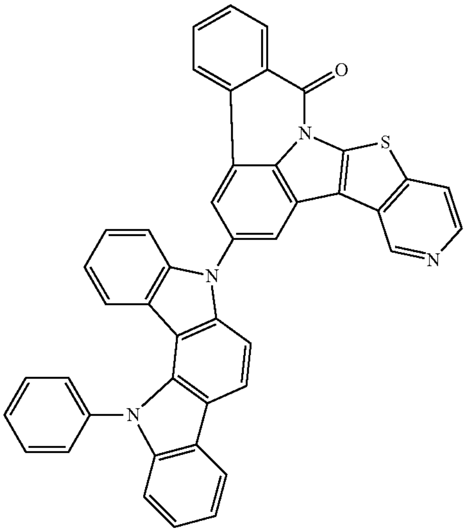 [SMILES: O=c1c2ccccc2c2cc(-n3c4ccccc4c4c3ccc3c5ccccc5n(-c5ccccc5)c34)cc3c4c5cnccc5sc4n1c23] 83%
7k 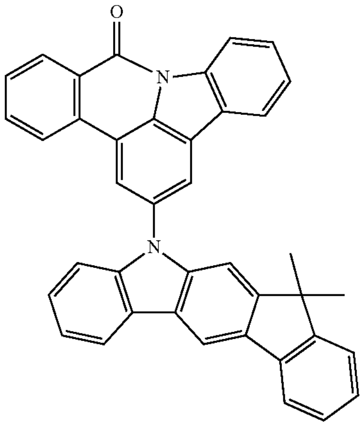 [SMILES: CC1(C)c2ccccc2-c2cc3c4ccccc4n(-c4cc5c6ccccc6c(=O)n6c7ccccc7c(c4)c56)c3cc21] 67%

-continued
7l
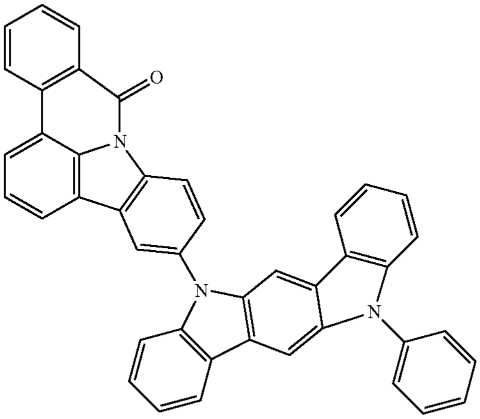 [SMILES: O=c1c2ccccc2c2cccc3c4cc(-n5c6ccccc6c6cc7c(cc65)c5ccccc5n7-c5ccccc5)ccc4n1c23]
77%
7m
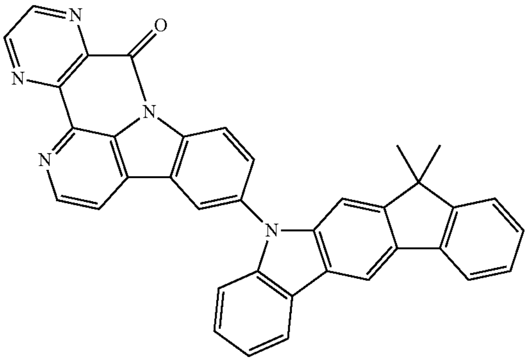 [SMILES: CC1(C)c2ccccc2-c2cc3c4ccccc4n(-c4ccc5c(c4)c4ccnc6c7nccnc7c(=O)n5c46)c3cc21]
69%
7n
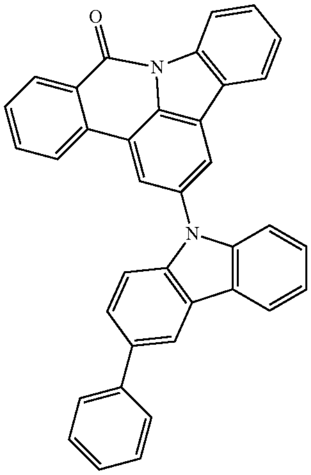 [SMILES: O=c1c2ccccc2c2cc(-n3c4ccccc4c4cc(-c5ccccc5)ccc43)cc3c4ccccc4n1c23]
69%
7o
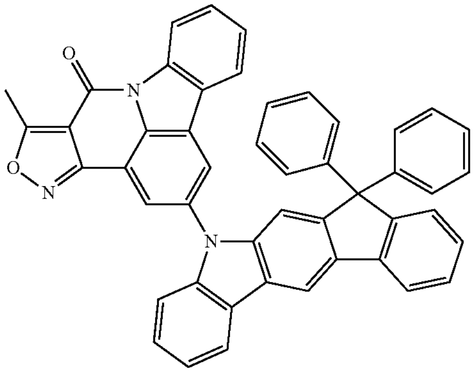 [SMILES: Cc1onc2c1c(=O)n1c3ccccc3c3cc(-n4c5ccccc5c5cc6c(cc54)C(c4ccccc4)(c4ccccc4)c4ccccc4-6)cc2c31]
67%

-continued
7p 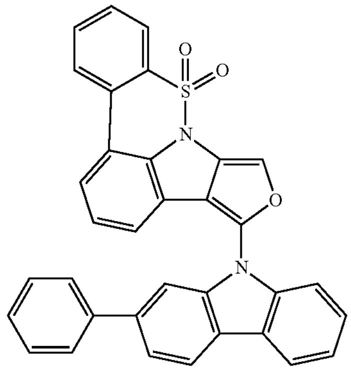 [SMILES: O=S1(=O)c2ccccc2-c2cccc3c4c(-n5c6ccccc6c6ccc(-c7ccccc7)cc65)occ4n1c23] 59%
7q 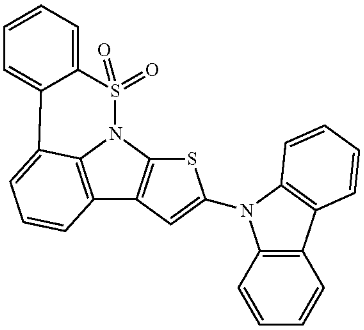 [SMILES: O=S1(=O)c2ccccc2-c2cccc3c4cc(-n5c6ccccc6c6ccccc65)sc4n1c23] 57%
7r 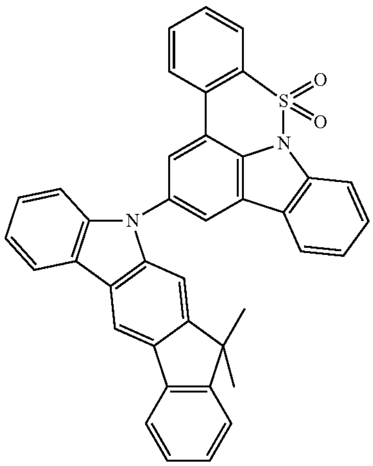 [SMILES: CC1(C)c2ccccc2-c2cc3c4ccccc4n(-c4cc5c6c(c4)c4ccccc4n6S(=O)(=O)c4ccccc4-5)c3cc21] 58%
7s 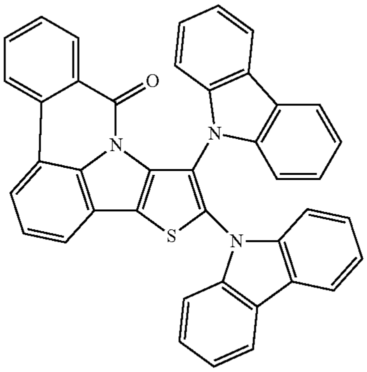 [SMILES: O=c1c2ccccc2c2cccc3c4sc(-n5c6ccccc6c6ccccc65)c(-n5c6ccccc6c6ccccc65)c4n1c23] 58%

-continued
| | | |
|---|---|---|
| 7t | 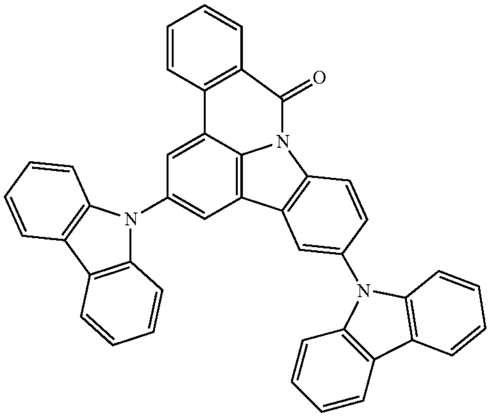 [SMILES: O=c1c2ccccc2c2cc(-n3c4ccccc4c4ccccc43)cc3c4cc(-n5c6ccccc6c6ccccc65)ccc4n1c23] | 67% |
| 7u | 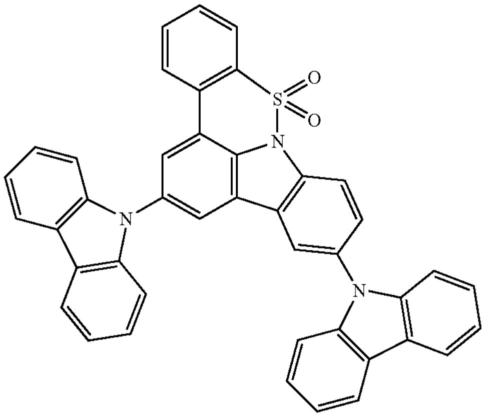 [SMILES: O=S1(=O)c2ccccc2-c2cc(-n3c4ccccc4c4ccccc43)cc3c4cc(-n5c6ccccc6c6ccccc65)ccc4n1c23] | 83% |
| 7v | 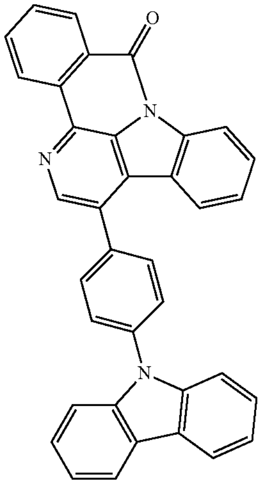 [SMILES: O=c1c2ccccc2c2ncc(-c3ccc(-n4c5ccccc5c5ccccc54)cc3)c3c4ccccc4n1c23] | 82% |

-continued

| | | |
|---|---|---|
| 7w | 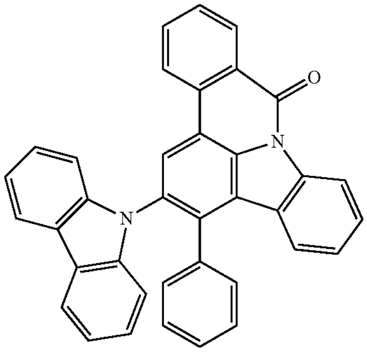 [SMILES: O=c1c2ccccc2c2cc(-n3c4ccccc4c4ccccc43)c(-c3ccccc3)c3c4ccccc4n1c23] | 70% |
| 7y | 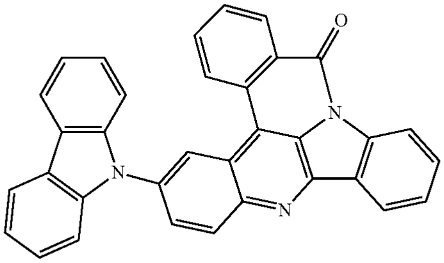 [SMILES: O=c1c2ccccc2c2c3cc(-n4c5ccccc5c5ccccc54)ccc3nc3c4ccccc4n1c32] | 73% |
| 7z | 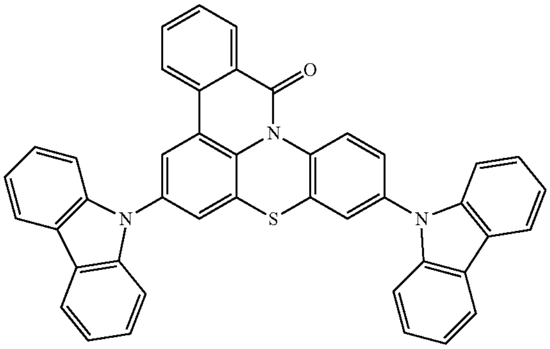 [SMILES: O=c1c2ccccc2c2cc(-n3c4ccccc4c4ccccc43)cc3c2n1-c1ccc(-n2c4ccccc4c4ccccc42)cc1S3] | |

Example 8a

Suzuki Reaction

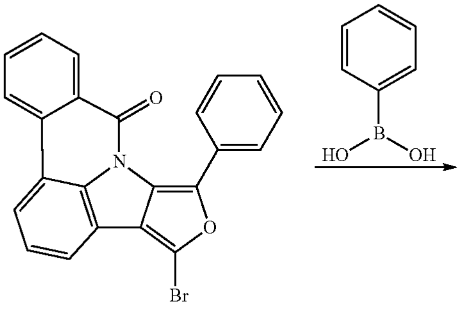

-continued

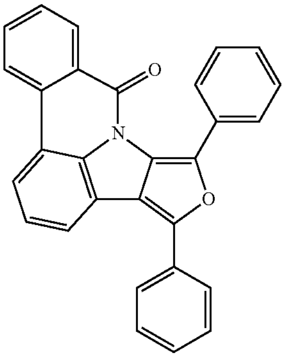

13.3 g (110.0 mmol) of phenylboronic acid, 45 g (110.0 mmol) of 4a and 44.6 g (210.0 mmol) of tripotassium phosphate are suspended in 500 ml of toulene, 500 ml of dioxane and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum, purity is 99.9%. The yield is 37 g (90 mmol), corresponding to 83% of theory.
The following compounds are obtained analogously:
| Ex. | Starting material 1 | Starting material 2 | Product | Yield. |
|---|---|---|---|---|
| 8b | 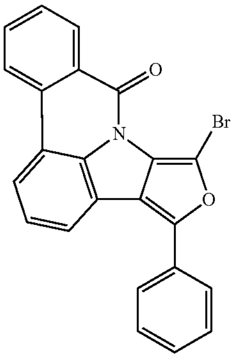 [SMILES: O=c1c2ccccc2c2cccc3c4c(-c5ccccc5)oc(Br)c4n1c23] | 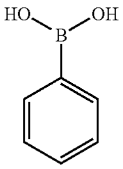 | 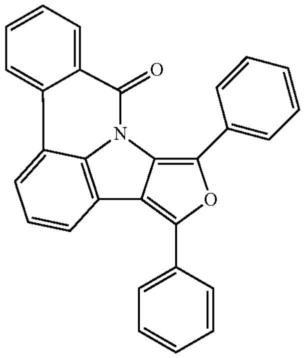 [SMILES: O=c1c2ccccc2c2cccc3c4c(-c5ccccc5)oc(-c5ccccc5)c4n1c23] | 70% |
| 8c | 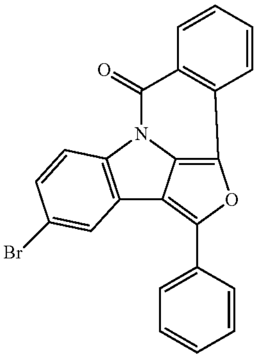 [SMILES: O=c1c2ccccc2c2oc(-c3ccccc3)c3c4cc(Br)ccc4n1c23] | 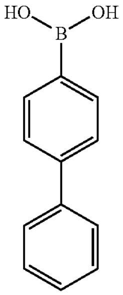 | 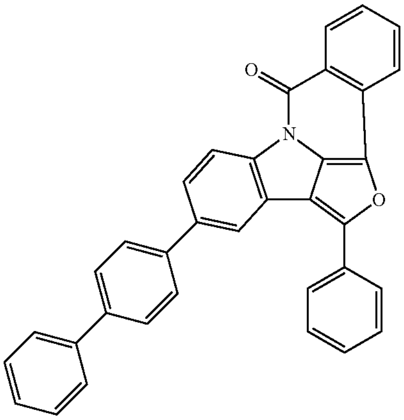 [SMILES: O=c1c2ccccc2c2oc(-c3ccccc3)c3c4cc(-c5ccc(-c6ccccc6)cc5)ccc4n1c23] | 75% |
| 8d | 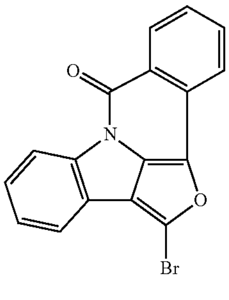 [SMILES: O=c1c2ccccc2c2oc(Br)c3c4ccccc4n1c23] | 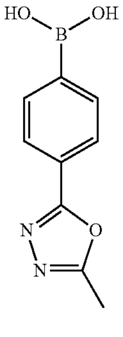 | 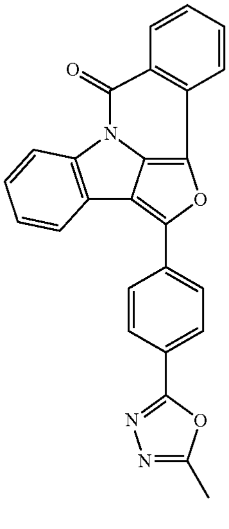 [SMILES: Cc1nnc(-c2ccc(-c3oc4c5ccccc5c(=O)n5c6ccccc6c3c45)cc2)o1] | 72% |

-continued
| Ex. | Starting material 1 | Starting material 2 | Product | Yield. |
| --- | --- | --- | --- | --- |
| 8e | 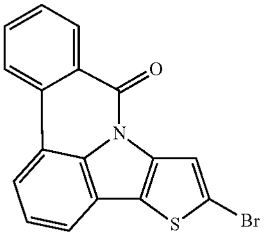 [SMILES: O=c1c2ccccc2c2cccc3c4sc(Br)cc4n1c23] | 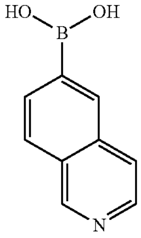 [SMILES: OB(O)c1ccc2cnccc2c1] | 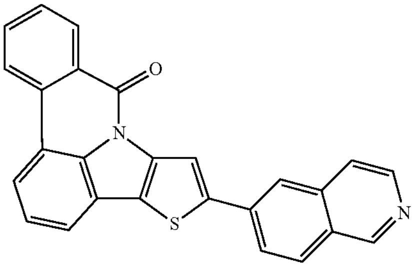 [SMILES: O=c1c2ccccc2c2cccc3c4sc(-c5ccc6cnccc6c5)cc4n1c23] | 69% |
| 8f | 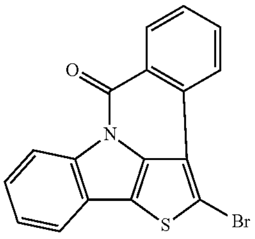 [SMILES: O=c1c2ccccc2c2c(Br)sc3c4ccccc4n1c32] | 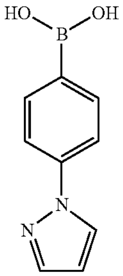 [SMILES: OB(O)c1ccc(-n2cccn2)cc1] | 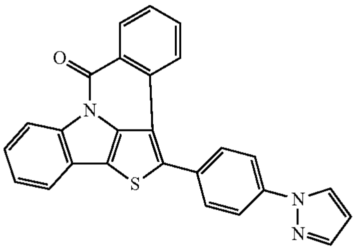 [SMILES: O=c1c2ccccc2c2c(-c3ccc(-n4cccn4)cc3)sc3c4ccccc4n1c32] | 60% |
| 8g | 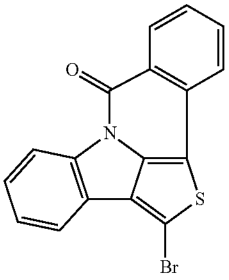 | 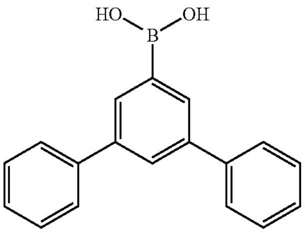 [SMILES: OB(O)c1cc(-c2ccccc2)cc(-c2ccccc2)c1] | 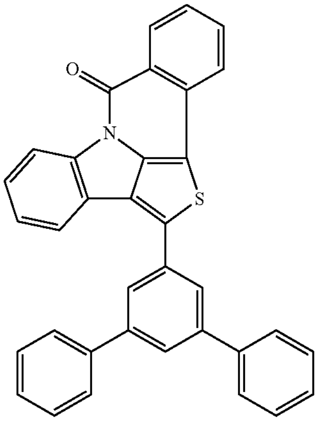 [SMILES: O=c1c2ccccc2c2sc(-c3cc(-c4ccccc4)cc(-c4ccccc4)c3)c3c4ccccc4n1c23] | 92% |
| 8h | 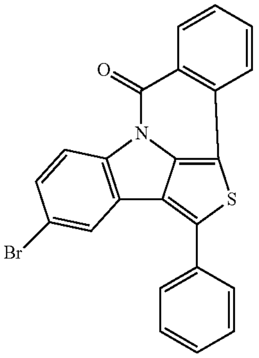 | 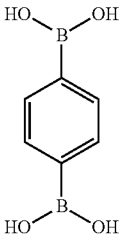 [SMILES: OB(O)c1ccc(B(O)O)cc1] | 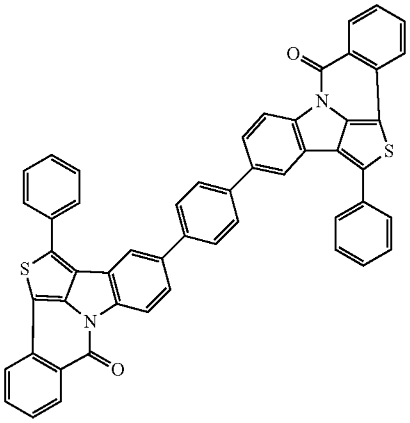 [SMILES: O=c1c2ccccc2c2sc(-c3ccccc3)c3c4cc(-c5ccc(-c6ccc7c(c6)c6c(-c8ccccc8)sc8c9ccccc9c(=O)n7c86)cc5)ccc4n1c23] | 65% |

-continued
| Ex. | Starting material 1 | Starting material 2 | Product | Yield. |
|---|---|---|---|---|
| 8i | 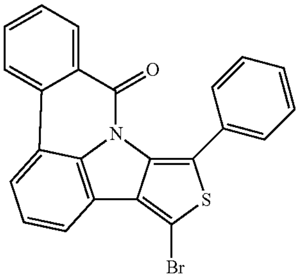 [SMILES: O=c1c2ccccc2c2cccc3c4c(Br)sc(-c5ccccc5)c4n1c23] | 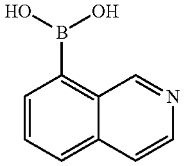 [SMILES: OB(O)c1cccc2ccncc12] | 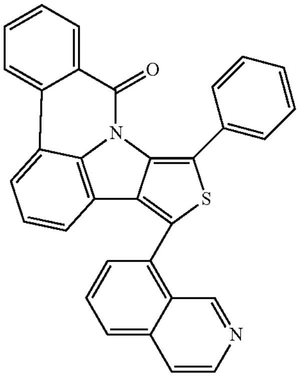 [SMILES: O=c1c2ccccc2c2cccc3c4c(-c5cccc6ccncc56)sc(-c5ccccc5)c4n1c23] | 80% |
| 8j | 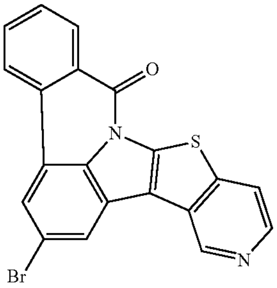 [SMILES: O=c1c2ccccc2c2cc(Br)cc3c4c5cnccc5sc4n1c23] | 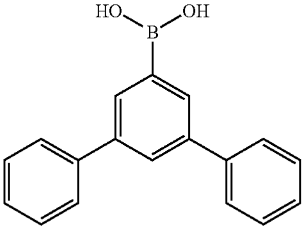 [SMILES: OB(O)c1cc(-c2ccccc2)cc(-c2ccccc2)c1] | 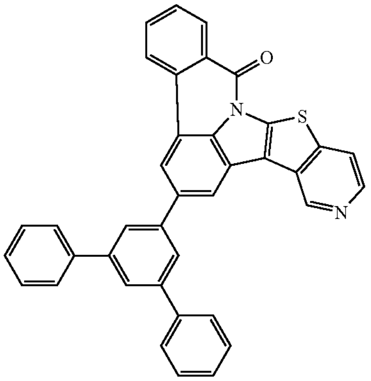 [SMILES: O=c1c2ccccc2c2cc(-c3cc(-c4ccccc4)cc(-c4ccccc4)c3)cc3c4c5cnccc5sc4n1c23] | 84% |
| 8k | 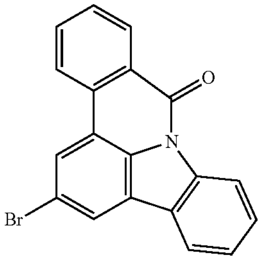 [SMILES: O=c1c2ccccc2c2cc(Br)cc3c4ccccc4n1c23] | 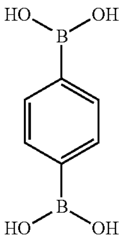 [SMILES: OB(O)c1ccc(B(O)O)cc1] | 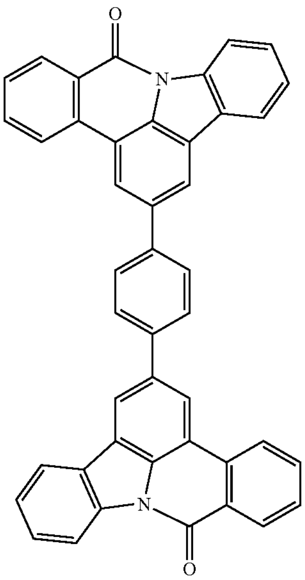 [SMILES: O=c1c2ccccc2c2cc(-c3ccc(-c4cc5c6ccccc6c(=O)n6c7ccccc7c(c4)c56)cc3)cc3c4ccccc4n1c23] | 64% |

-continued
| Ex. | Starting material 1 | Starting material 2 | Product | Yield. |
|---|---|---|---|---|
| 8l | 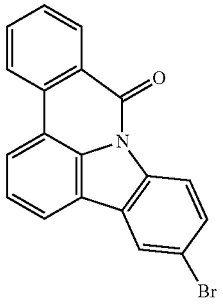 [SMILES: O=c1c2ccccc2c2cccc3c4cc(Br)ccc4n1c23] | 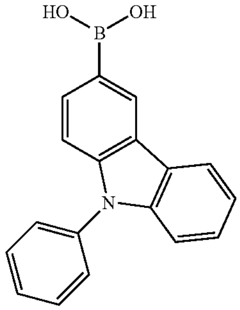 [SMILES: OB(O)c1ccc2c(c1)c1ccccc1n2-c1ccccc1] | 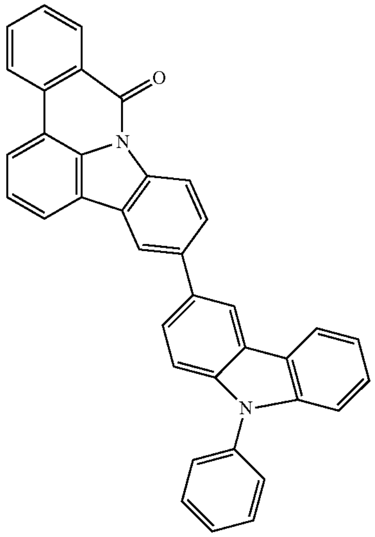 [SMILES: O=c1c2ccccc2c2cccc3c4cc(-c5ccc6c(c5)c5ccccc5n6-c5ccccc5)ccc4n1c23] | 76% |
| 8m | 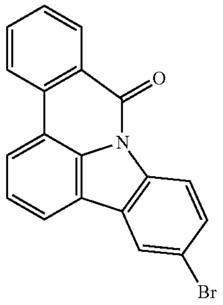 [SMILES: O=c1c2ccccc2c2cccc3c4cc(Br)ccc4n1c23] | 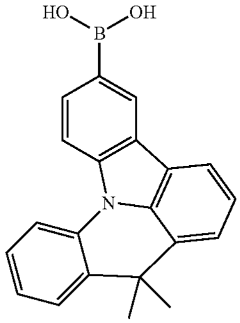 [SMILES: CC1(C)c2ccccc2-n2c3ccc(B(O)O)cc3c3cccc1c32] | 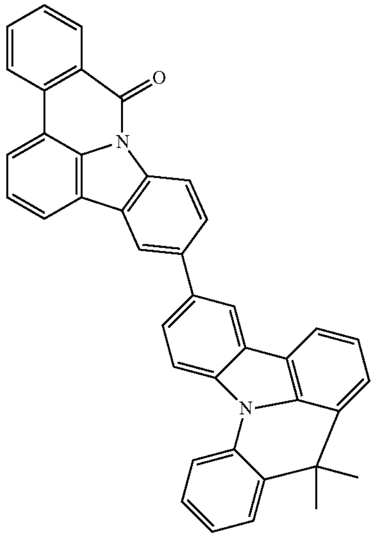 [SMILES: CC1(C)c2ccccc2-n2c3ccc(-c4ccc5c(c4)c4cccc6c7ccccc7c(=O)n5c64)cc3c3cccc1c32] | 74% |
| 8n | 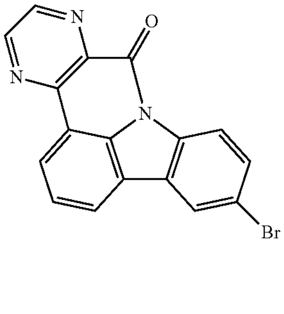 [SMILES: O=c1c2nccnc2c2cccc3c4cc(Br)ccc4n1c32] | 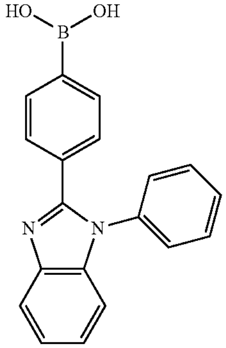 [SMILES: OB(O)c1ccc(-c2nc3ccccc3n2-c2ccccc2)cc1] | 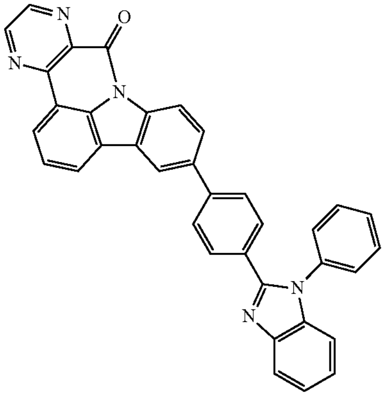 [SMILES: O=c1c2nccnc2c2cccc3c4cc(-c5ccc(-c6nc7ccccc7n6-c6ccccc6)cc5)ccc4n1c32] | 89% |

-continued

| Ex. | Starting material 1 | Starting material 2 | Product | Yield. |
|---|---|---|---|---|
| 8o | 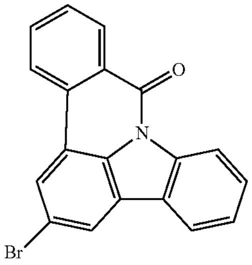 [SMILES: O=c1c2ccccc2c2cc(Br)cc3c4ccccc4n1c23] | 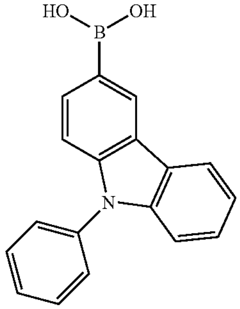 [SMILES: OB(O)c1ccc2c(c1)c1ccccc1n2-c1ccccc1] | 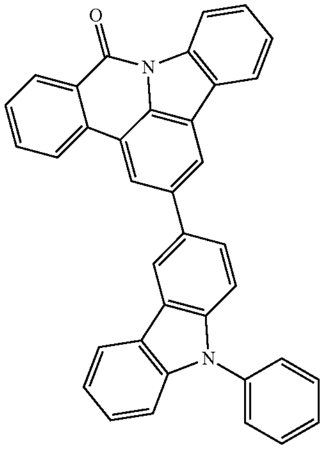 [SMILES: O=c1c2ccccc2c2cc(-c3ccc4c(c3)c3ccccc3n4-c3ccccc3)cc3c4ccccc4n1c23] | 76% |
| 8p | 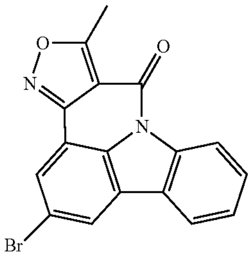 [SMILES: Cc1onc2c1c(=O)n1c3ccccc3c3cc(Br)cc2c31] | 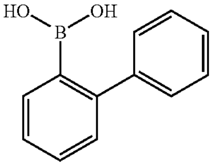 [SMILES: OB(O)c1ccccc1-c1ccccc1] | 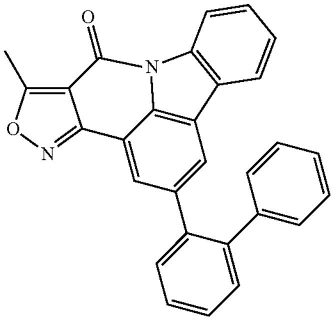 [SMILES: Cc1onc2c1c(=O)n1c3ccccc3c3cc(-c4ccccc4-c4ccccc4)cc2c31] | 59% |
| 8q | 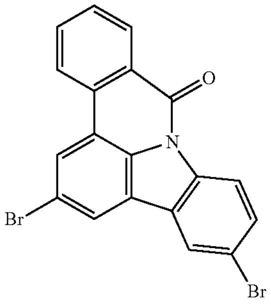 [SMILES: O=c1c2ccccc2c2cc(Br)cc3c4cc(Br)ccc4n1c23] | 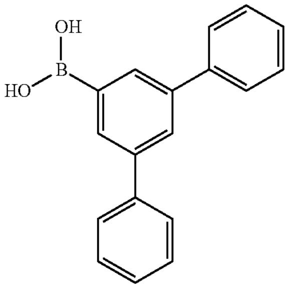 [SMILES: OB(O)c1cc(-c2ccccc2)cc(-c2ccccc2)c1] | 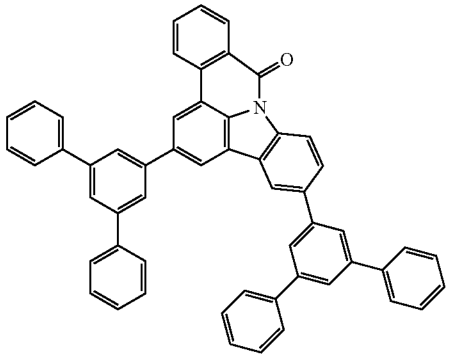 [SMILES: O=c1c2ccccc2c2cc(-c3cc(-c4ccccc4)cc(-c4ccccc4)c3)cc3c4cc(-c5cc(-c6ccccc6)cc(-c6ccccc6)c5)ccc4n1c23] | 68% |

Example 9a

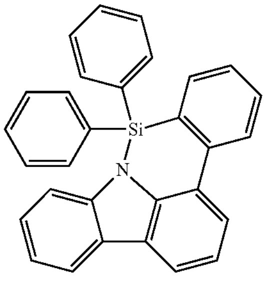 [SMILES: c1ccc([Si]2(c3ccccc3)c3ccccc3-c3cccc4c5ccccc5n2c34)cc1]

A suspension of 16.7 (100 mmol) of carbazole [86-74-8], 41.1 g (110 mmol) of (2-bromophenyl)diphenylchlorosilane (prepared analogously to (2-bromophenyl)dimethylchlorosilane from 1,2-dibromobenzene and dichlorodiphenylsilane by the method of Kawachi et al., Organometallics (2007), 26(19), 4697), 22.2 g (200 mmol) of sodium carbonate, 449 mg (2 mmol) of palladium(II) acetate, 1.6 g (6 mmol) of triphenylphosphine and 100 g of glass beads (3 mm diameter) in 500 ml of xylene is heated under reflux for 16 h with vigorous stirring. The glass beads and the salts are subsequently filtered off through Celite, the organic phase is evaporated, the residue is recrystallised five times from DMF and sublimed twice in a high vacuum. The yield is 17.4 g (41 mmol), corresponding to 41% of theory.

The following compounds are obtained analogously:
| Ex. | Starting material 1 | Starting material 2 | Product | Yield |
|---|---|---|---|---|
| 9b | 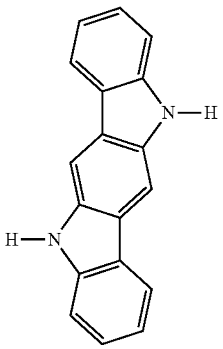 60511-85-5 50 mmol | 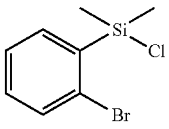 | 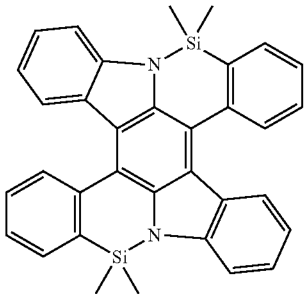 [SMILES: C[Si]1(C)c2ccccc2-c2c3c4ccccc4n4c3c(c3c5ccccc5n1c23)-c1ccccc1[Si]4(C)C] | 29% |
| 9c | 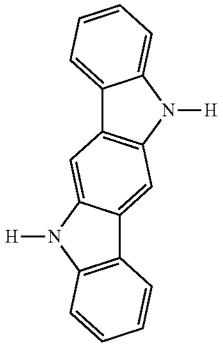 6336-32-9 50 mmol | 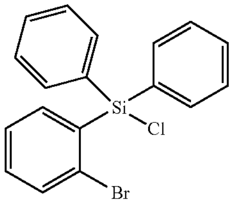 [SMILES: Cl[Si](c1ccccc1)(c1ccccc1)c1ccccc1Br] | 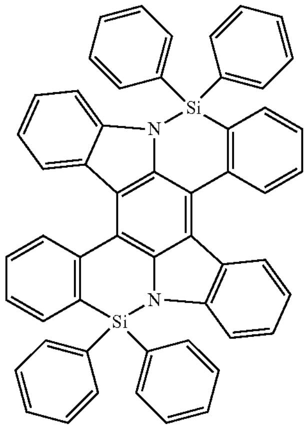 [SMILES: c1ccc([Si]2(c3ccccc3)c3ccccc3-c3c4c5ccccc5n5c4c(c4c6ccccc6n2c34)-c2ccccc2[Si]5(c2ccccc2)c2ccccc2)cc1] | 27% |
| 9d | 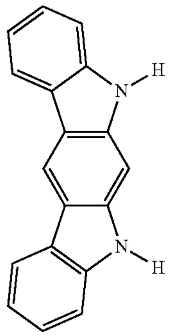 111296-90-3 50 mmol | 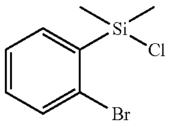 | 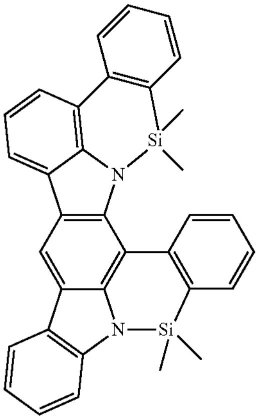 [SMILES: C[Si]1(C)c2ccccc2-c2c3c(cc4c5cccc6c5n(c24)[Si](C)(C)c2ccccc2-6)c2ccccc2n31] | 34% |

-continued

| Ex. | Starting material 1 | Starting material 2 | Product | Yield |
|---|---|---|---|---|
| 9e | 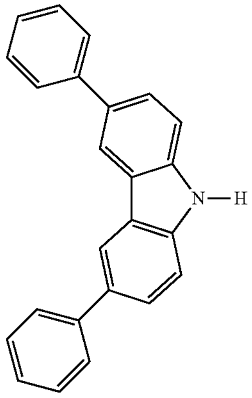 56525-79-2 | 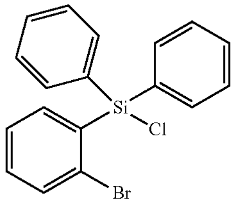 [SMILES: Cl[Si](c1ccccc1)(c1ccccc1)c1ccccc1Br] | 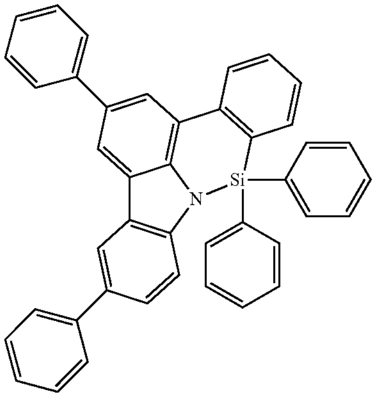 [SMILES: c1ccc(-c2ccc3c(c2)c2cc(-c4ccccc4)cc4c2n3[Si](c2ccccc2)(c2ccccc2)c2ccccc2-4)cc1] | 40% |
| 9f | 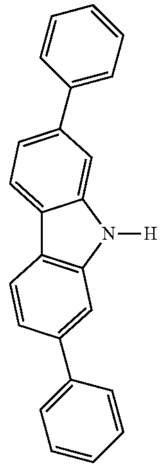 42448-04-4 | 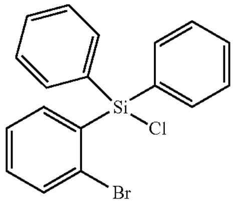 [SMILES: Cl[Si](c1ccccc1)(c1ccccc1)c1ccccc1Br] | 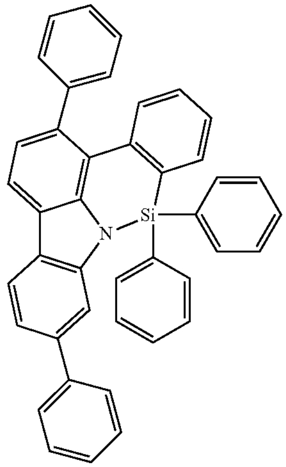 [SMILES: c1ccc(-c2ccc3c4ccc(-c5ccccc5)c5c4n(c3c2)[Si](c2ccccc2)(c2ccccc2)c2ccccc2-5)cc1] | 35% |

Example 10

Production of OLEDs

OLEDs according to the invention and OLEDs in accordance with the prior art are produced by a general process in accordance with WO 2004/058911, which is adapted to the circumstances described here (layer-thickness variation, materials).

The data for various OLEDs are presented in Examples 11 to 137 below (see Tables 1 and 2). Glass plates which have been coated with structured ITO (indium tin oxide) in a thickness of 150 nm are coated with 20 nm of PEDOT (poly(3,4-ethylenedioxy-2,5-thiophene), applied by spin-coating from water; purchased from H. C. Starck, Goslar, Germany) for improved processing. These coated glass plates form the substrates to which the OLEDs are applied. The OLEDs have in principle the following layer structure: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. A name such as "3a" relates here to the materials shown in the tables above for Example 3a. The other materials required for the production of the OLEDs are shown in Table 3.

All materials are applied by thermal vapour deposition in a vacuum chamber. The emission layer here always consists of at least one matrix material (host material) and an emitting dopant (emitter), to which the matrix material or matrix materials is admixed in a certain proportion by volume by co-evaporation. An indication such as ST1:9a:TEG1 (30%:60%:10%) here means that material ST1 is present in the layer in a proportion by volume of 30%, 9a is present in the layer in a proportion by volume of 60% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), and the lifetime are determined. The electroluminescence spectrum are determined at a luminous density of 1000 cd/m$^2$, and the CIE 1931 x and y colour coordinates are calculated therefrom. U1000 in Table 2 denotes the voltage required for a luminous density of 1000 cd/$m^2$. CE1000 and PE1000 denote the current efficiency and power efficiency respectively which are achieved at 1000 cd/$m^2$. Finally, EQE1000 is the external quantum efficiency at an operating luminous density of 1000 cd/$m^2$.

The data for the various OLEDs are summarised in Table 2.

Some of the examples are explained in greater detail below. However, it should be pointed out that this only represents a selection of the data shown in Table 2.

Use of Compounds According to the Invention as Electron-Transport Materials

Use of materials according to the invention in the electron-transport layer produces good voltages, efficiencies and lifetimes. In combination with the blue-fluorescent dopant D1, a voltage of 4.9 V (Example 15), for example, is obtained. On use of a mixed layer of material 8n with LiQ, an external quantum efficiency of 5.3% is obtained (Example 16). OLEDs in accordance with Example 14 exhibit a drop in luminance from 6000 to 3000 cd/$m^2$ ("LT50") after an operating duration of about 170 h on operation with constant current, which represents a very good value. This corresponds to a lifetime of about 6000 h at 1000 cd/$m^2$.

Use of Compounds According to the Invention as Matrix Materials in Phosphorescent OLEDs On use of materials according to the invention as matrix for phosphorescent emitters, very good performance data are likewise obtained.

With compound 8o, for example, in combination with the green-emitting material TEG1, a very good external quantum efficiency of 15.2% is obtained, which, in combination with the low voltage of 3.5 V, results in a very good power efficiency of 49 lm/W (Example I16). The corresponding OLEDs exhibit a drop in luminance from 4000 to 3200 cd/$m^2$ over the course of about 340 h ("LT80") on operation with constant current. On use of materials according to the invention as second matrix component, even better LT80 values of up to 420 h at an initial luminance of 4000 cd/$m^2$ are obtained (Example I18).

In combination with the red-emitting dopant TER1, good performance data likewise arise. Thus, for example, with compound 7t as matrix, an external quantum efficiency of 13.6% is obtained, which, with the voltage of 4.6 V, gives rise to a power efficiency of 5.9 lm/W. For this combination, an LT80 value of about 410 h is obtained at an initial luminance of 4000 cd/$m^2$ (Example I35). Even better lifetimes can be achieved on use of compounds 7k and 7l. LT80 values of about 520 and 460 h respectively (Examples 129, 130) are obtained therewith.

Use of Compounds According to the Invention as Dopant in Blue-Fluorescent OLEDs

Compound 31 can be employed as blue-fluorescent dopant. In this case, deep-blue colour coordinates with CIE x/y=0.14/0.14 and an external quantum efficiency of 4.7% are obtained at a voltage of 4.4 V (Example I20).

TABLE 1

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| I1 | HATCN 5 nm | SpA1 140 nm | — | NPB 20 nm | M1:D1 (95%:5%) 30 nm | — | 3j 20 nm | LiQ 3 nm |
| I2 | HATCN 5 nm | SpA1 140 nm | — | NPB 20 nm | M1:D1 (95%:5%) 30 nm | — | 7m 20 nm | LiQ 3 nm |
| I3 | HATCN 5 nm | SpA1 140 nm | — | NPB 20 nm | M1:D1 (95%:5%) 30 nm | — | 8d 20 nm | LiQ 3 nm |
| I4 | HATCN 5 nm | SpA1 140 nm | — | NPB 20 nm | M1:D1 (95%:5%) 30 nm | — | 8e 20 nm | LiF 1.5 nm |
| I5 | HATCN 5 nm | SpA1 140 nm | — | NPB 20 nm | M1:D1 (95%:5%) 30 nm | — | 8i 20 nm | LiQ 3 nm |
| I6 | HATCN 5 nm | SpA1 140 nm | — | NPB 20 nm | M1:D1 (95%:5%) 30 nm | — | 8n:LiQ (50%:50%) 20 nm | — |
| I7 | — | SpA1 70 nm | HATCN 5 nm | BPA1 20 nm | 3h:TEG1 (90%:10%) 30 nm | ST1 10 nm | ST1:LiQ (50%:50%) 30 nm | — |
| I8 | — | SpA1 70 nm | HATCN 5 nm | BPA1 20 nm | 6a:TEG1 (90%:10%) 30 nm | ST1 10 nm | ST1:LiQ (50%:50%) 30 nm | — |
| I9 | — | SpA1 70 nm | HATCN 5 nm | BPA1 20 nm | 6c:TEG1 (90%:10%) 30 nm | ST1 10 nm | ST1:LiQ (50%:50%) 30 nm | — |
| I10 | — | SpA1 70 nm | HATCN 5 nm | BPA1 20 nm | 7n:TEG1 (90%:10%) 30 nm | ST1 10 nm | ST1:LiQ (50%:50%) 30 nm | — |
| I11 | — | SpA1 70 nm | HATCN 5 nm | BPA1 20 nm | 7o:TEG1 (90%:10%) 30 nm | ST1 10 nm | ST1:LiQ (50%:50%) 30 nm | — |
| I12 | — | SpA1 70 nm | HATCN 5 nm | BPA1 20 nm | 7w:TEG1 (90%:10%) 30 nm | ST1 10 nm | ST1:LiQ (50%:50%) 30 nm | — |
| I13 | — | SpA1 70 nm | HATCN 5 nm | BPA1 20 nm | 8k:TEG1 (90%:10%) 30 nm | ST1 10 nm | ST1:LiQ (50%:50%) 30 nm | — |
| I14 | — | SpA1 70 nm | HATCN 5 nm | BPA1 20 nm | 8l:TEG1 (90%:10%) 30 nm | ST1 10 nm | ST1:LiQ (50%:50%) 30 nm | — |
| I15 | — | SpA1 70 nm | HATCN 5 nm | BPA1 20 nm | 8m:TEG1 (90%:10%) 30 nm | ST1 10 nm | ST1:LiQ (50%:50%) 30 nm | — |
| I16 | — | SpA1 70 nm | HATCN 5 nm | BPA1 20 nm | 8o:TEG1 (90%:10%) 30 nm | ST1 10 nm | ST1:LiQ (50%:50%) 30 nm | — |
| I17 | — | SpA1 70 nm | HATCN 5 nm | BPA1 20 nm | 8q:TEG1 (90%:10%) 30 nm | ST1 10 nm | ST1:LiQ (50%:50%) 30 nm | — |
| I18 | — | SpA1 70 nm | HATCN 5 nm | BPA1 20 nm | ST1:9a:TEG1 (30%:60%:10%) 30 nm | ST1 10 nm | ST1:LiQ (50%:50%) 30 nm | — |
| I19 | — | SpA1 70 nm | HATCN 5 nm | BPA1 20 nm | ST1:9e:TEG1 (30%:60%:10%) 30 nm | ST1 10 nm | ST1:LiQ (50%:50%) 30 nm | — |

TABLE 1-continued

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| I20 | HATCN 5 nm | SpA1 140 nm | — | NPB 20 nm | M1:3l (95%:5%) 30 nm | — | ST1 35 nm | LiQ 3 nm |
| I21 | — | SpA1 160 nm | HATCN 5 nm | NPB 20 nm | 3a:TER1 (85%:15%) 35 nm | ST1 10 nm | ST1:LiQ (50%:50%) 35 nm | — |
| I22 | — | SpA1 160 nm | HATCN 5 nm | NPB 20 nm | 6b:TER1 (85%:15%) 35 nm | ST1 10 nm | ST1:LiQ (50%:50%) 35 nm | — |
| I23 | — | SpA1 160 nm | HATCN 5 nm | NPB 20 nm | 7a:TER1 (85%:15%) 35 nm | ST1 10 nm | ST1:LiQ (50%:50%) 35 nm | — |
| I24 | — | SpA1 160 nm | HATCN 5 nm | NPB 20 nm | 7b:TER1 (85%:15%) 35 nm | ST1 10 nm | ST1:LiQ (50%:50%) 35 nm | — |
| I25 | — | SpA1 160 nm | HATCN 5 nm | NPB 20 nm | 7e:TER1 (85%:15%) 35 nm | ST1 10 nm | ST1:LiQ (50%:50%) 35 nm | — |
| I26 | — | SpA1 160 nm | HATCN 5 nm | NPB 20 nm | 7f:TER1 (85%:15%) 35 nm | ST1 10 nm | ST1:LiQ (50%:50%) 35 nm | — |
| I27 | — | SpA1 160 nm | HATCN 5 nm | NPB 20 nm | 7g:TER1 (85%:15%) 35 nm | ST1 10 nm | ST1:LiQ (50%:50%) 35 nm | — |
| I28 | — | SpA1 160 nm | HATCN 5 nm | NPB 20 nm | 7j:TER1 (85%:15%) 35 nm | ST1 10 nm | ST1:LiQ (50%:50%) 35 nm | — |
| I29 | — | SpA1 160 nm | HATCN 5 nm | NPB 20 nm | 7k:TER1 (85%:15%) 35 nm | ST1 10 nm | ST1:LiQ (50%:50%) 35 nm | — |
| I30 | — | SpA1 160 nm | HATCN 5 nm | NPB 20 nm | 7l:TER1 (85%:15%) 35 nm | ST1 10 nm | ST1:LiQ (50%:50%) 35 nm | — |
| I31 | — | SpA1 160 nm | HATCN 5 nm | NPB 20 nm | 7p:TER1 (85%:15%) 35 nm | ST1 10 nm | ST1:LiQ (50%:50%) 35 nm | — |
| I32 | — | SpA1 160 nm | HATCN 5 nm | NPB 20 nm | 7q:TER1 (85%:15%) 35 nm | ST1 10 nm | ST1:LiQ (50%:50%) 35 nm | — |
| I33 | — | SpA1 160 nm | HATCN 5 nm | NPB 20 nm | 7r:TER1 (85%:15%) 35 nm | ST1 10 nm | ST1:LiQ (50%:50%) 35 nm | — |
| I34 | — | SpA1 160 nm | HATCN 5 nm | NPB 20 nm | 7s:TER1 (85%:15%) 35 nm | ST1 10 nm | ST1:LiQ (50%:50%) 35 nm | — |
| I35 | — | SpA1 160 nm | HATCN 5 nm | NPB 20 nm | 7t:TER1 (85%:15%) 35 nm | ST1 10 nm | ST1:LiQ (50%:50%) 35 nm | — |
| I36 | — | SpA1 160 nm | HATCN 5 nm | NPB 20 nm | 7v:TER1 (85%:15%) 35 nm | ST1 10 nm | ST1:LiQ (50%:50%) 35 nm | — |
| I37 | — | SpA1 160 nm | HATCN 5 nm | NPB 20 nm | ST1:9f:TER1 (30%:60%:10%) 35 nm | ST1 10 nm | ST1:LiQ (50%:50%) 35 nm | — |

TABLE 2

Data for the OLEDs

| Ex. | U1000 (V) | CE1000 (cd/A) | PE1000 (lm/W) | EQE 1000 | CIE x/y at 1000 cd/m$^2$ |
|---|---|---|---|---|---|
| I1 | 5.9 | 4.8 | 2.6 | 4.0% | 0.14/0.15 |
| I2 | 6.3 | 4.5 | 2.2 | 3.7% | 0.14/0.15 |
| I3 | 5.8 | 5.5 | 3.0 | 4.5% | 0.14/0.15 |
| I4 | 5.5 | 5.8 | 3.3 | 4.8% | 0.14/0.15 |
| I5 | 4.9 | 6.3 | 4.0 | 5.2% | 0.14/0.15 |
| I6 | 5.1 | 6.4 | 3.9 | 5.3% | 0.14/0.15 |
| I7 | 4.3 | 46 | 34 | 12.7% | 0.37/0.61 |
| I8 | 4.0 | 43 | 33 | 11.9% | 0.37/0.61 |
| I9 | 3.9 | 49 | 39 | 13.7% | 0.37/0.60 |
| I10 | 3.6 | 39 | 34 | 10.8% | 0.36/0.59 |
| I11 | 3.5 | 44 | 40 | 12.3% | 0.37/0.60 |
| I12 | 3.9 | 51 | 42 | 14.2% | 0.36/0.60 |
| I13 | 4.1 | 48 | 37 | 13.4% | 0.37/0.60 |
| I14 | 3.5 | 41 | 37 | 11.5% | 0.37/0.61 |
| I15 | 3.8 | 36 | 30 | 10.1% | 0.37/0.61 |
| I16 | 3.5 | 55 | 49 | 15.2% | 0.37/0.60 |
| I17 | 3.7 | 44 | 38 | 12.2% | 0.37/0.61 |
| I18 | 3.7 | 49 | 42 | 13.6% | 0.37/0.61 |
| I19 | 3.8 | 46 | 38 | 12.9% | 0.37/0.61 |
| I20 | 4.4 | 5.1 | 3.6 | 4.7% | 0.14/0.14 |
| I21 | 4.7 | 7.3 | 4.9 | 11.5% | 0.69/0.31 |
| I22 | 5.3 | 7.0 | 4.1 | 10.9% | 0.69/0.31 |
| I23 | 5.1 | 5.9 | 3.6 | 9.3% | 0.69/0.31 |
| I24 | 5.4 | 5.5 | 3.2 | 8.6% | 0.69/0.31 |
| I25 | 4.5 | 6.2 | 4.3 | 9.7% | 0.69/0.31 |
| I26 | 5.1 | 6.7 | 4.1 | 10.4% | 0.69/0.31 |
| I27 | 4.9 | 6.4 | 4.1 | 10.1% | 0.69/0.31 |
| I28 | 4.3 | 7.2 | 5.3 | 11.5% | 0.69/0.31 |
| I29 | 4.7 | 8.3 | 5.6 | 13.0% | 0.69/0.31 |
| I30 | 4.4 | 7.8 | 5.6 | 12.2% | 0.69/0.31 |
| I31 | 6.3 | 5.5 | 2.7 | 8.6% | 0.69/0.31 |
| I32 | 5.9 | 5.3 | 2.8 | 8.3% | 0.69/0.31 |
| I33 | 5.3 | 6.1 | 3.6 | 9.6% | 0.69/0.31 |
| I34 | 4.8 | 7.2 | 4.7 | 11.3% | 0.69/0.31 |
| I35 | 4.6 | 8.6 | 5.9 | 13.6% | 0.69/0.31 |
| I36 | 4.9 | 6.8 | 4.3 | 10.7% | 0.69/0.31 |
| I37 | 4.1 | 7.5 | 5.8 | 11.9% | 0.69/0.31 |

TABLE 3
Structural formulae of the materials for the OLEDs
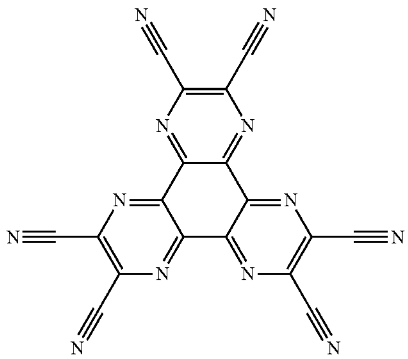 [SMILES: N#Cc1nc2c3nc(C#N)c(C#N)nc3c3nc(C#N)c(C#N)nc3c2nc1C#N]
HATCH
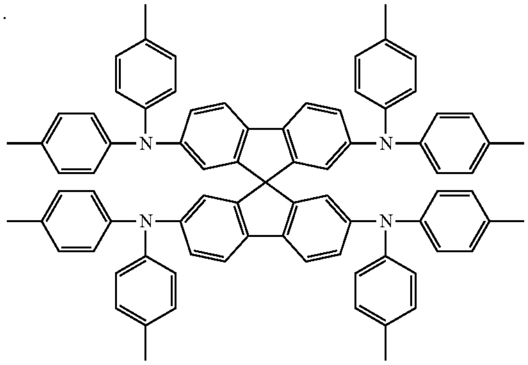
SpA1
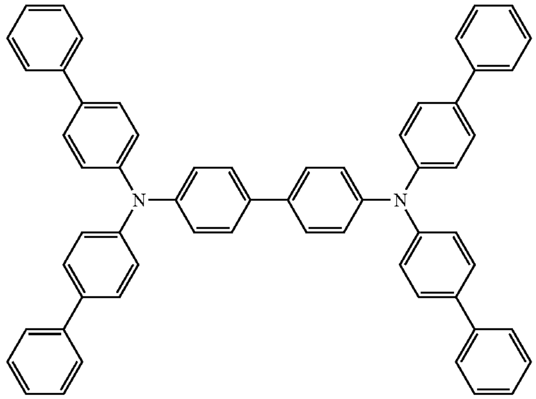 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
BPA1
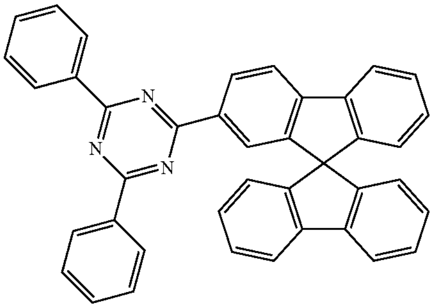 [SMILES: c1ccc(-c2nc(-c3ccccc3)nc(-c3ccc4c(c3)C3(c5ccccc5-c5ccccc53)c3ccccc3-4)n2)cc1]
ST1
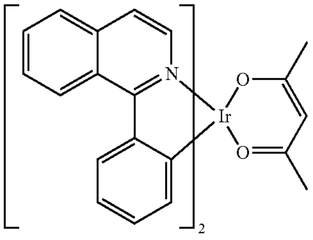
TER1
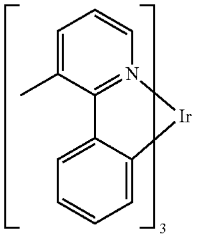
TEG1
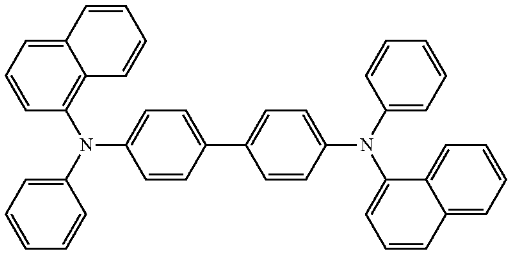 [SMILES: c1ccc(N(c2ccc(-c3ccc(N(c4ccccc4)c4cccc5ccccc45)cc3)cc2)c2cccc3ccccc23)cc1]
NPB
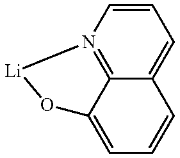
LiQ TABLE 3-continued

| Structural formulae of the materials for the OLEDs | |
|---|---|
| 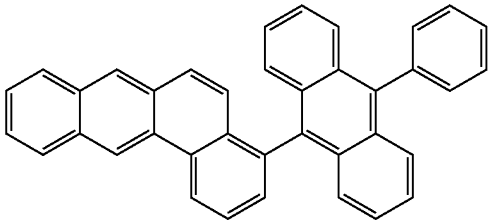 [SMILES: c1ccc(-c2c3ccccc3c(-c3cccc4c3ccc3cc5ccccc5cc34)c3ccccc23)cc1] | 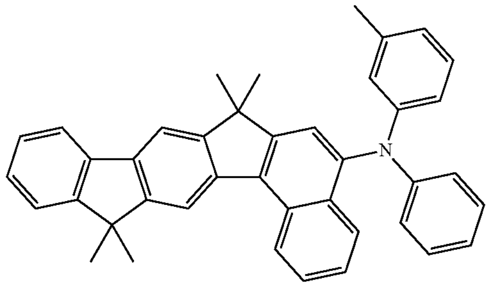 [SMILES: Cc1cccc(N(c2ccccc2)c2cc3c(c4ccccc24)-c2cc4c(cc2C3(C)C)-c2ccccc2C4(C)C)c1] |
| M1 | D1 |

The invention claimed is:

1. An electronic device comprising at least one compound of the formula (1), formula (1)

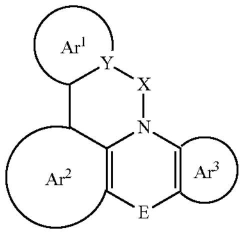

where the following applies to the symbols and indices used:

X is C═O, $C(R)_2$, NR, O, S, C═S, C═NR, $C{=}C(R)_2$, $Si(R)_2$, BR, PR, P(═O)R, SO or $SO_2$;

Y is C;

E is a single bond, $C(R)_2$, NR, O, S, C═O, C═S, C═NR, $C{=}C(R)_2$, $Si(R)_2$, BR, PR, P(═O)R, SO or $SO_2$;

$Ar^1$ is, together with the group Y and the carbon atom explicitly depicted, a 6-membered aryl ring, which is optionally substituted by one or more radicals R;

$Ar^2$ and $Ar^3$ are, identically or differently on each occurrence, together with the carbon atoms explicitly depicted, an aromatic or heteroaromatic ring system having 5 to 30 aromatic ring atoms, which is optionally substituted by one or more radicals R;

R is selected on each occurrence, identically or differently, from the group consisting of H, D, F, Cl, Br, I, CN, $NO_2$, $N(Ar^4)_2$, $N(R^1)_2$, $C(=O)Ar^4$, $C(=O)R^1$, $P(=O)(Ar^4)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^1$, where one or more non-adjacent $CH_2$ groups is optionally replaced by $R^1C{=}CR^1$, C≡C, $Si(R^1)_2$, $Ge(R^1)_2$, $Sn(R^1)_2$, C═O, C═S, C═Se, $C{=}NR^1$, $P(=O)(R^1)$, SO, $SO_2$, $NR^1$, O, S or $CONR^1$ and where one or more H atoms is optionally replaced by D, F, Cl, Br, I, CN or $NO_2$, an aromatic or heteroaromatic ring system having 5 to 80 aromatic ring atoms, which optionally in each case be substituted by one or more radicals $R^1$, an aryloxy or heteroaryloxy group having 5 to 60 aromatic ring atoms, which is optionally substituted by one or more radicals $R^1$, or a combination of these systems, where two or more adjacent substituents R may optionally form a monocyclic or polycyclic, aliphatic, aromatic or heteroaromatic ring system, which is optionally substituted by one or more radicals $R^1$;

$R^1$ is selected on each occurrence, identically or differently, from the group consisting of H, D, F, Cl, Br, I, CN, $NO_2$, $N(Ar^4)_2$, $N(R^2)_2$, $C(=O)Ar^4$, $C(=O)R^2$, $P(=O)(Ar^4)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^2$, where one or more non-adjacent $CH_2$ groups is optionally replaced by $R^2C{=}CR^2$, C≡C, $Si(R^2)_2$, $Ge(R^2)_2$, $Sn(R^2)_2$, C═O, C═S, C═Se, $C{=}NR^2$, $P(=O)(R^2)$, SO, $SO_2$, $NR^2$, O, S or $CONR^2$ and where one or more H atoms is optionally replaced by D, F, Cl, Br, I, CN or $NO_2$, an aromatic or heteroaromatic ring system having 5 to 60 aromatic ring atoms, which optionally in each case be substituted by one or more radicals $R^2$, an aryloxy or heteroaryloxy group having 5 to 60 aromatic ring atoms, which is optionally substituted by one or more radicals $R^2$, or a combination of these systems, where two or more adjacent substituents R optionally forms a monocyclic or polycyclic, aliphatic, aromatic or heteroaromatic ring system, which is optionally substituted by one or more radicals $R^2$;

$Ar^4$ is on each occurrence, identically or differently, an aromatic or heteroaromatic ring system having 5-30 aromatic ring atoms, which is optionally substituted by one or more non-aromatic radicals $R^2$; two radicals $Ar^4$ here which are bonded to the same N atom or P atom may also be bridged to one another by a single bond or a bridge selected from $N(R^2)$, $C(R^2)_2$ or O; and $R^2$ is H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I or CN, where two or more adjacent substituents $R^2$ may form a mono- or polycyclic, aliphatic, aromatic or heteroaromatic ring system with one another.

2. The electronic device according to claim 1, wherein the device is an organic electroluminescent device, an organic integrated circuit, an organic field-effect transistor, an organic thin-film transistor, an organic light-emitting transistor, an organic solar cell, an organic dye-sensitised solar cell, an organic optical detector, an organic photoreceptor, an organic field-quench device, a light-emitting electrochemical cell, an organic laser diode or an organic plasmon emitting device.

3. The electronic device according to claim 1, wherein the group $Ar^2$ stands for a group of one of the formulae (9), (10) or (11), formula (9)

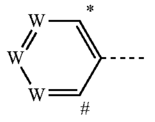

formula (10)

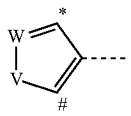

formula (11)

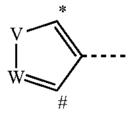

where the dashed bond indicates the link to N, indicates the position of the link to E,

* indicates the link to $Ar^1$,

W is, identically or differently on each occurrence, CR or N; or two adjacent groups W stand for a group of the formula (7) or (8), formula (7)

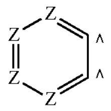

formula (8)

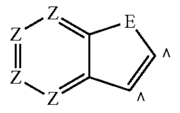

wherein

E is a single bond, $C(R)_2$, NR, O, S, C═O, C═S, C═NR, C═$C(R)_2$, $Si(R)_2$, BR, PR, P(═O)R, SO or $SO_2$;

Z stands, identically or differently on each occurrence, for CR or N and

V is NR, O or S.

4. The electronic device according to claim 1, wherein the group $Ar^3$ stands for a group of one of the formulae (12), (13), (14) or (15), formula (12)

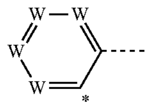

formula (13)

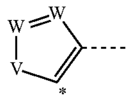

-continued formula (14)

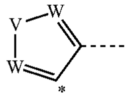

formula (15)

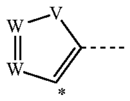

where the dashed bond indicates the link to N,

* indicates the link to E;

W is, identically or differently on each occurrence, CR or N; or two adjacent groups W stand for a group of the formula (7) or (8), formula (7)

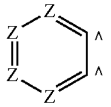

formula (8)

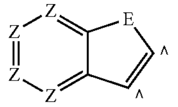

wherein

E is a single bond, $C(R)_2$, NR, O, S, C═O, C═S, C═NR, C═$C(R)_2$, $Si(R)_2$, BR, PR, P(═O)R, SO or $SO_2$;

Z stands, identically or differently on each occurrence, for CR or N and

V is NR, O or S.

5. The electronic device according to claim 1, wherein

X is C═O, $CR_2$, $SiR_2$, P(═O)R or $SO_2$;

E is, identically or differently on each occurrence, a single bond, $CR_2$, C═O, NR, O or S;

$Ar^2$ is selected from the groups of the formulae (9), (10) or (11)

formula (9)

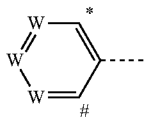

formula (10)

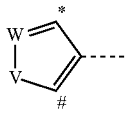

formula (11)

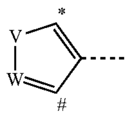

where the dashed bond indicates the link to N;

# indicates the position of the link to E;

* indicates the link to $Ar^1$ and

W is, identically or differently on each occurrence, CR or N; or two adjacent groups W stand for a group of the formula (7) or (8), formula (7)

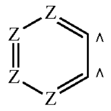

formula (8)

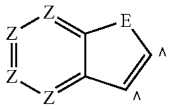

where

E is defined above;

Z stands, identically or differently on each occurrence, for CR or N;

^ indicated the corresponding adjacent groups W in the formula (2) to (6); and

V is NR, O or S;

$Ar^3$ is selected from the groups of the formulae (12), (13), (14) or (15)

formula (12)

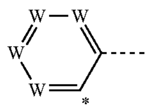

formula (13)

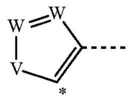

formula (14)

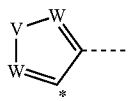

formula (15)

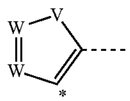

where the dashed bond indicates the link to N,

* indicates the link to E and

W and V are defined above.

6. The electronic device according to claim 1, wherein the compound of the formula (1) is a compound of the formulae (16) and (21) to (25), formula (16)

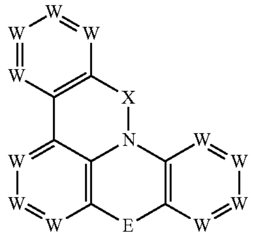

formula (21)

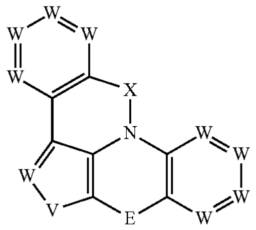

formula (22)

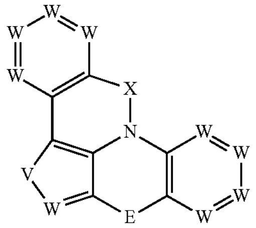

formula (23)

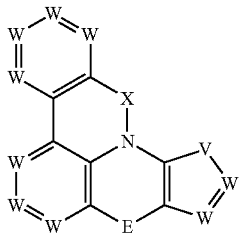

formula (24)

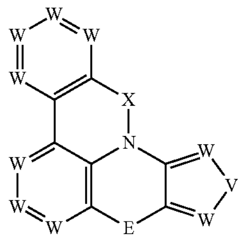

formula (25)

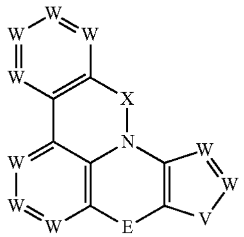

where the symbols used have the meanings given in claim 1 and W is CR.

7. The electronic device according to claim 1, wherein the compound of the formula (1) is a compound of the formulae (16a) and (21a) to (25a), formula (16a)
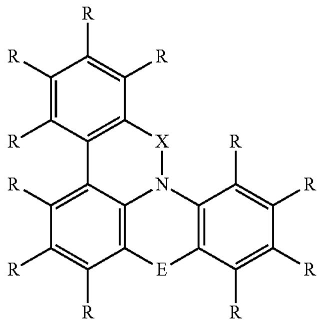
formula (21a)
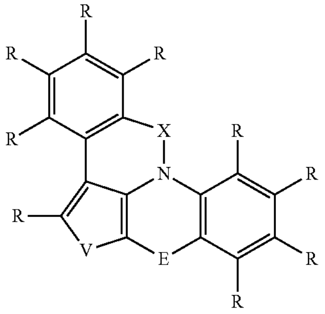
formula (22a)
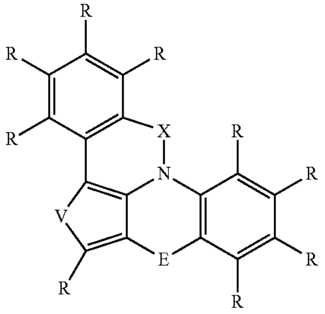
formula (23a)
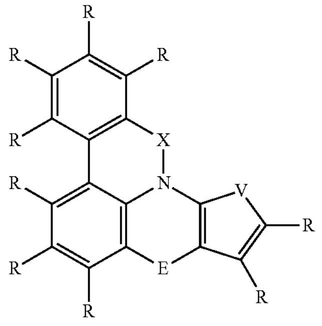
formula (24a)
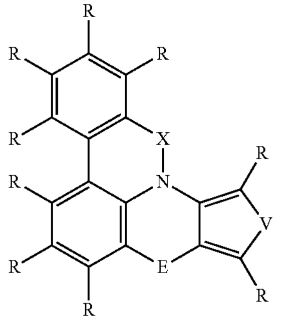
-continued
formula (25a)
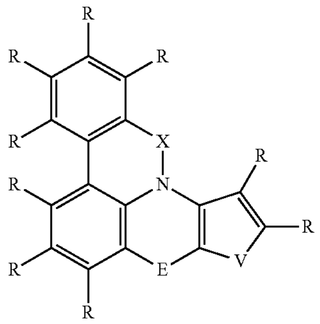
where the symbols used have the meanings given in claim 1.
8. The electronic device according to claim 1, wherein the compound of the formula (1) is a compound of the formulae (16c) and (21c)to (25c),
formula (16c)
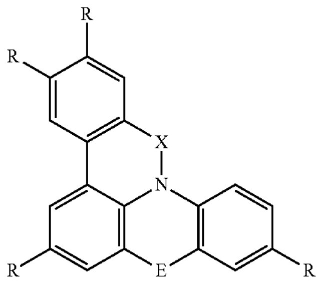
formula (21c)
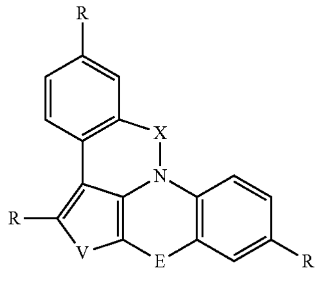
formula (22c)
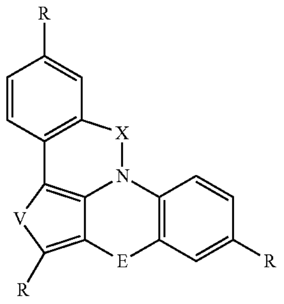

-continued formula (23c)

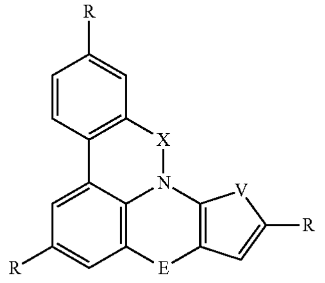

formula (24c)

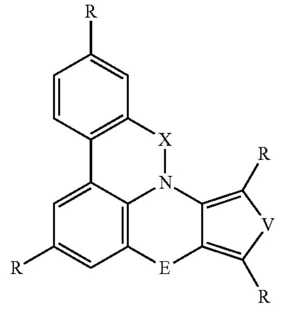

formula (25c)

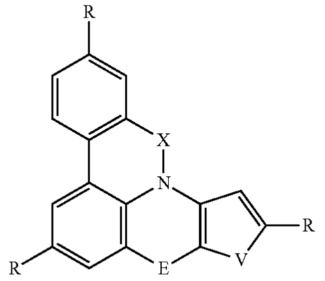

where the symbols used have the meanings given in claim 1.

9. The electronic device according to claim 1, wherein R is, identically or differently on each occurrence, and is H, D, F, Cl, Br, CN, $N(Ar^1)_2$, $C(=O)Ar^1$, a straight-chain alkyl or alkoxy group having 1 to 10 C atoms or a branched or cyclic alkyl or alkoxy group having 3 to 10 C atoms or an alkenyl or alkynyl group having 2 to 10 C atoms, each of which is optionally substituted by one or more radicals $R^1$, where one or more non-adjacent $CH_2$ groups is optionally replaced by O and where one or more H atoms is optionally replaced by D or F, an aromatic or heteroaromatic ring system having 5 to 30 aromatic ring atoms, which may in each case be substituted by one or more radicals $R^1$, an aryloxy or heteroaryloxy group having 5 to 30 aromatic ring atoms, which is optionally substituted by one or more radicals $R^1$, or a combination of these systems.

10. The electronic device according to claim 1, wherein the device is an organic electroluminescent device, and the compound of the formula (1) is employed as matrix material for fluorescent or phosphorescent emitters, and/or in a hole-blocking layer and/or in an electron-transport layer and/or in an electron-blocking or exciton-blocking layer and/or in a hole-transport layer and/or in an optical coupling-out layer.

11. The electronic device according to claim 1, wherein the device is an organic electroluminescent device, and the compound of the formula (1) is employed as matrix material for phosphorescent emitters.

12. A compound of the formula (1'), formula (1')

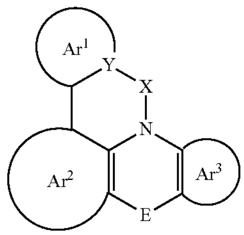

where the compound is substituted by at least one radical R which represents an aromatic or heteroaromatic ring system, X is C=O, $C(R)_2$, NR, O, S, C=S, C=NR, $C=C(R)_2$, $Si(R)_2$, BR, PR, P(=O)R, SO or $SO_2$;

Y is C ;

E is, identically or differently on each occurrence, $C(R)_2$, NR, O, S, C=O, C=S, C=NR, $C=C(R)_2$, $Si(R)_2$, BR, PR, P(=O)R, SO or $SO_2$;

$Ar^1$ is, together with the group Y and the carbon atom explicitly depicted, a 6-membered, aryl ring, which is optionally substituted by one or more radicals R;

$Ar^2$ is, together with the carbon atoms explicitly depicted, an aromatic or heteroaromatic ring system having 5 to 30 aromatic ring atoms, which is optionally substituted by one or more radicals R; if $Ar^2$ stands for an aromatic ring system having at least one nitrogen atom which is substituted by an aromatic or heteroaromatic radical R, this radical R then contains more than 6 aromatic C atoms;

$Ar^3$ is, together with the carbon atoms explicitly depicted, an aromatic or heteroaromatic ring system having 5 to 30 aromatic ring atoms, which is optionally substituted by one or more radicals R;

R is selected on each occurrence, identically or differently, from the group consisting of H, D, F, Cl, Br, I, CN, $NO_2$, $N(Ar^4)_2$, $N(R^1)_2$, $C(=O)Ar^4$, $C(=O)R^1$, $P(=O)(Ar^4)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^1$, where one or more non-adjacent $CH_2$ groups is optionally replaced by $R^1C=CR^1$, C≡C, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S or $CONR^1$ and where one or more H atoms is optionally replaced by D, F, Cl, Br, I, CN or $NO_2$, an aromatic or heteroaromatic ring system having 5 to 80 aromatic ring atoms, which optionally in each case be substituted by one or more radicals $R^1$, an aryloxy or heteroaryloxy group having 5 to 60 aromatic ring atoms, which is optionally substituted by one or more radicals $R^1$, or a combination of these systems, where two or more adjacent substituents R may optionally form a monocyclic or polycyclic, aliphatic, aromatic or heteroaromatic ring system, which is optionally substituted by one or more radicals $R^1$;

$R^1$ is selected on each occurrence, identically or differently, from the group consisting of H, D, F, Cl, Br, I, CN, $NO_2$, $N(Ar^4)_2$, $N(R^2)_2$, $C(=O)Ar^4$, $C(=O)R^2$, $P(=O)(Ar^4)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^2$, where one or more non-adjacent $CH_2$ groups is optionally replaced by $R^2C{=}CR^2$, $C{\equiv}C$, $Si(R^2)_2$, $Ge(R^2)_2$, $Sn(R^2)_2$, $C{=}O$, $C{=}S$, $C{=}Se$, $C{=}NR^2$, $P({=}O)(R^2)$, SO, $SO_2$, $NR^2$, O, S or $CONR^2$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^2$, an aryloxy or heteroaryloxy group having 5 to 60 aromatic ring atoms, which is optionally substituted by one or more radicals $R^2$, or a combination of these systems, where two or more adjacent substituents R optionally forms a monocyclic or polycyclic, aliphatic, aromatic or heteroaromatic ring system, which is optionally substituted by one or more radicals $R^2$;

$Ar^4$ is on each occurrence, identically or differently, an aromatic or heteroaromatic ring system having 5-30 aromatic ring atoms, which is optionally substituted by one or more non-aromatic radicals $R^2$; two radicals $Ar^4$ which are bonded to the same N atom or P atom may also be bridged to one another by a single bond or a bridge selected from $N(R^2)$, $C(R^2)_2$ or O;

$R^2$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I or CN, where two or more adjacent substituents $R^2$ may form a mono- or polycyclic, aliphatic, aromatic or heteroaromatic ring system with one another;

the following compounds are excluded from the invention:

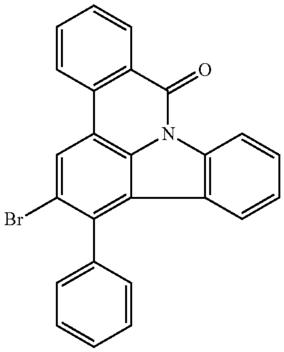
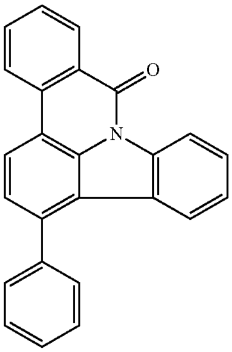
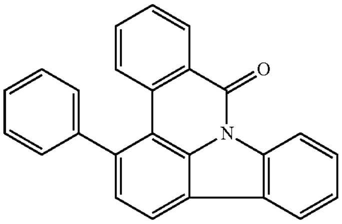

-continued

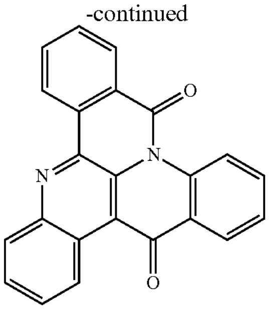

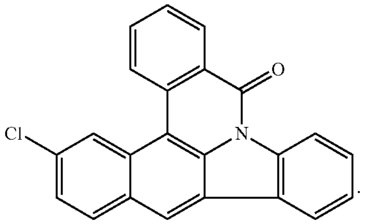

13. A process for the preparation of the compound according to claim 12, comprising the reaction steps:

a) synthesizing a skeleton which carries a reactive leaving group instead of the group R; and b) introducing the group R by a coupling reaction, wherein the coupling reaction is a Suzuki coupling or Hartwig-Buchwald coupling.

14. An oligomer, polymer or dendrimer comprising one or more of the compounds according to claim 12, where one or more bonds are present from the compound to the polymer, oligomer or dendrimer.

15. An electronic device which comprises the compound according to claim 12.

16. An organic electroluminescent device which comprises the compound according to claim 12.

17. The electronic device of claim 1, wherein the compound of formula (1) is

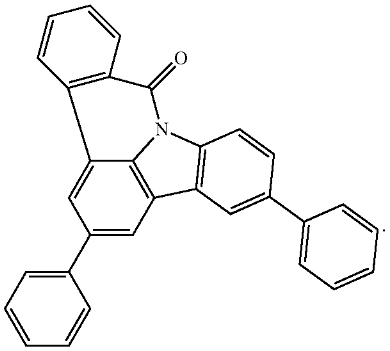 [SMILES: O=c1c2ccccc2c2cc(-c3ccccc3)cc3c4cc(-c5ccccc5)ccc4n1c23]

* * * * *